United States Patent
Kurz et al.

(10) Patent No.: US 10,829,728 B2
(45) Date of Patent: Nov. 10, 2020

(54) MICROFLUIDIC DEVICES FOR OPTICALLY-DRIVEN CONVECTION AND DISPLACEMENT, KITS AND METHODS THEREOF

(71) Applicant: Berkeley Lights, Inc., Emeryville, CA (US)

(72) Inventors: Volker L. S. Kurz, Castro Valley, CA (US); Troy A. Lionberger, Berkeley, CA (US); Eric K. Sackmann, Oakland, CA (US); Kai W. Szeto, Emeryville, CA (US); Paul M. Lebel, San Mateo, CA (US); Brandon R. Bruhn, San Francisco, CA (US); Keith J. Breinlinger, San Rafael, CA (US); Eric D. Hobbs, Livermore, CA (US); Andrew W. McFarland, Berkeley, CA (US); J. Tanner Nevill, El Cerrito, CA (US); Xiaohua Wang, Albany, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 241 days.

(21) Appl. No.: 16/010,176

(22) Filed: Jun. 15, 2018

(65) Prior Publication Data
US 2018/0298318 A1    Oct. 18, 2018

Related U.S. Application Data

(63) Continuation of application No. PCT/US2016/069249, filed on Dec. 29, 2016.
(Continued)

(51) Int. Cl.
*B01L 3/00* (2006.01)
*C12M 3/06* (2006.01)
(Continued)

(52) U.S. Cl.
CPC ....... *C12M 23/16* (2013.01); *B01L 3/502761* (2013.01); *C12M 23/20* (2013.01);
(Continued)

(58) Field of Classification Search
CPC . C12M 23/16; B01L 3/502761; B01L 3/5027; B01L 3/502; B01L 3/50
(Continued)

(56) References Cited

U.S. PATENT DOCUMENTS

2004/0032793 A1   2/2004  Falcon
2004/0086870 A1   5/2004  Tyvoll et al.
(Continued)

FOREIGN PATENT DOCUMENTS

EP    1065378 B1    4/2002
JP    2011000079 A  1/2011
(Continued)

OTHER PUBLICATIONS

European Patent Office, Office Action, Application 16882668.3-1101, dated Jan. 4, 2020 (6 pages).
(Continued)

*Primary Examiner* — Christine T Mui
(74) *Attorney, Agent, or Firm* — Kenneth E. Horton; Kirton McConkie

(57) ABSTRACT

Apparatuses and methods are described for the use of optically driven bubble, convective and displacing fluidic flow to provide motive force in microfluidic devices. Alternative motive modalities are useful to selectively dislodge and displace micro-objects, including biological cells, from a variety of locations within the enclosure of a microfluidic device.

21 Claims, 30 Drawing Sheets

Related U.S. Application Data

(60) Provisional application No. 62/428,539, filed on Dec. 1, 2016, provisional application No. 62/314,889, filed on Mar. 29, 2016, provisional application No. 62/273,104, filed on Dec. 30, 2015.

(51) Int. Cl.
*C12M 1/00* (2006.01)
*C12M 1/26* (2006.01)

(52) U.S. Cl.
CPC ...... *C12M 33/12* (2013.01); *B01L 2200/0668* (2013.01); *B01L 2300/1822* (2013.01); *B01L 2400/0415* (2013.01); *B01L 2400/0427* (2013.01); *B01L 2400/0442* (2013.01); *B01L 2400/0454* (2013.01); *B01L 2400/086* (2013.01)

(58) Field of Classification Search
USPC .................................................. 422/502, 50
See application file for complete search history.

(56) References Cited

U.S. PATENT DOCUMENTS

| | | |
|---|---|---|
| 2006/0177350 A1 | 8/2006 | Sano et al. |
| 2007/0292312 A1 | 12/2007 | Bachman et al. |
| 2007/0292941 A1 | 12/2007 | Handique et al. |
| 2009/0021728 A1 | 1/2009 | Heinz et al. |
| 2010/0173393 A1 | 7/2010 | Handique et al. |
| 2011/0003325 A1 | 1/2011 | Durack |
| 2011/0030808 A1 | 2/2011 | Chiou et al. |
| 2012/0009671 A1 | 1/2012 | Hansen et al. |
| 2012/0015347 A1 | 1/2012 | Singhal et al. |
| 2012/0315203 A1 | 12/2012 | Baroud et al. |
| 2014/0116881 A1 | 5/2014 | Chapman et al. |
| 2015/0064702 A1 | 3/2015 | Handique et al. |
| 2015/0151298 A1 | 6/2015 | Hobbs et al. |
| 2015/0165436 A1 | 6/2015 | Chapman et al. |

FOREIGN PATENT DOCUMENTS

| | | | |
|---|---|---|---|
| WO | 2001035071 A3 | 2/2002 | |
| WO | WO 2014/070873 | * 5/2014 | ............. G01N 35/08 |
| WO | 2015061497 A1 | 4/2015 | |

OTHER PUBLICATIONS

Debar et al., Fabrication and performance testing of a steady thermocapillary pump with no moving parts, Proceedings of the MEMS 2002 IEEE International Conference Las Vegas, NV, USA, 109-112. (Jan. 20-24, 2002).

Hua et al., Microfluidic Actuation Using Electrochemically Generated Bubbles, Anal. Chem. 74:6392-9 (2002).

Leu et al., Design and Fabrication of Thermocapillary Micro Bubble Pump, Advanced Materials Research 528:23-26 (2012).

Liu et al., Optofluidic control using photothermal nanoparticles, Nature Materials 5:27-32 (2006). Dec. 18, 2005.

Vercruysse et al., "A High Speed Miniaturized Cell Sorter with Lens-Free Imaging and Thermal Bubble Based Jet Flow Sorting", 18th Intl Conference on Miniaturized Systems for Chemistry and Life Sciences, Oct. 26-30, 2014.

Z Report_The International Search Report and the Written Opinion of the International Searching Authority, PCT Application Serial No. PCT/US201069249 (dated Apr. 28, 2017), 14 pages.

Zhang et al., Laser-induced thermal bubbles for microfluidics applications, Lab on a chip 11:1389-X (2011).

Knopf, G.K. Chapter 1: Light-Driven and Optically Actuated Technologies, Optical Nano and Micro Technology, CRC Press, Nov. 26, 2012 section 1.5.

* cited by examiner

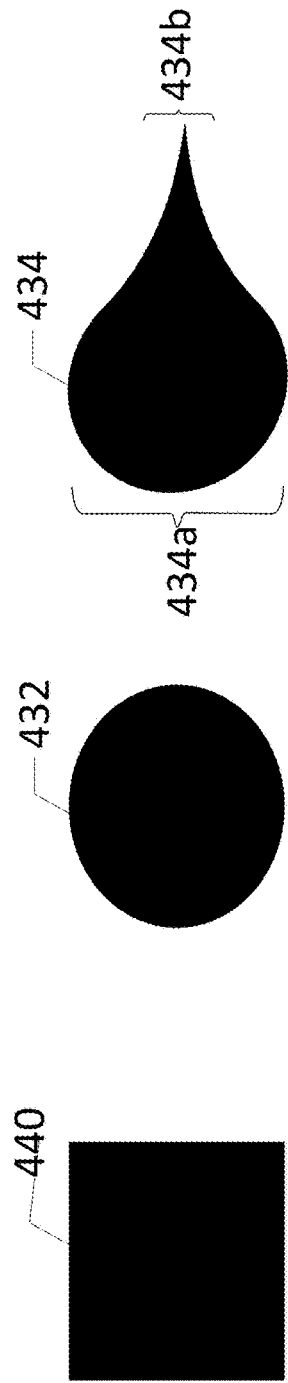
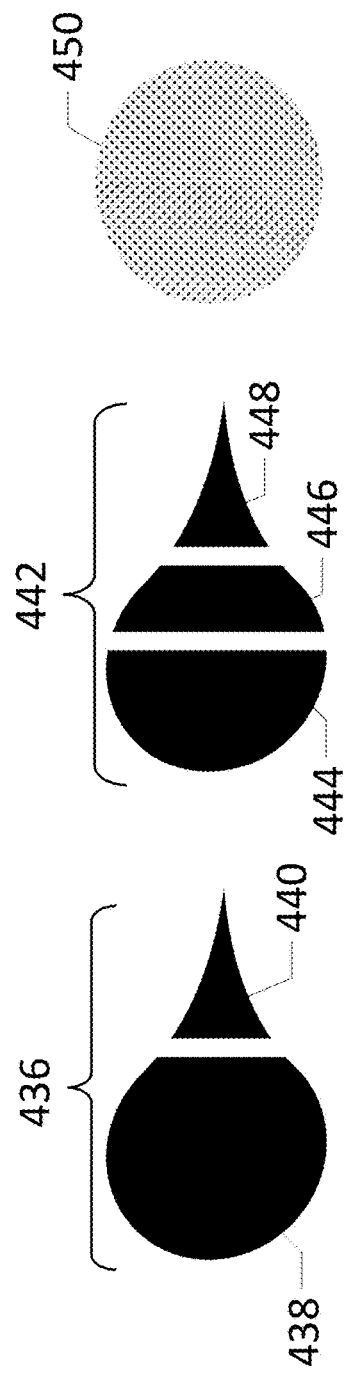
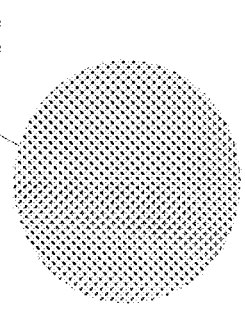
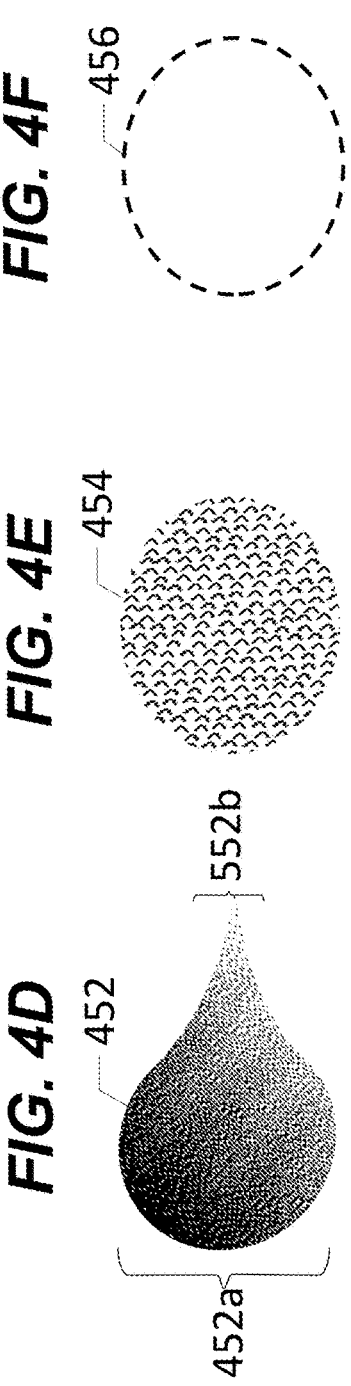
FIG. 4A — FIG. 4I

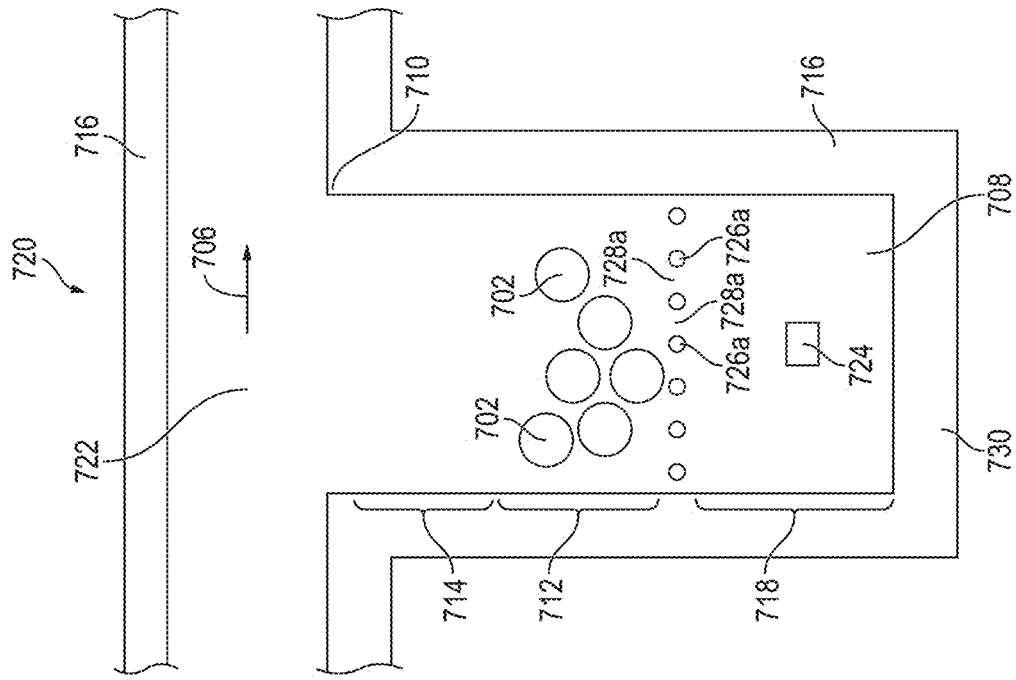
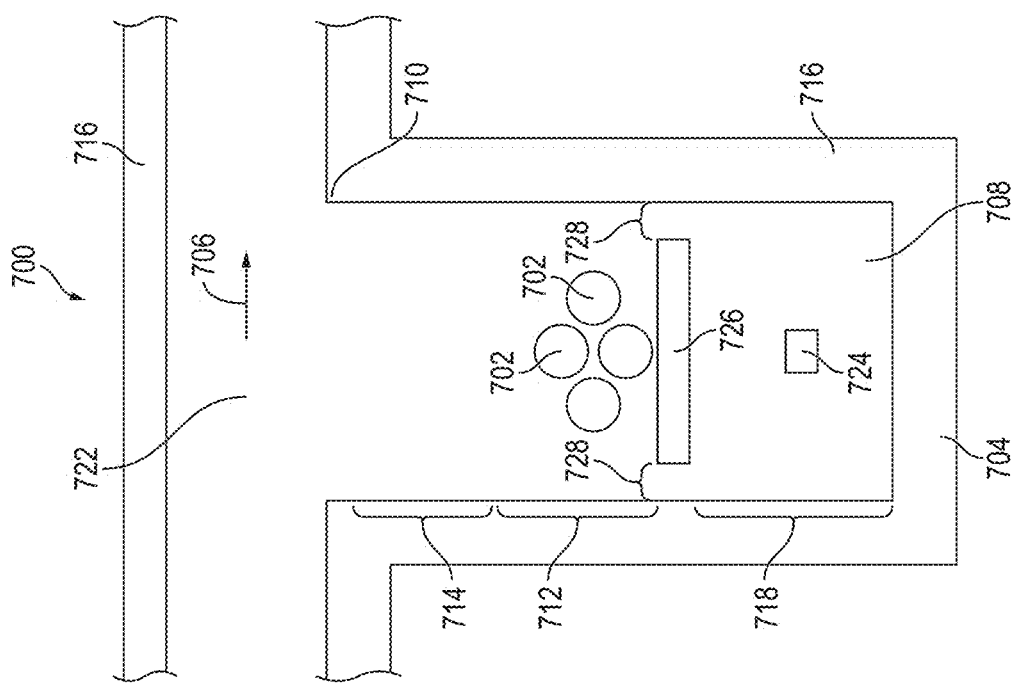
FIG. 7A
FIG. 7B

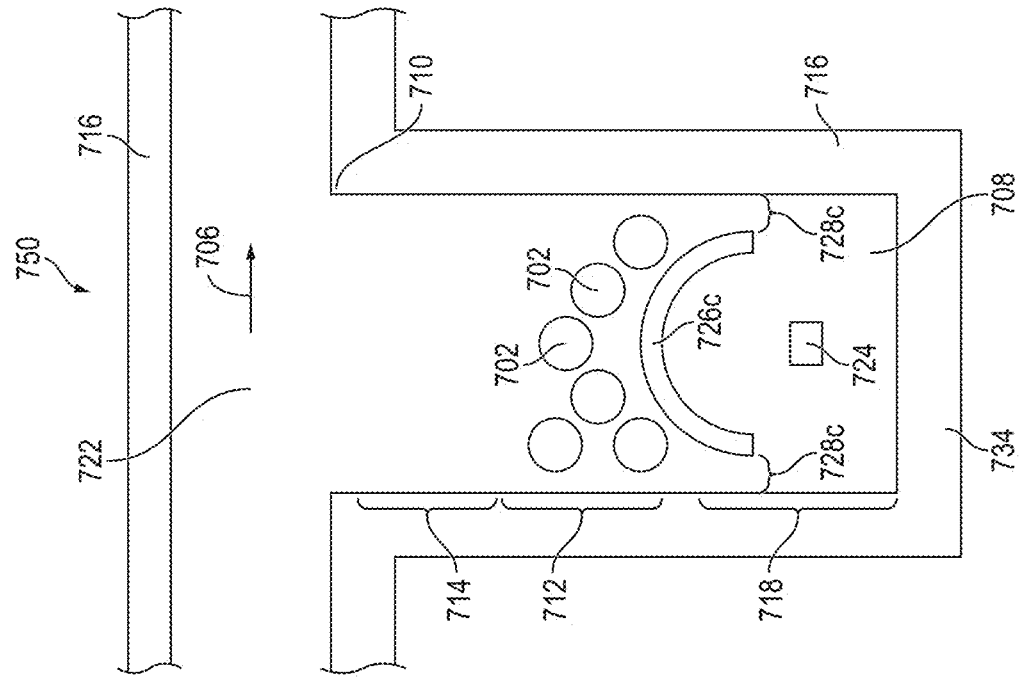
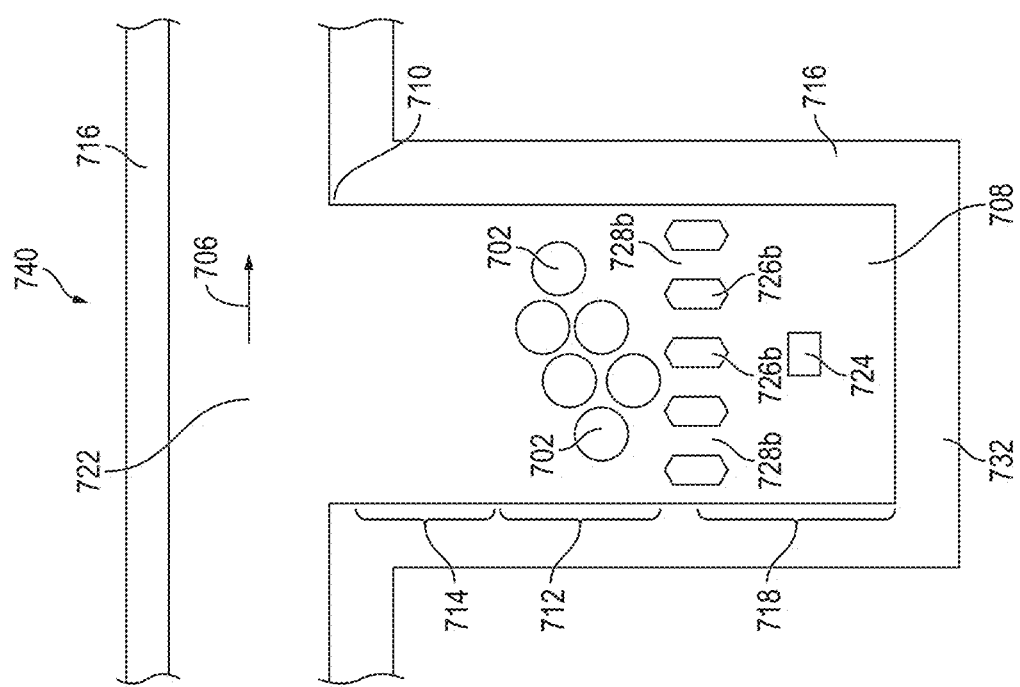
FIG. 7D
FIG. 7C

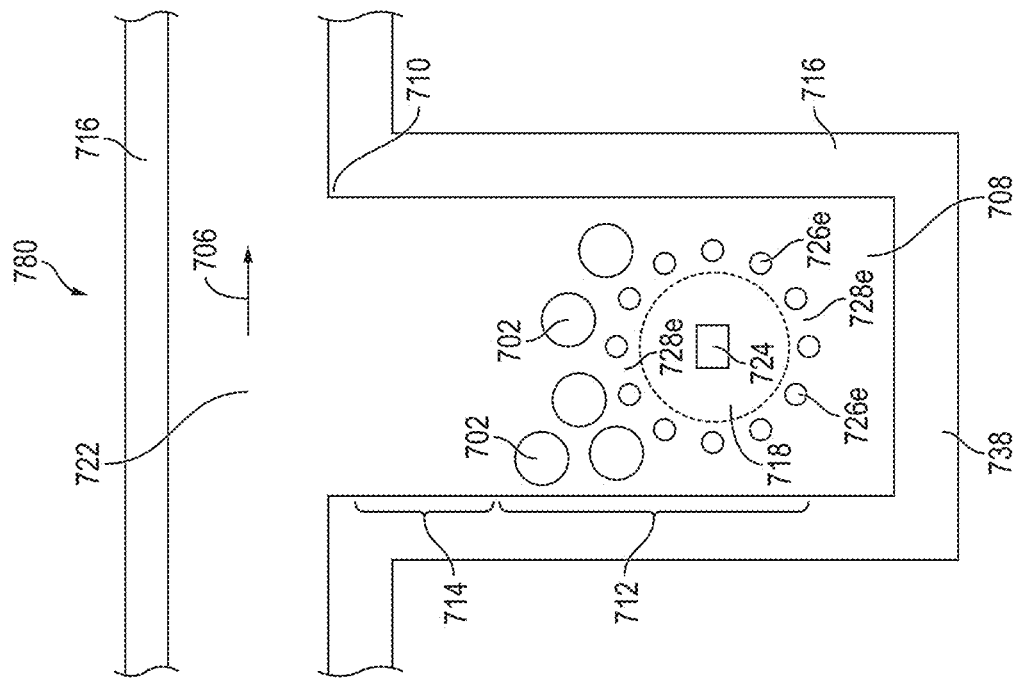
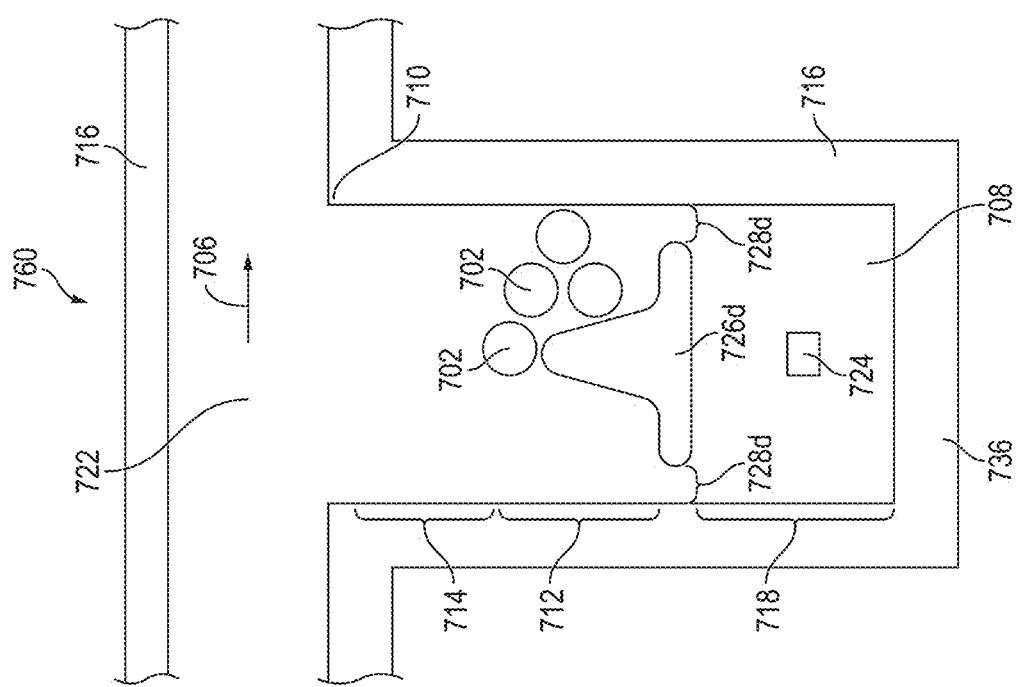

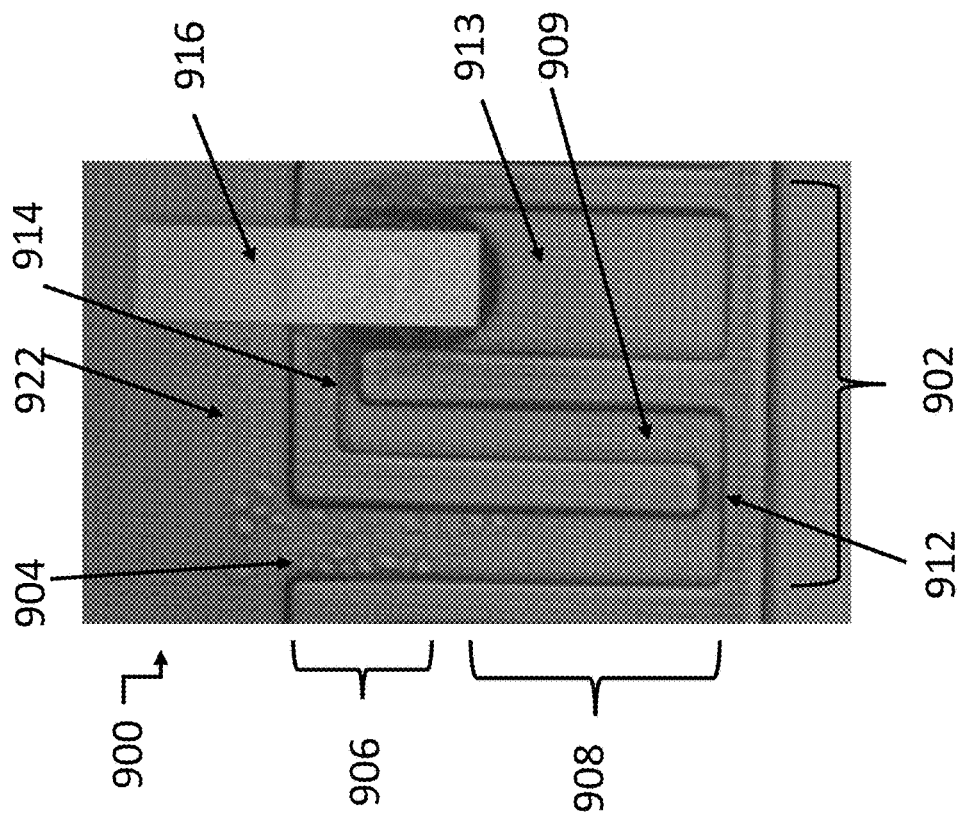
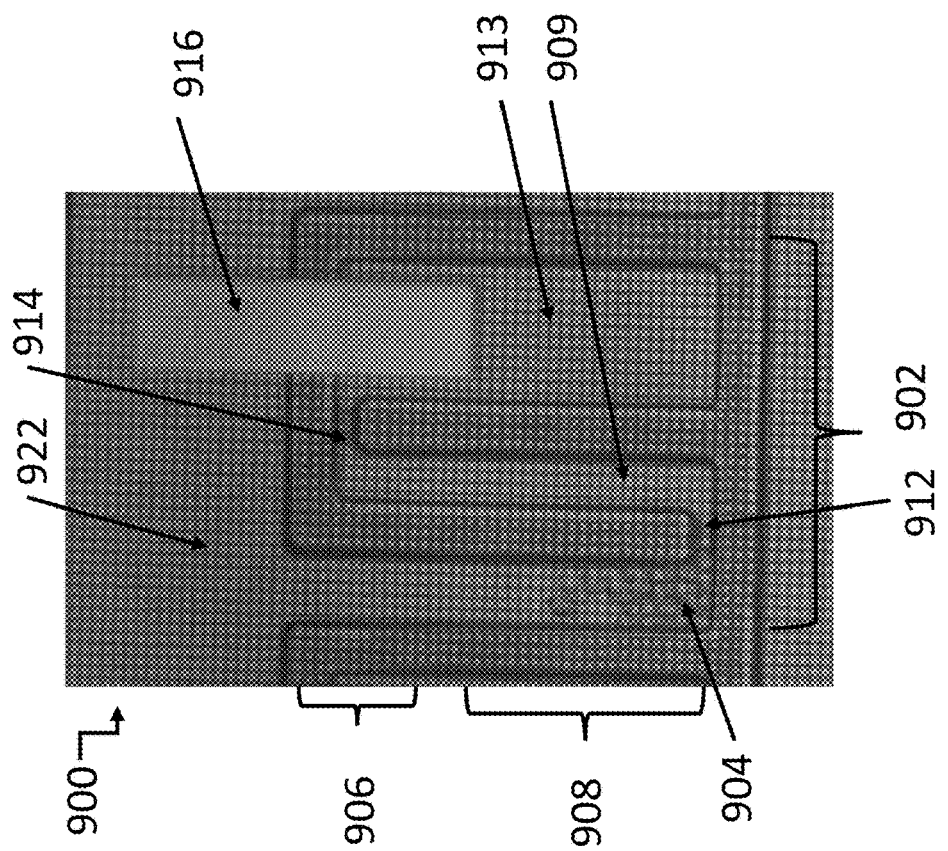
FIG. 9B
FIG. 9A

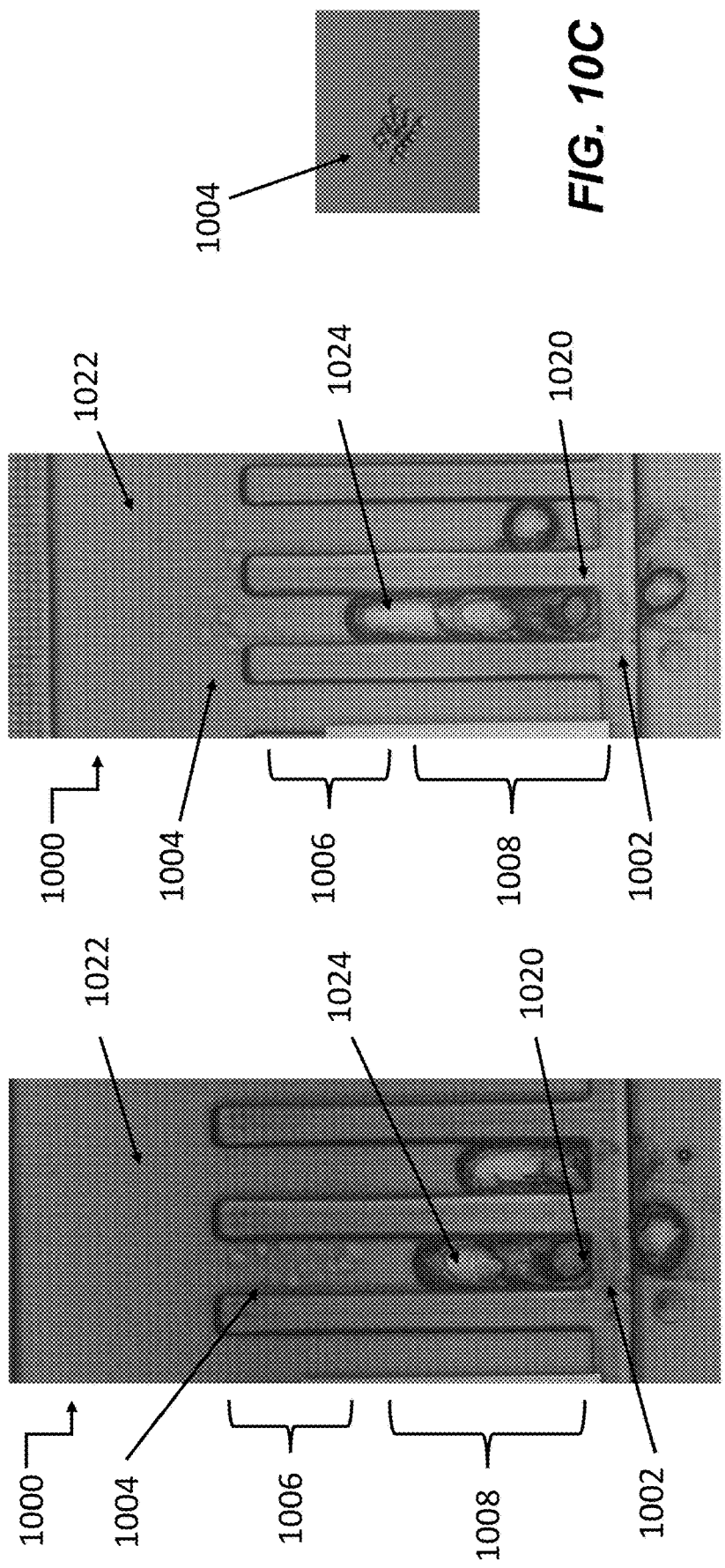

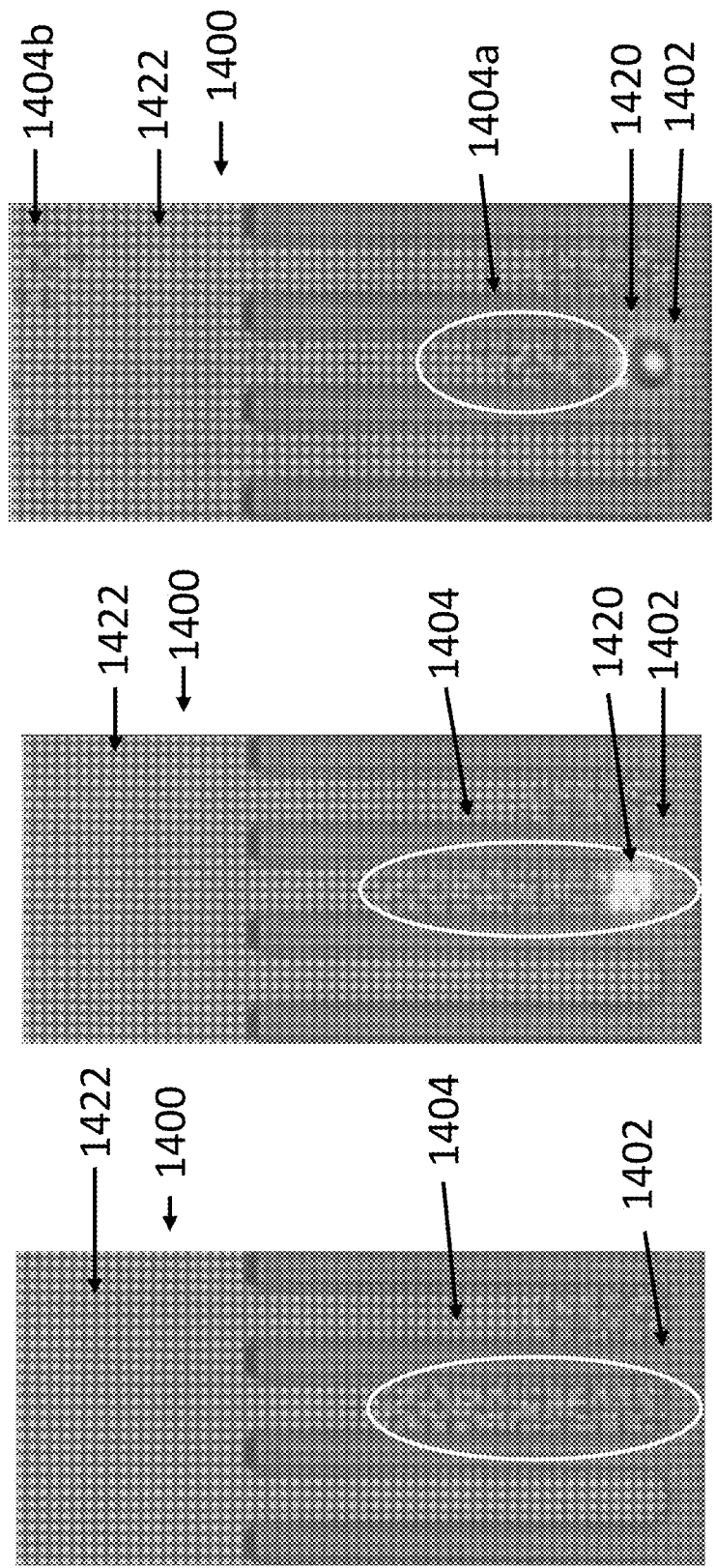

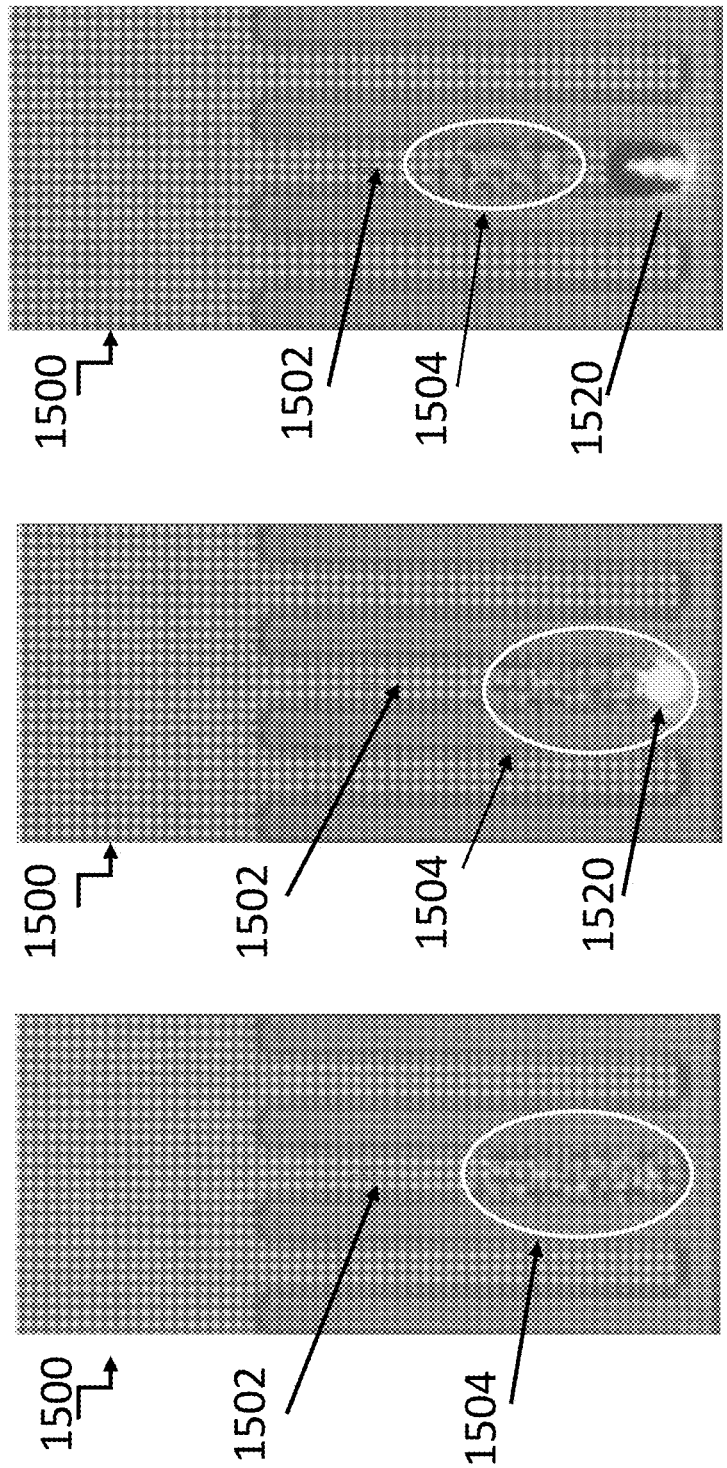

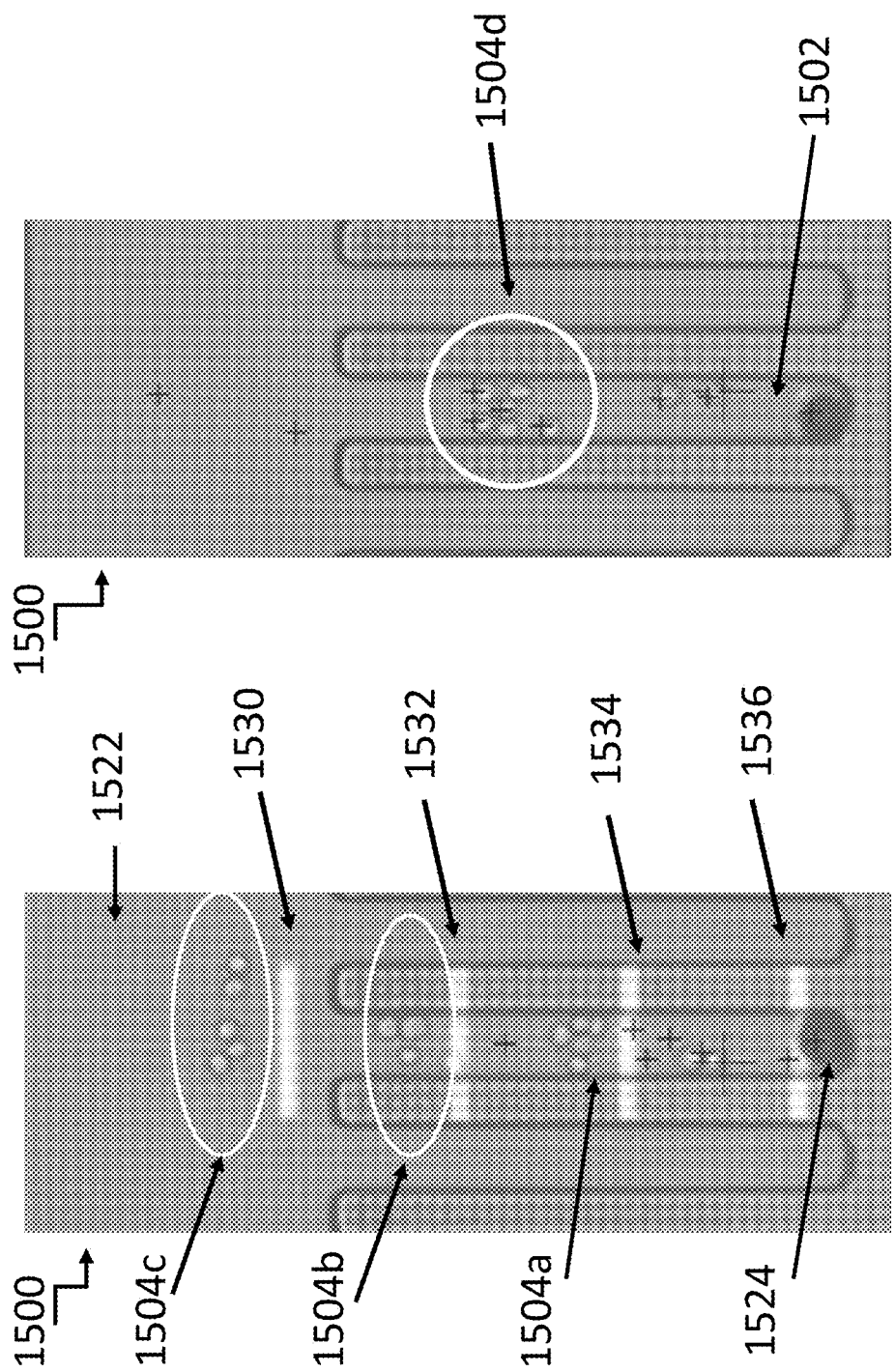

MICROFLUIDIC DEVICES FOR OPTICALLY-DRIVEN CONVECTION AND DISPLACEMENT, KITS AND METHODS THEREOF

This application is a non-provisional application claiming the benefit under 35 U.S.C. 119(e) of U.S. Provisional Application No. 62/273,104, filed on Dec. 30, 2015; U.S. Provisional Application No. 62/314,889, filed on Mar. 29, 2016; and of U.S. Provisional Application No. 62/428,539, filed on Dec. 1, 2016, each of which disclosures is herein incorporated by reference in its entirety.

BACKGROUND

As the field of microfluidics develops, microfluidic devices have become convenient platforms for processing and manipulating micro-objects such as biological cells. Some embodiments of the present invention are directed to methods and devices for the use of optically driven bubble, convective and displacing fluidic flow to provide motive force in microfluidic devices.

SUMMARY

In one aspect, a microfluidic device is provided, where the microfluidic device includes an enclosure having a flow region and a sequestration pen, where the sequestration pen includes: a connection region, an isolation region and a displacement force generation region, where: the connection region includes a proximal opening to the flow region and a distal opening to the isolation region; and the isolation region includes at least one fluidic connection to the displacement force generation region; and the displacement force generation region further includes a thermal target.

In another aspect, a microfluidic device is provided, where the microfluidic device includes an enclosure having a microfluidic circuit configured to contain a fluidic medium, where the microfluidic circuit is configured to accommodate at least one cyclic flow of the fluidic medium; and a first thermal target disposed on a surface of the enclosure within the microfluidic circuit, where the first thermal target is configured to produce a first cyclic flow of the fluidic medium upon optical illumination.

In yet another aspect, a microfluidic device is provided, where the microfluidic device includes an enclosure having a microfluidic channel and a sequestration pen, and further where the sequestration pen is adjacent to and opens off of the microfluidic channel and a thermal target is disposed in the channel adjacent to an opening to a sequestration pen, and wherein the thermal target is further configured to direct a flow of the fluidic medium into the sequestration pen upon optical illumination.

In another aspect, a kit for culturing micro-objects is provided, where the kit includes: a microfluidic device as described herein; and, one or more reagents configured to provide at least one coated surface within an enclosure of the microfluidic device.

In another aspect, a method is provided for dislodging one or more micro-objects within a microfluidic device, the method including the steps of: illuminating a selected discrete region containing or adjacent to one or more micro-objects disposed within a fluidic medium in an enclosure of the microfluidic device, wherein the enclosure includes a microfluidic circuit including a flow region and a substrate; and maintaining the illumination of the selected discrete region of a first period of time sufficient to generate a dislodging force, dislodging the one or more micro-objects from the surface.

In yet another aspect, a method is provided for mixing fluidic media, and/or micro-objects contained therein, within an enclosure of a microfluidic device, the method including: focusing a light source on a thermal target disposed on a surface of the enclosure within a microfluidic circuit including at least one fluidic medium and/or micro-objects, thereby heating a first portion of the at least one fluidic medium; and inducing a cyclic flow of the at least one fluidic medium within the microfluidic circuit thereby mixing the fluidic media and/or micro-objects disposed therein.

BRIEF DESCRIPTION OF THE DRAWINGS

FIGS. 4A-4I are graphical representations of various thermal targets according to embodiments of the disclosure.

FIGS. 7A-7F are graphical representations of further embodiments of sequestration pens according to the disclosure.

FIGS. 9A-9D are photographic representations of the use of optically-driven forces used to export cells from a sequestration pen according to some embodiments of the disclosure, and viability thereafter.

FIGS. 10A-10C depict the use of optically driven displacement to export cells from a sequestration pen and viability thereafter.

FIGS. 14A-14C are photographic representations of one embodiment of the method of laser illumination for dislodging micro-objects.

FIGS. 15A-15E are photographic representations of another embodiment of the method of laser illumination for dislodging micro-objects.

DETAILED DESCRIPTION OF EXEMPLARY EMBODIMENTS

Figure 1A:
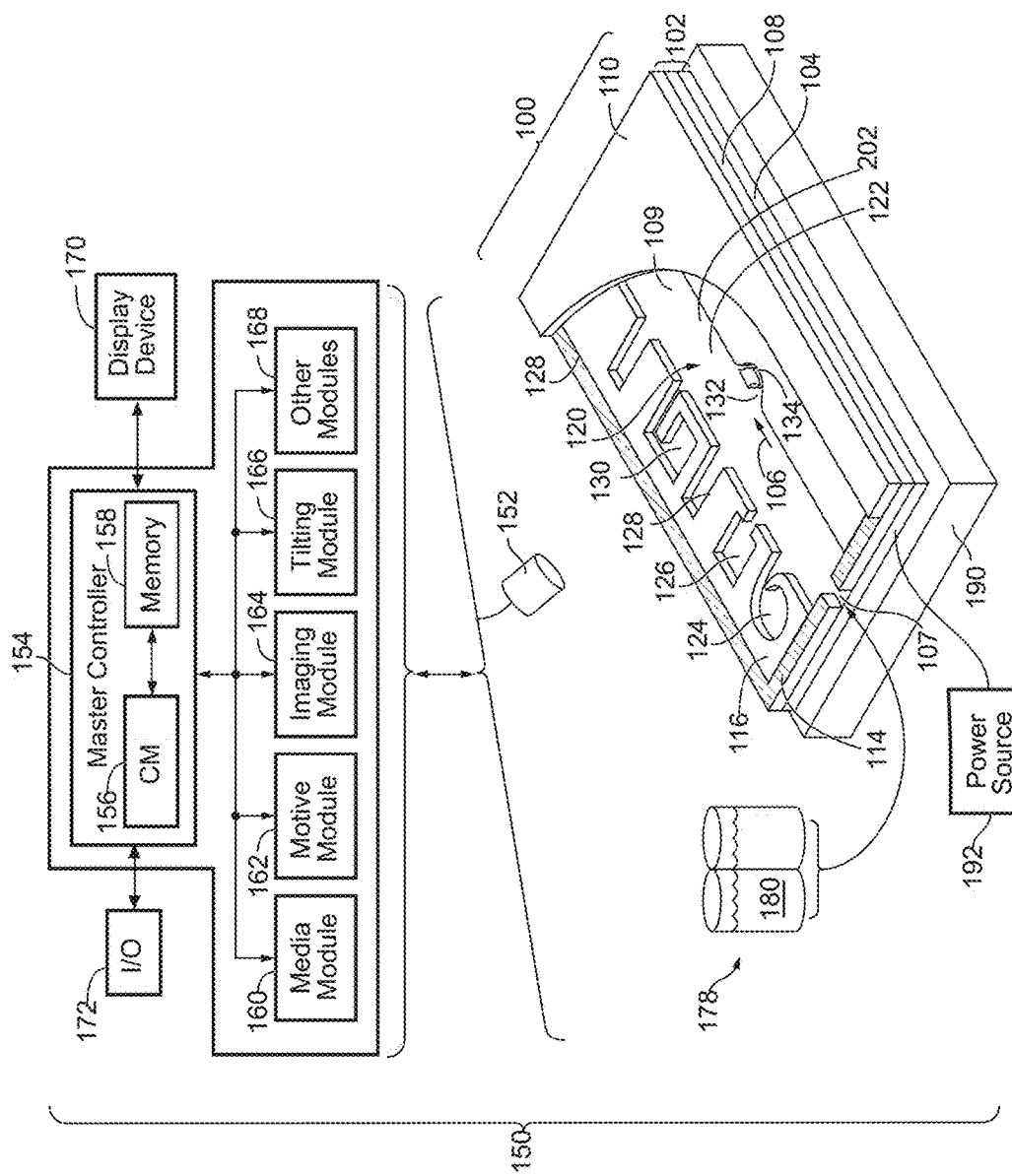
FIG. 1A is a graphical representation of a system for use with a microfluidic device and associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 microliters. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 microliters. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 microliter, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations:

curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, the connection region and the isolation region of a microfluidic sequestration pen.

As used herein, the term "constriction" refers generally to a narrowing of a width of a circuit element (or an interface between two circuit elements) in a microfluidic device. The constriction can be located, for example, at the interface between the isolation region and the connection region of a microfluidic sequestration pen of the instant disclosure.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device. The micro-object may still be capable of motion within an in situ-generated capture structure.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "sacrificial feature" refers to a microfluidic circuit element which may be used as a thermal target in the microfluidic devices and methods of the disclosure, and which is at least partially destroyed upon being sufficiently illuminated so as to generate a bubble, a cavitating force, or a shear flow as described herein.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices.

FIG. 1A illustrates an example of a microfluidic device 100 and a system 150 which can be used for generation of embryos in vitro, including selecting and evaluating ova and/or oocytes and/or sperm. A perspective view of the microfluidic device 100 is shown having a partial cut-away of its cover 110 to provide a partial view into the microfluidic device 100. The microfluidic device 100 generally includes a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens include various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as including a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each including a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can include one or more electrodes (not shown) and a substrate or a plurality of interconnected substrates. For example, the support structure 104 can include one or more semiconductor substrates, each of which is electrically connected to an electrode (e.g., all or a subset of the semiconductor substrates can be electrically connected to a single electrode). The support structure 104 can further include a printed circuit board assembly ("PCBA"). For example, the semiconductor substrate(s) can be mounted on a PCBA.

The microfluidic circuit structure 108 can define circuit elements of the microfluidic circuit 120. Such circuit elements can include spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 includes a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device 194 (incorporated within imaging module 164, where device 194 is not illustrated in FIG. 1A, per se), and a tilting device 190 (part of tilting module 166, where device 190 is not illustrated in FIG. 1A).

The electrical power source 192 can provide electric power to the microfluidic device 100 and/or tilting device 190, providing biasing voltages or currents as needed. The electrical power source 192 can, for example, include one or more alternating current (AC) and/or direct current (DC) voltage or current sources. The imaging device 194 (part of imaging module 164, discussed below) can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can include a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can include a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as including a microfluidic channel 122 and sequestration pens 124, 126, 128, 130. Each pen includes an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may include any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful in producing an embryo, such as isolating one ovum from an adjacent ovum. Testing, stimulating and fertilizing may all be performed on an individual basis and, in some embodiments, may be performed on an individual time scale. In some embodiments, the microfluidic circuit 120 comprises a plurality of identical microfluidic sequestration pens.

In some embodiments, the microfluidic circuit 120 comprises a plurality of microfluidic sequestration pens, wherein two or more of the sequestration pens comprise differing structures and/or features which provide differing benefits in producing embryos. One non-limiting example may include maintaining ova in one type of pen while maintaining sperm in a different type of pen. In another embodiment, at least one of the sequestration pens is configured to have electrical contacts suitable for providing electrical activation for an ovum. In yet another embodiment, differing types of cells (such as, for example, uterine cells, endometrial cells, PEG (intercalary) cells derived from the uterine tube (e.g., oviduct or Fallopian tube), cumulus cells, or a combination thereof) may be disposed in sequestration pens adjacent to a sequestration pen containing an ovum, such that secretions from the surrounding sequestration pens may diffuse out of each respective pen and into the pen containing an ovum, which is not possible with macroscale in-vitro culturing and fertilization. Microfluidic devices useful for producing an embryo may include any of the sequestration pens 124, 126, 128, and 130 or variations thereof, and/or may include pens configured like those shown in FIGS. 2B, 2C, 2D, 2E and 2F, as discussed below.

In the embodiment illustrated in FIG. 1A, a single channel 122 and flow path 106 is shown. However, other embodiments may contain multiple channels 122, each configured to include a flow path 106. The microfluidic circuit 120 further includes an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 includes a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further includes one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further include an opening which is configured to assist the flow of targeted micro-objects into the traps 132. In some instances, the traps 132 include an opening having a height and width that is approximately equal to the dimensions of a single target micro-object, whereby larger micro-objects are prevented from entering into the micro-object trap. The traps 132 may further include other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 includes a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and microobjects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
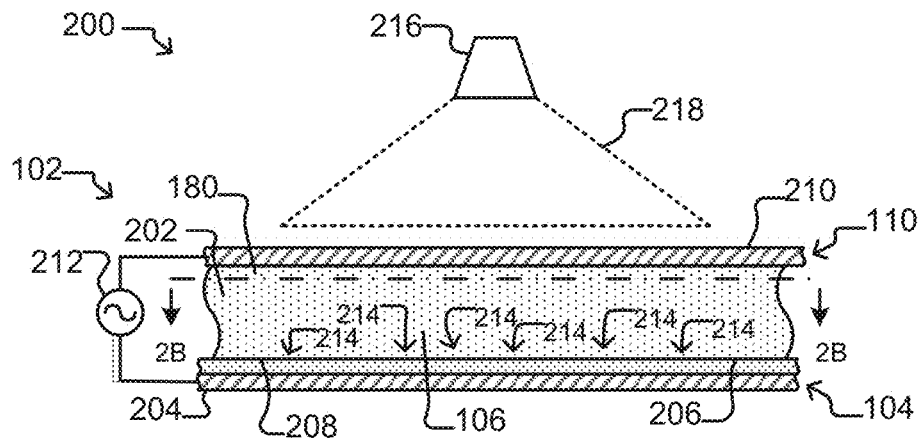
FIGS. 1B and 1C are graphical representations of a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which oocytes, ova, or embryos can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic Device Motive Configurations.

As described above, the control and monitoring equipment of the system can include a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
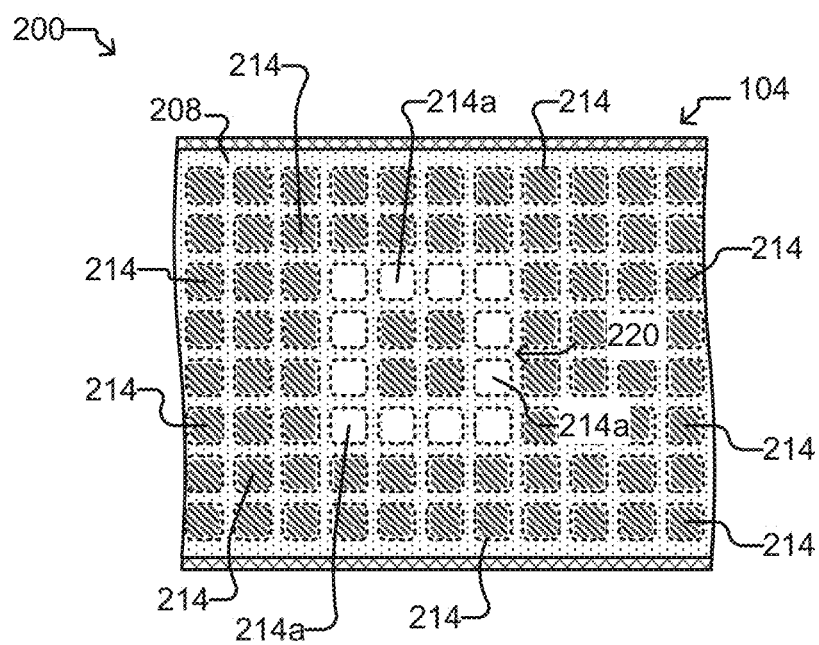

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 204, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration pens. Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can include a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

Figure 2A:
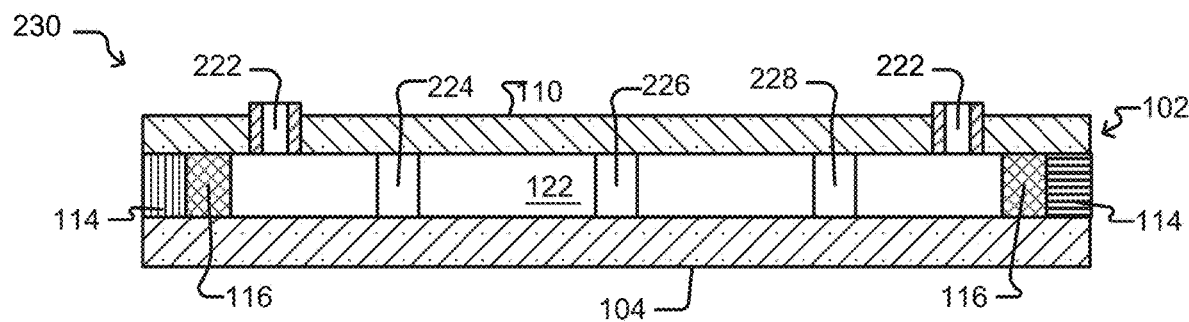
FIGS. 2A and 2B are graphical representations of isolation pens according to some embodiments of the disclosure.
Figure 2B:
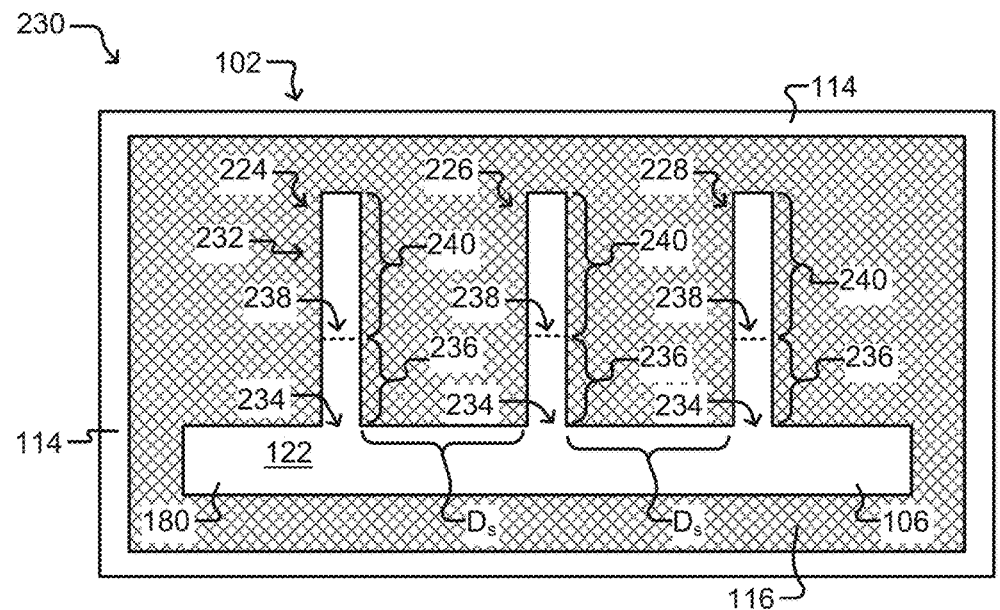
Figure 2C:
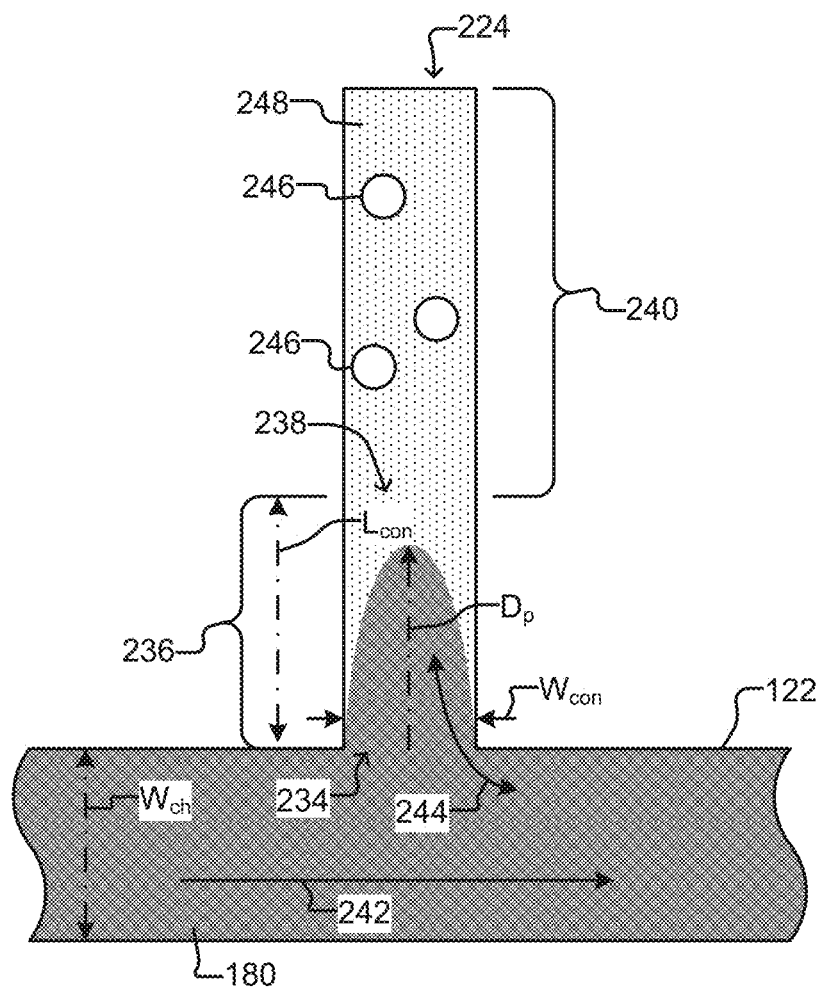
FIG. 2C is a graphical representation of a detailed sequestration pen according to some embodiments of the disclosure.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290, 320, 400, 450, 500, 700 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be in any of the ranges identified herein for the width W the connection region con of 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be in any of the ranges identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
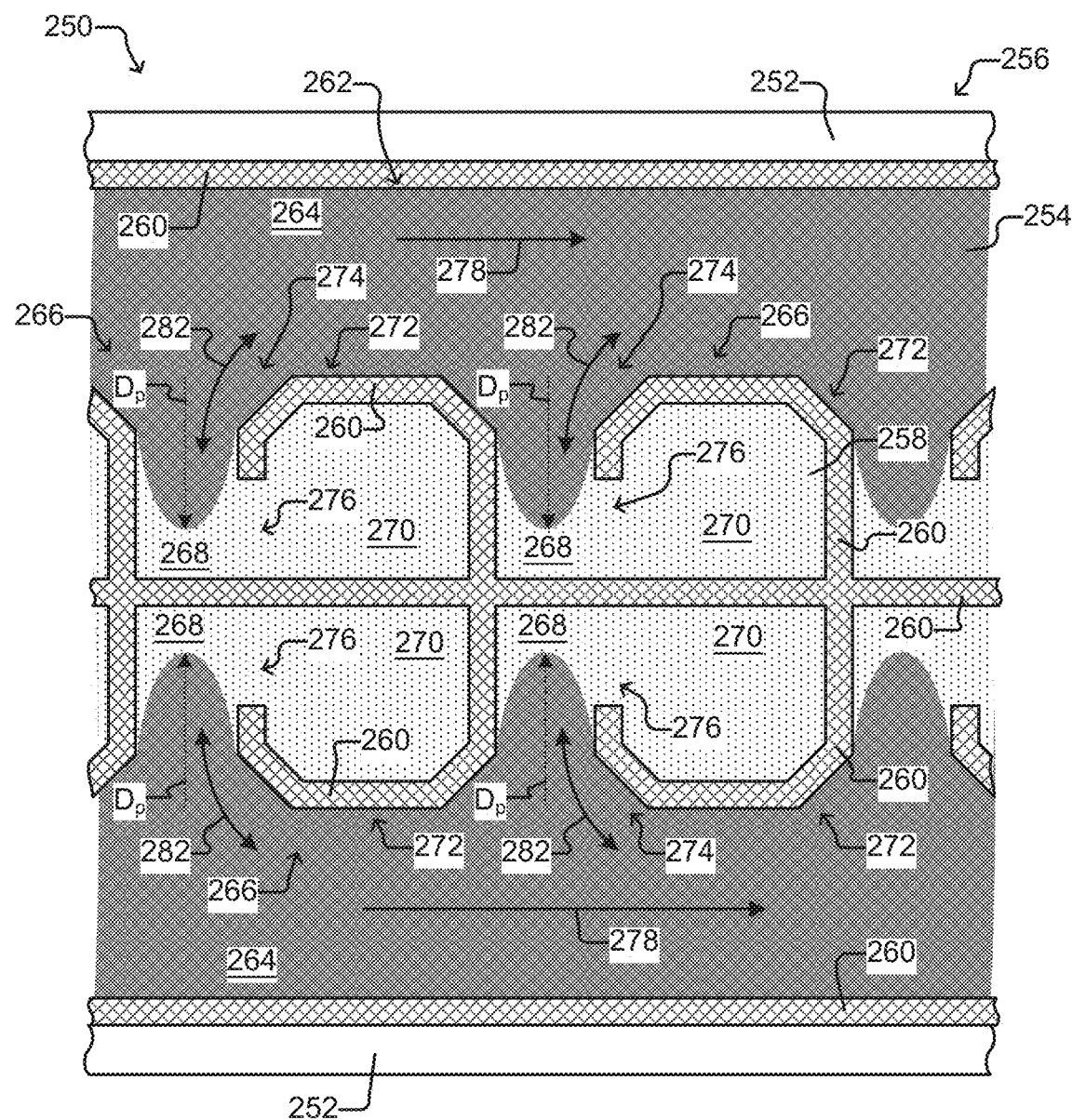
FIGS. 2D-F are graphical representations of sequestration pens according to some other embodiments of the disclosure.
Figure 2E:
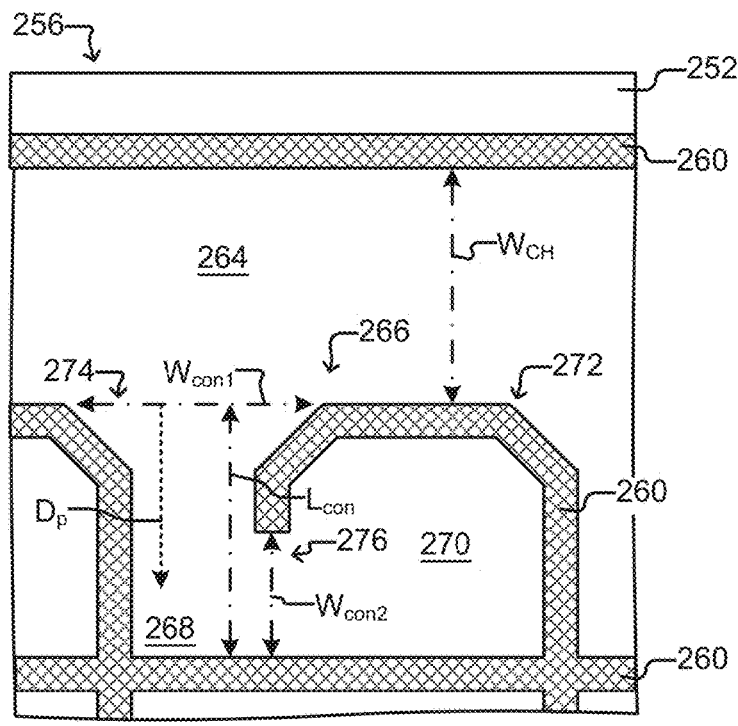
Figure 2F:
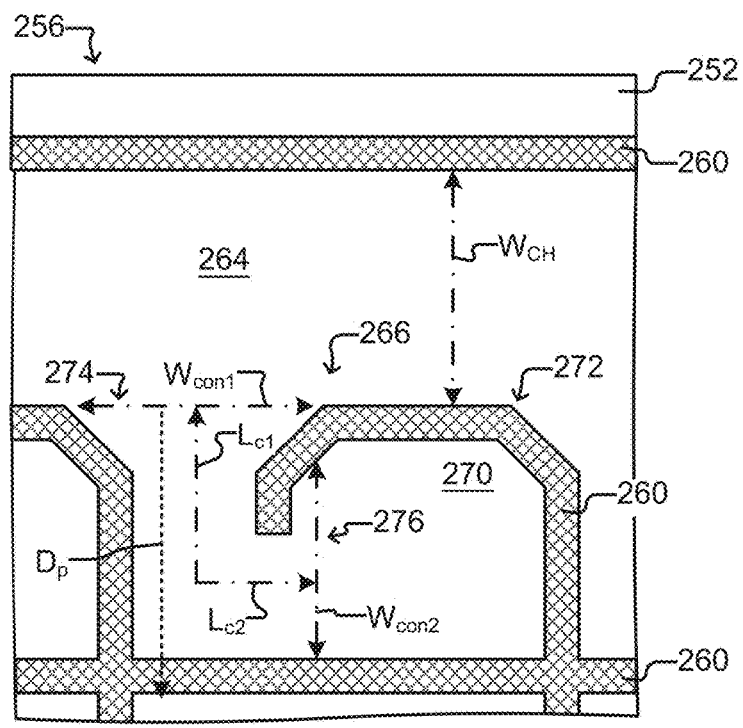

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 250, 280, 290, 500, 550, 560, 600, 620, 640, 670, 700, 720, 720, 750, 760, 780, 808, 810, 812, 900, 1000, 1100, 1200, 1300, 1400, 1500. Likewise, the microfluidic device 250 is another variant of the microfluidic device 100, and may also have the same or a different DEP configuration as the above-described microfluidic device 100, 200, 230, 250, 280, 290, 500, 550, 560, 600, 620, 640, 670, 700, 720, 720, 750, 760, 780, 808, 810, 812, 900, 1000, 1100, 1200, 1300, 1400, 1500 as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can include multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles in any of the following ranges: from about 30° to about 90°, from about 45° to about 90°, from about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the microfluidic channel (e.g., 122) at a proximal opening (e.g. 234) can be within any of the following ranges: about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. In some other embodiments, the width $W_{ch}$ of the microfluidic channel (e.g., 122) at a proximal opening (e.g. 234) can be in a range of about 200-800 microns, 200-700 microns, or 200-600 microns. The foregoing are examples only, and the width $W_{ch}$ of the microfluidic channel 122 can be in other ranges (e.g., a range defined by any of the endpoints listed above). Moreover, the $W_{ch}$ of the microfluidic channel 122 can be selected to be in any of these ranges in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1 \times 10^4$-$3 \times 10^6$ square microns, $2 \times 10^4$-$2 \times 10^6$ square microns, $4 \times 10^4$-$1 \times 10^6$ square microns, $2 \times 10^4$-$5 \times 10^5$ square microns, $2 \times 10^4$-$1 \times 10^5$ square microns or about $2 \times 10^5$-$2 \times 10^6$ square microns.

In various embodiments of sequestration pens, the height $H_{ch}$ of the microfluidic channel (e.g., 122) at a proximal opening (e.g., 234) can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be in other ranges (e.g., a range defined by any of the endpoints listed above). The height $H_{ch}$ of the microfluidic channel 122 can be selected to be in any of these ranges in regions of the microfluidic channel other than at a proximal opening of an sequestration pen.

In various embodiments of sequestration pens a cross-sectional area of the microfluidic channel (e.g., 122) at a proximal opening (e.g., 234) can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be in other ranges (e.g., a range defined by any of the endpoints listed above).

In various embodiments of sequestration pens, the length $L_{con}$ of the connection region (e.g., 236) can be in any of the following ranges: about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in a different range than the foregoing examples (e.g., a range defined by any of the endpoints listed above).

In various embodiments of sequestration pens the width $W_{con}$ a connection region (e.g., 236) at a proximal opening (e.g., 234) can be in any of the following ranges 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{con}$ of a connection region (e.g., 236) at a proximal opening (e.g., 234) can be at least as large as the largest dimension of a micro-object (e.g., biological cell which may be a T cell, B cell, or an ovum or embryo) that the sequestration pen is intended for. For example, the width $W_{con}$ of a connection region 236 at a proximal opening 234 of an sequestration pen that an oocyte, ovum, or embryo will be placed into can be in any of the following ranges: about 100 microns, about 110 microns, about 120 microns, about 130 microns, about 140 microns, about 150 microns, about 160 microns, about 170 microns, about 180 microns, about 190 microns, about 200 microns, about 225 microns, about 250 microns, about 300 microns or about 100-400 microns, about 120-350 microns, about 140-300 microns, or about 140-200 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{pr}$ of a proximal opening of a connection region may be at least as large as the largest dimension of a micro-object (e.g., a biological micro-object such as a cell) that the sequestration pen is intended for. For example, the width $W_{pr}$ may be about 50 microns, about 60 microns, about 100 microns, about 200 microns, about 300 microns or may be in a range of about 50-300 microns, about 50-200 microns, about 50-100 microns, about 75-150 microns, about 75-100 microns, or about 200-300 microns In various embodiments of sequestration pens, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 can be different than the foregoing examples.

In various embodiments of microfluidic devices 100, 200, 230, 250, 280, 290, 500, 550, 560, 600, 620, 640, 670, 700, 720, 720, 750, 760, 780, 808, 810, 812, 900, 1000, 1100, 1200, 1300, 1400, 1500, $V_{max}$ can be set around 0.2, 0.3, 0.4, 0.5, 0.6, 0.7, 0.8, 0.9, 1.0, 1.1, 1.2, 1.3, 1.4, or 1.5 microliters/sec.

In various embodiments of microfluidic devices having sequestration pens, the volume of an isolation region (e.g., 240) of a sequestration pen can be, for example, at least $5 \times 10^5$, $8 \times 10^5$, $1 \times 10^6$, $2 \times 10^6$, $4 \times 10^6$, $6 \times 10^6$, $8 \times 10^6$, $1 \times 10^7$, $5 \times 10^7$, $1 \times 10^8$, $5 \times 10^8$, or $8 \times 10^8$ cubic microns, or more. In various embodiments of microfluidic devices having sequestration pens, the volume of a sequestration pen may be about $5 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, or about 1000 to about 3500 sequestration pens. The sequestration pens need not all be the same size and may include a variety of configurations (e.g., different widths, different features within the sequestration pen).

Figure 2G:
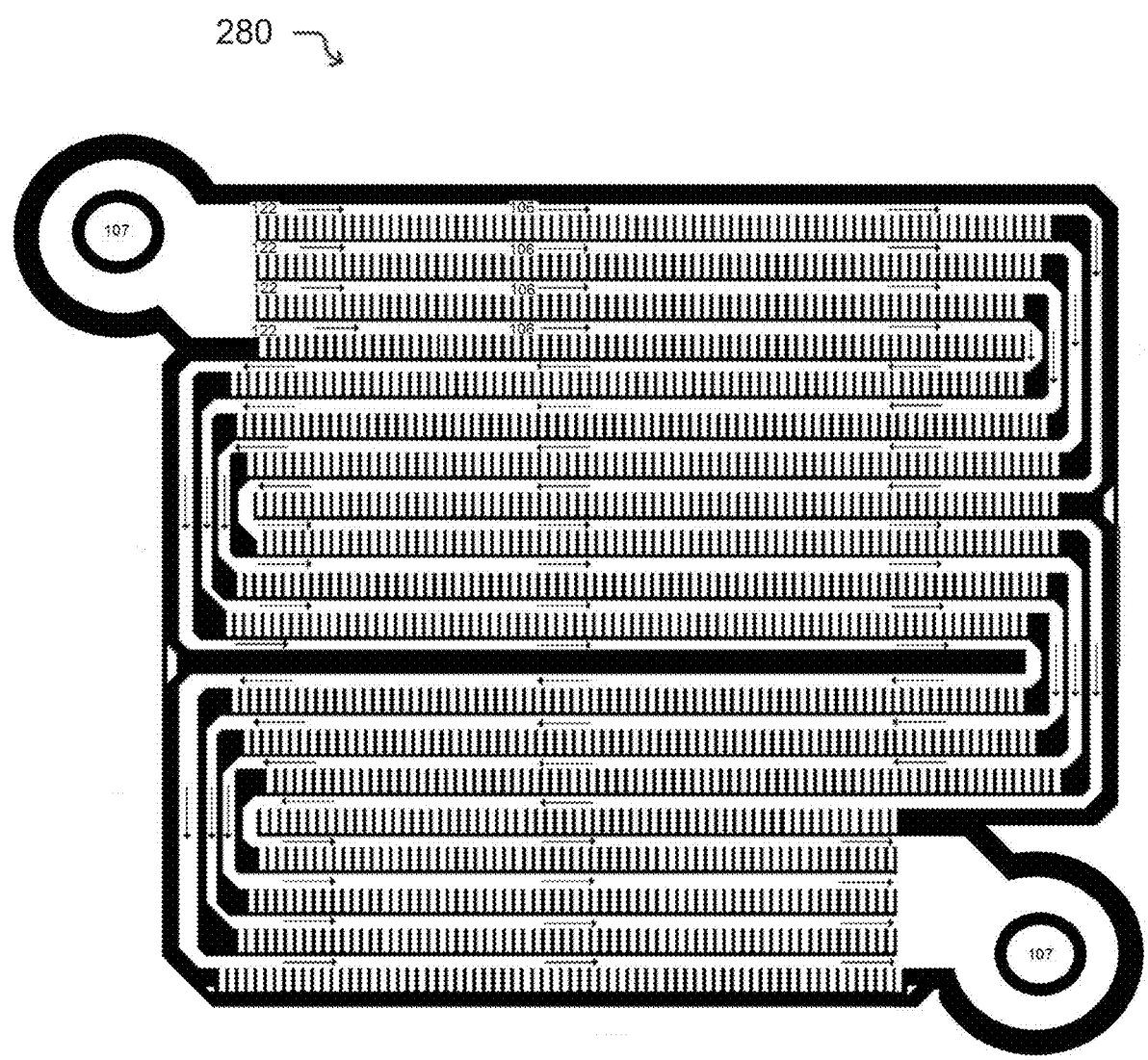
FIG. 2G is a graphical representation of a microfluidic device according to an embodiment of the disclosure.

FIG. 2G illustrates a microfluidic device 280 according to one embodiment. The microfluidic device 280 illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further includes a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Coating Solutions and Coating Agents.

Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating Agent/Solution.

Any convenient coating agent/coating solution can be used, including but not limited to: serum or serum factors, bovine serum albumin (BSA), polymers, detergents, enzymes, and any combination thereof.

Polymer-Based Coating Materials.

The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a range of from about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently Linked Coating Materials.

In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned Surface Properties.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface has a thickness in the range of about 1 nm to about 10 nm; about 1 nm to about 7 nm; about 1 nm to about 5 nm; or any individual value therebetween. In other embodiments, the conditioned surface formed by the covalently linked moieties may have a thickness of about 10 nm to about 50 nm. In various embodiments, the conditioned surface prepared as described herein has a thickness of less than 10 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). These values are in contrast to that of a CYTOP® (Asahi Glass Co., Ltd. JP) fluoropolymer spin coating, which has a thickness in the range of about 30 nm. In some embodiments, the conditioned surface does not require a perfectly formed monolayer to be suitably functional for operation within a DEP-configured microfluidic device.

In various embodiments, the coating material providing a conditioned surface of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-Part Conditioned Surface.

The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of Preparing a Covalently Linked Coating Material.

In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

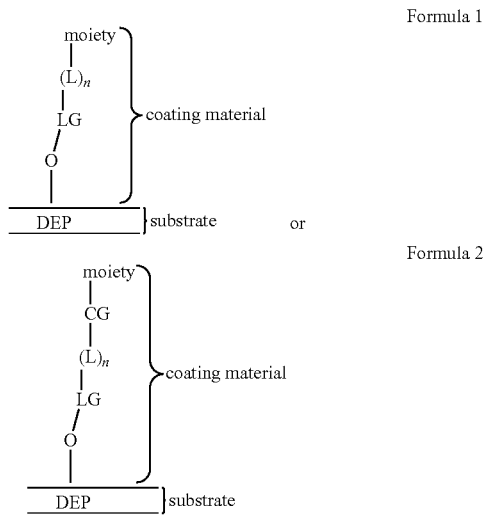

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group consisting of ether, amino, carbonyl, amido, or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
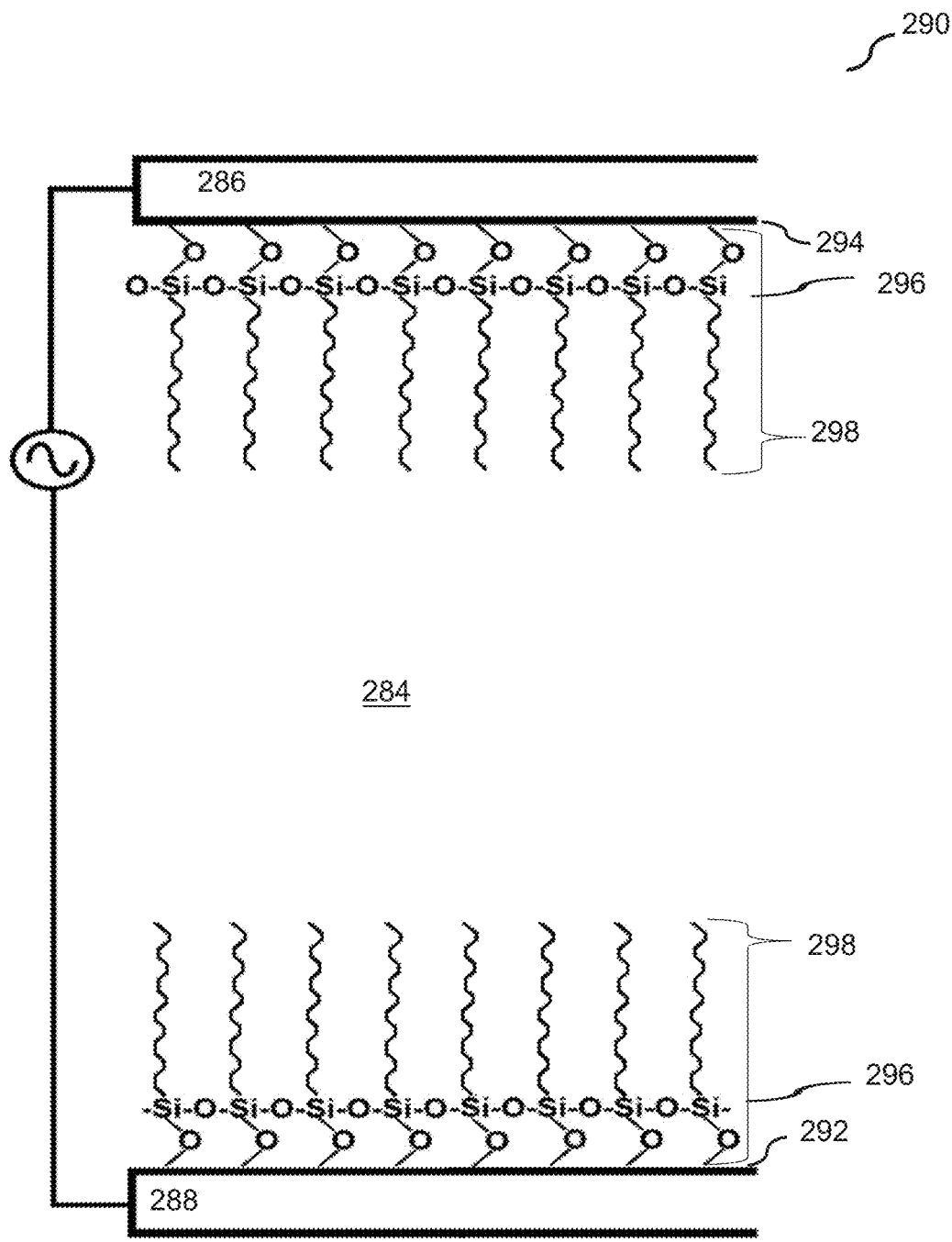
FIG. 2H is a graphical representation of a coated surface of the microfluidic device according to an embodiment of the disclosure.

FIG. 2H depicts a cross-sectional view of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated, a fluoroalkyl terminated moiety, a PEG-terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate). Further details of appropriate coating treatments and modifications may be found at U.S. application Ser. No. 15/135,707, filed on Apr. 22, 2016, and is incorporated by reference in its entirety.

Additional System Components for Maintenance of Viability of Cells within the Sequestration Pens of the Microfluidic Device.

To promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

System Operation and Optical Control.

Figure 3A:
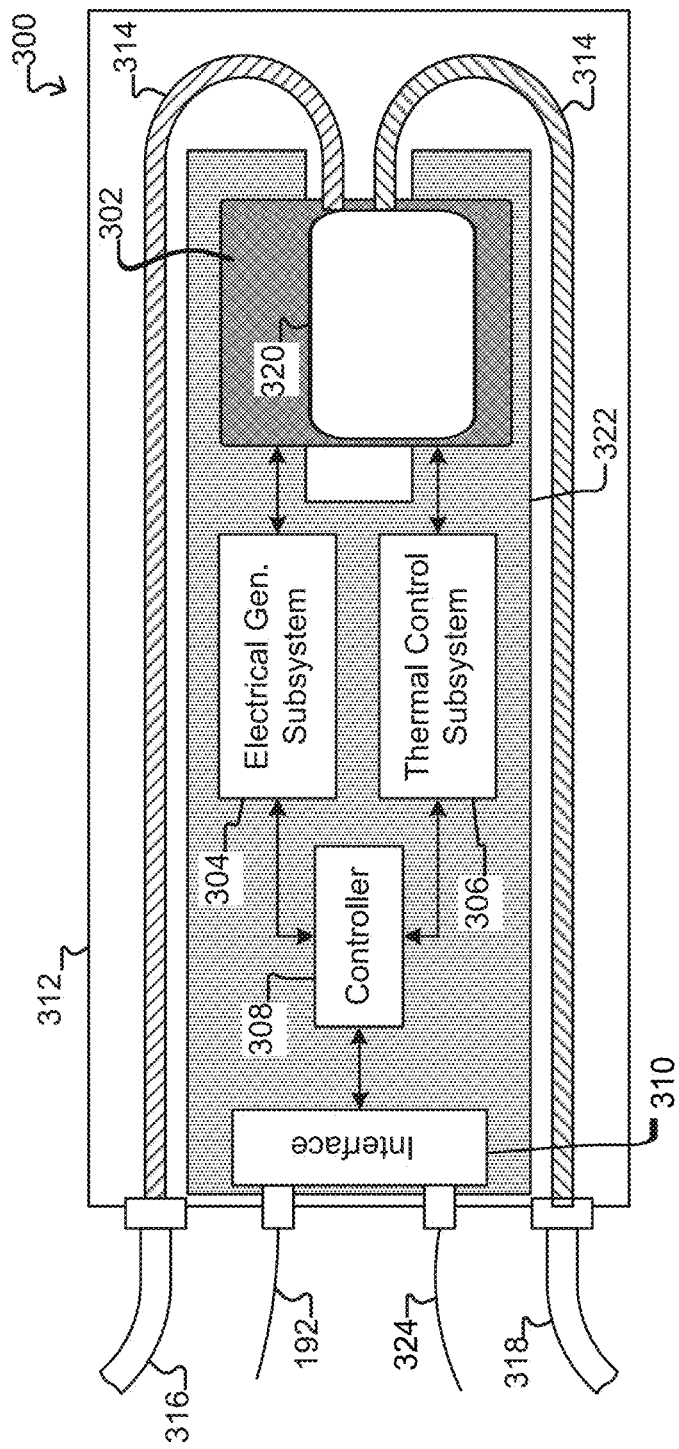
FIG. 3A is a graphical representation of a specific example of a system for use with a microfluidic device and associated control equipment according to some embodiments of the disclosure.
Figure 3B:
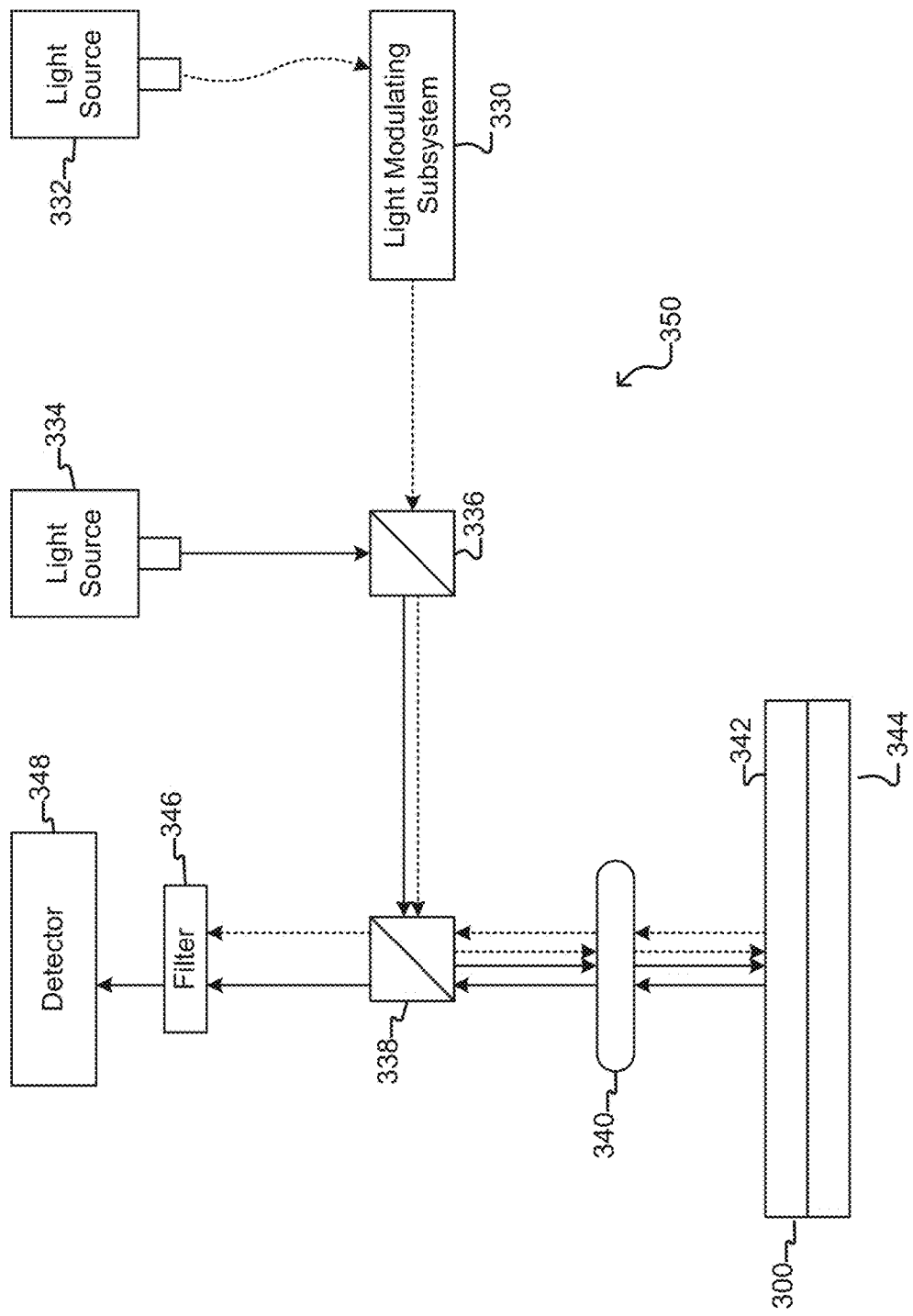
FIG. 3B is a schematic representation an imaging device according to some embodiments of the disclosure.

FIGS. 3A through 3B shows various embodiments of system 150 which can be used to operate and observe microfluidic devices (e.g. 100, 200, 230, 250, 280, 290, 500, 550, 560, 600, 620, 640, 670, 700, 720, 720, 750, 760, 780, 808, 810, 812, 900, 1000, 1100, 1200, 1300, 1400, 1500) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further includes a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can include an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 includes an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 includes a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. One example of a suitable light modulating subsystem 330 is the Mosaic™ system from Andor Technologies™. In certain embodiments, imaging module 164 and/or motive module 162 of system 150 can control the light modulating subsystem 330.

In certain embodiments, the imaging device 194 further includes a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3B, and the laser illumination may be introduced at any suitable physical location within the optical system. The schematic locations of light source 432 and light source 402/light modulating subsystem 404 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Devices and Method for Dislodging One or More Micro-Objects Using Optically Driven Convection and Micro-Object Displacement.

Micro-objects such as biological cells or embryos, may be moved in their local environment, such as within a microfluidic device by a number of forces, including, but not limited to gravity, fluidic flow induced by a mechanical pump, electrowetting and/or dielectrophoresis (DEP). In order to more effectively move micro-objects from one location (e.g. a specific location where the micro-objects may have been cultured within a microfluidic device) to another location (e.g. another area of the same microfluidic device or a separate device such as a multiwell plate), varying force vectors may be applied to achieve cell translocation. While dielectrophoresis (DEP), fluid displacement, and the like may be sufficient to move cells in the desired manner, forces applied at different scale (e.g., a more powerful force or a more localized force), in different ways (convective forces, shear flow forces, impacting forces such as cavitation or contact with a meniscus of a bubble, or any combination thereof) and/or on different timescales (e.g., from milliseconds to minutes in duration) may also be employed to assist in moving cells from a present location and/or to a selected location. In one non-limiting example, application of forces other than DEP may be useful to move biological cells have been cultured within a microfluidic device for a period of time. The cells may have attached to a surface of the microfluidic device such that DEP forces or gravity may not be sufficient to move the cells from an attached position. Therefore, forces having other characteristics may be useful in dislodging one or more biological cell for which DEP forces are not sufficient or where gravity or mechanically pumped fluidic flow cannot selectively and/or sufficiently dislodge a selected cell.

It has been surprisingly found that optical illumination of discrete selected regions on or within a microfluidic device can heat a portion of a fluidic medium within the microfluidic circuit of the microfluidic device to provide a variety of displacement forces differing in scale, physical type and/or timescale which are capable of displacing micro-objects (including but not limited to biological cells) and/or mixing fluidic media (which may contain micro-objects including biological cells) within the microfluidic device, while still providing at least a portion of the micro-objects so displaced are still viable. The generation of such displacing forces may be applied more than once at the same discrete selected region or adjacent thereto, such that repeated force can be applied to dislodge cells and/or mix media (which may include micro-objects), while being sufficiently non-destructive towards micro-objects. Translocating cells from one area, which in some embodiments may be a chamber, sequestration pen, or other microfluidic circuit element of a microfluidic device, to another area and/or location within the microfluidic device, or alternatively, to another device outside of the microfluidic device (e.g. a multi-well plate) may be accomplished by applying a pulse of optical illumination to selected discrete regions within the microfluidic device. The pulse of optical illumination may be applied on, or within proximity to, the cells of interest. The force vector applied is a function of the energy, duration, and location of the pulse of optical illumination. In some embodiments, the pulse of optical illumination can be used to locally heat the surrounding cell media (i.e. fluidic medium), thereby increasing the local vapor pressure to create a vapor-fluid interface that produces a bubble. The effect upon the surrounding fluidic media and/or cell(s) of the heat-induced bubble generation may vary, depending on the duration and configuration of the microfluidic device and/or the thermal target. Some variety of effects may include:

Cavitation.

A short pulse of light may be used to heat the thermal target to generate a short-lived bubble. The bubble, upon collapse, creates a cavitating force that may dislodge cells that may be disposed nearby. In some embodiments, the short pulse of light is directed at one or more cells, which may be dislodged by a cavitating force so formed.

Shear Flow.

In other embodiments, the bubble may be grown by continued illumination to create a shear flow of fluid directed towards nearby cell(s) and thereby dislodge the cell(s).

Meniscus Contact.

Alternatively, the bubble(s) created by heating the fluidic medium at the site of the thermal target may be directed towards the cell(s). As the bubble moves, the meniscus of the bubble may contact the cell(s) and dislodge them from the surface.

In other embodiments, the bubble can be grown until it is thermodynamically favorable to stabilize and persist in the fluidic medium. The bubble may then displace the surrounding liquid phase and thereby dislodge the cells.

Convective Flow.

Without intending to be limited by theory, illumination of a thermal target which generates heating in the fluidic medium surrounding the thermal target may nucleate and propagate bubbles. The presence of a persistent bubble having a thermal gradient may produce a thermal capillary convection flow (Gibbs-Marangoni effect). The Gibbs-Marangoni effect refers to the flow of liquid along a surface tension gradient. A liquid may flow from an area of low surface tension to an area of high surface tension. Because surface tension is decreased at higher temperature, a temperature gradient on the surface of a bubble can cause liquid surrounding the bubble to flow in the direction of the gradient (i.e. from the area of high temperature to the area of low temperature), and may form a convective flow. For simplicity of explanation, the flow created by the temperature gradient on the surface of the bubble is herein referred to as a "Marangoni-effect flow." The greater the temperature difference between the hot and cold areas of the surface, the greater the velocity of the Marangoni-effect flow. By changing the optical power, the flow may be modulated. Such a convective flow may be used to move cells or mix fluidic media. In some embodiments, a cyclized flow created by heating induced by optical illumination may be used to dislodge cells within an isolation region of a sequestration pen. In other embodiments, cyclized flow may be induced in a localized region of microfluidic devices otherwise devoid of fluidic flow, which may be used to mix media in the localized regions.

After dislodging the cell(s), further translocation of the cell(s) may be accomplished by using any other suitable method of moving cells, including but not limited to fluidic displacement, DEP, gravity, and the like.

Optical Illumination.

The optical illumination can be a coherent light source (e.g., a laser) or a non-coherent light source. The coherent light source may be a laser characterized by a wavelength in the visible light spectrum (e.g., a red wavelength, such as 662 nm), or may be a laser characterized by a wavelength in the infrared part of the spectrum (e.g., a near infra-red wavelength, such as 785 nm), or may be a laser having any other suitable wavelength. The non-coherent light source may contain light having wavelengths in the visible range, and/or may include light having wavelengths in the ultraviolet (uv) or infrared range. The light source may provide structured or unstructured light. Temperature gradients introduced by illumination with a light source, may be modulated by increasing or decreasing the intensity of the light source. A structured light source may be modulated in a number of ways to control the properties of the structured light source (e.g. using a DMD to spatially modulate the light source, or using an aperture and objective to modulate the lights source as described above with respect to FIG. 3B.

Without being bound by theory, the incident optical illumination may be transmitted through a transparent, substantially transparent, and/or translucent cover or base of the enclosure microfluidic device. After being transmitted through the cover or base of the enclosure, the incident illumination can be transmitted to a thermal target, as described below, which is configured to convert the optical illumination to thermal energy.

Power.

Non-coherent light may be projected in a range from about 1 milliwatts (mW) to about 1000 milliwatts (mW), but is not limited to this range. In some embodiments, the power of the non-coherent light, structured or non-structured may be in a range of about 1 milliwatt to about 500 milliwatts; about 1 milliwatt to about 100 milliwatts; about 1 milliwatt to about 50 milliwatts; about 1 milliwatt to about 20 milliwatts; about 10 milliwatts to about 500 milliwatts; about 10 milliwatts to about 200 milliwatts, about 10 milliwatts to about 100 milliwatts; about 50 milliwatts to about 800 milliwatts; about 50 milliwatts to about 500 milliwatts; about 50 milliwatts to about 200 milliwatts; about 75 milliwatts to about 700 milliwatts; about 75 milliwatts to about 400 milliwatts; about 75 milliwatts to about 175 milliwatts, or any value therebetween. Depending on the area to which the light is focused, and on the duration of illumination, the power of the non-coherent light may be less or more than any of the power levels described above. Coherent light may be projected in a range from about 1 milliwatts to about 1000 milliwatts, but is not limited to this range. Depending on the area to which the light is focused, and on the duration of illumination, the power of the coherent light may be less or more than any of the power levels described above. In some embodiments, the power of the coherent light may be in a range of 1 milliwatt to about 500 milliwatts; about 1 milliwatt to about 100 milliwatts; about 1 milliwatt to about 50 milliwatts; about 1 milliwatt to about 20 milliwatts; about 10 milliwatts to about 500 milliwatts; about 10 milliwatts to about 200 milliwatts, about 10 milliwatts to about 100 milliwatts; about 50 milliwatts to about 800 milliwatts; about 50 milliwatts to about 500 milliwatts; about 50 milliwatts to about 200 milliwatts; about 75 milliwatts to about 700 milliwatts; about 75 milliwatts to about 400 milliwatts; about 75 milliwatts to about 175 milliwatts, or any value therebetween.

The power of the incident light may be chosen to be different based on the type of dislodging force desired. For example, if a cyclized flow which may incorporate a Marangoni-effect flow is desired, the power of the incident light may be selected to be as low as 1 milliwatt and modulated variously as the cyclized flow is established and/or maintained. When dislodging micro-objects by use of a cavitating force, shear flow force, or bubble contact force the power may be selected to be in a higher range, for example from about 10 milliwatts to about 100 milliwatts. The power may also be adjusted based on the duration of the illumination desired as well.

Site of Illumination.

The site of illumination may be selected to be any discrete selected region of the microfluidic device, as may be useful. In some embodiments, the discrete selected region of illumination may be a location within a sequestration pen of a microfluidic device. In various embodiments, the discrete selected region of illumination is located within an isolation region of a sequestration pen, which may be configured like any sequestration pen described herein, including but not limited to 124, 126, 128, 130, 224, 226, 228, 266, 502, 504, 506, 604, 606, 608, 704, 732, 734, 736, 738, 802, 804, 806, 902, 1002, 1102, 1202, 1402, 1502. In various embodiments, the discrete selected region of illumination may be within a displacement force generation region of the sequestration pen, as described more fully below. In other embodiments, the discrete region of illumination may be within a cyclic culturing pen. When illumination is performed within a cyclic culturing pen, it may be directed at a discrete selected region in a displacement force generation region, connection region, cell culturing region or at an opening of the cyclic culturing pen to a microfluidic channel. In yet other embodiments, the discrete selected region of illumination may be located within a microfluidic channel, as described more fully below.

Microfluidic Devices

The disclosure provides for microfluidic devices configured to be capable of optically driven convection flow generation and/or displacement of micro-objects therein. In one aspect of the disclosure, a microfluidic device is provided having an enclosure, where the enclosure includes a flow region and a sequestration pen, where the sequestration pen may include a connection region and an isolation region, where the connection region includes a proximal opening to the flow region and a distal opening to the isolation region. The sequestration pen may include a thermal target in the isolation region. In various embodiments, the sequestration pen further includes a displacement force generation region, where the isolation region includes at least one fluidic connection to the displacement force generation region; and the displacement force generation region further includes a thermal target. In various embodiments, the microfluidic device may have at least one sequestration pen which may be configured as any of sequestration pens 124, 126, 128, 130, 224, 226, 228, 266, 502, 504, 506, 604, 606, 608, 704, 732, 734, 736, 738, 802, 804, 806, 902, 1002, 1102, 1202, 1402, 1502. In various embodiments, the thermal target or the displacement force generation region may be configured to constrain expansion of a gaseous bubble formed thereupon in one predominate direction.

In various embodiments, the enclosure of the microfluidic device may further include a cover that defines, in part, the sequestration pen, where the thermal target may be disposed on the cover. In some embodiments, the thermal target may be disposed on an inner surface of the cover facing the enclosure. In other embodiments, the enclosure of the microfluidic device may further include a microfluidic circuit structure that defines, in part, the sequestration pen, and the thermal target may be disposed on the microfluidic circuit structure. In yet other embodiments, the enclosure of the microfluidic device may further include a base that defines, in part, the sequestration pen, and the thermal target may be disposed on an inner surface of the base.

In another aspect of the disclosure, a microfluidic device is provided, having an enclosure where the enclosure includes a microfluidic circuit configured to contain a fluidic medium, where the microfluidic circuit is configured to accommodate at least one cyclic flow of the fluidic medium; and a first thermal target disposed on a surface of the enclosure within the microfluidic circuit, wherein the first thermal target is configured to produce a first cyclic flow of the fluidic medium upon optical illumination.

In various embodiments of the microfluidic device comprising a microfluidic circuit configured to accommodate a cyclized flow, the enclosure of the microfluidic device may further include a microfluidic channel and a sequestration pen, and further where the sequestration pen may be adjacent to and opens off of the microfluidic channel. In various embodiments, the sequestration pen may be configured as any of sequestration pens 124, 126, 128, 130, 224, 226, 228, 266, 502, 504, 506, 604, 606, 608, 704, 732, 734, 736, 738, 802, 804, 806, 902, 1002, 1102, 1202, 1402, 1502. In other embodiments, the microfluidic device comprising a microfluidic circuit configured to accommodate a cyclized flow, the enclosure of the microfluidic device may further include a microfluidic channel and a cyclic culturing pen. The cyclic culturing pen may be configured as any of cyclic culturing pens 602, 802, 1302. The cyclic culturing pen may open off of the microfluidic channel and may further have any other feature or dimension as described herein for a cyclic culturing pen.

In various embodiments of the microfluidic device comprising a microfluidic circuit configured to accommodate a cyclized flow, the cyclic flow path may include a portion of the channel and at least a portion of the sequestration pen. In other embodiments, the cyclic flow path may be disposed within the sequestration pen. In some embodiments, the cyclic flow path may include a constricted portion.

In various embodiments of the microfluidic device comprising a microfluidic circuit configured to accommodate a cyclized flow, the microfluidic device may include a second thermal target configured to produce a second cyclic flow of the fluidic medium upon optical illumination. The second thermal target may be disposed adjacent to the first thermal target on the surface of the enclosure. The second thermal target may be disposed within the same microfluidic circuit as the first thermal target. In various embodiments, the first thermal target and the second thermal target may be oriented to provide the first cyclic flow and the second cyclic flow of the fluidic medium in opposite directions.

In various embodiments of the microfluidic device comprising a microfluidic circuit configured to accommodate a cyclized flow, the thermal target is disposed on a surface within the microfluidic channel. In some embodiments, the enclosure of the microfluidic device may further include more than one microfluidic channel, where a first microfluidic channel may be configured to open from a second microfluidic channel at a first location along the second microfluidic channel and may further be configured to reconnect to the second microfluidic channel at a second location thereby forming the microfluidic circuit; and the thermal target may be disposed on a surface within the first microfluidic channel. In various embodiments, the at least one sequestration pen may open off of the first microfluidic channel. In various embodiments, the at least one sequestration pen may be configured as any of sequestration pens 124, 126, 128, 130, 224, 226, 228, 266, 502, 504, 506, 604, 606, 608, 704, 732, 734, 736, 738, 802, 804, 806, 902, 1002, 1102, 1202, 1402, 1502. In some embodiments, a fluidic resistance of the first channel may be approximately 10 to 100 times higher than a fluidic resistance of the second channel. The second microfluidic channel may have a width that is approximately 1.5 to 3 times larger than a width of the first microfluidic channel. In some embodiments, the width of the second microfluidic channel is about 100 to 1000 microns. In various embodiments, the width of the first microfluidic channel may be about 20 to 300 microns.

In yet another aspect, a microfluidic device is provided, having an enclosure, where the enclosure includes a microfluidic channel and a sequestration pen, and further where the sequestration pen is adjacent to and opens off of the microfluidic channel and a thermal target is disposed in the channel adjacent to an opening to a sequestration pen, and wherein the thermal target is further configured to direct a flow of the fluidic medium into the sequestration pen upon optical illumination. In various embodiments, the at least one sequestration pen may be configured as any of sequestration pens 124, 126, 128, 130, 224, 226, 228, 266, 502, 504, 506, 604, 606, 608, 704, 732, 734, 736, 738, 802, 804, 806, 902, 1002, 1102, 1202, 1402, 1502. In some embodiments, when the microfluidic device having a sequestration pen and a thermal target in the channel has sequestration pens configured as sequestration pens 502, 504, 506, 602, 604, 606, 608, 704, 732, 734, 736, 738, 902, the sequestration pens may not have a thermal target within the sequestration pen itself. In some embodiments, the thermal target may be disposed on a surface within the microfluidic channel.

For any of the microfluidic devices, the enclosure may further include a dielectrophoresis configuration. In some embodiments, the dielectrophoresis configuration may be optically actuated.

For any of the microfluidic devices, at least one surface of the enclosure may include a coated surface. In some embodiments, a sequestration pen of the microfluidic device may include at least one surface that is a coated surface. In some embodiments, the coated surface may be a covalently modified surface.

Thermal Targets.

A thermal target is a microfluidic feature of the microfluidic device which may be a separate feature designed for this purpose. Alternatively, a thermal target may be a location within the microfluidic circuit to which optical illumination is applied. The thermal target is a passive microfluidic feature and does not include any self-activating resistors or electrical heaters. The passive nature of the thermal targets simplifies fabrication of the microfluidic device. For thermal targets including metal or microstructures, fabrication is much less complex than an active thermal target such as a resistor, as is described below. Active thermal targets such as resistors and the like must have fixed electrical connections and are fabricated in fixed positions, unlike the passive thermal targets of the present disclosure. when the thermal target is a selected location of the microfluidic circuit material or base, with no additional structural feature, the flexibility to create forces specifically and selectively where needed is particularly advantageous compared to fixed active thermal targets.

FIGS. 4A-4E illustrate geometries of various thermal targets according to some embodiments of the present disclosure. As can be appreciated by those skilled in the art, any of the characteristics of the thermal targets depicted in FIGS. 4A-E can be combined to produce thermal targets with a range of desired functionalities.

FIG. 4A illustrates a thermal target 430 that is square shaped. The blunt corners and uniform sides of the thermal target 430 of FIG. 4A may be beneficial in nucleating a substantially uniform bubble. Similarly, the circular thermal target 432 illustrated in FIG. 4B provides a shape configured to generate a uniform localized heat source to nucleate a substantially uniform bubble.

Conversely, the thermal targets illustrated in FIGS. 4C, 4D, 4E, and 4G have asymmetric shapes which may be beneficial in creating bubbles with temperature gradients. Without intending to be limited by theory, bubbles with temperature gradients may produce a Gibbs-Marangoni effect (also known as thermo-capillary convection), as described above. The asymmetrical thermal target 434 illustrated in FIG. 4C is characterized by a teardrop-like shape used to create a bubble with a temperature gradient that can be used to generate a Marangoni-effect flow. Because the wider portion 434a of the teardrop-like shape has a larger surface area than the tapered portion 434b of the teardrop-like shape, the larger surface area will generate a higher temperature upon heating by optical illumination. Consequently, a bubble that is generated using the asymmetrical thermal target 434 in FIG. 4C can have a temperature gradient in which an area of the bubble that is positioned over the wider portion 434a of the thermal target will have a higher temperature than an area of the bubble that is positioned over the tapered portion 434b of the thermal target.

The temperature gradient may also be modulated by physically separating differently-sized portions of a thermal target. FIG. 4D illustrates a thermal target 436 which is comprised of two portions 438, 440 of differing sizes that are physically separated but situated in close proximity such that they can be heated using the same structured light source. The physical separation of the two portions 438, 440 of the thermal target 436 creates a greater temperature differential which can be used to create a Marangoni-effect flow having greater velocity, and hence, increased force. FIG. 4E illustrates a thermal target 442 that has been further segregated into three portions 444, 446, 448.

The thermal target 430, 432, 434, 436, 442, 450, 452 illustrated in FIGS. 4A-4G can be created by depositing a contiguous metal shape or a non-contiguous metal shape onto one surface of the microfluidic circuit structure 108 or cover 110. In some embodiments, the thermal target may be disposed on an inner surface of the cover 110. The thermal target faces towards the interior (chamber/region 202) of the enclosure 102 where it may be in contact with fluidic medium. The thermal targets 430, 432, 434, 436, 442, 450, 452 can include any type of metal that can be excited by a light source to produce heat. Suitable metals include chromium, gold, silver, aluminum, indium tin oxide, or any combination thereof. Other metals (and alloys) are known in the art. The thermal target 440 can have a continuous metal surface or can be composed of a non-contiguous shape of metal (e.g. metal shapes such as dots). Various patterns can be used to optimize heating and the generation of uniform bubbles.

FIG. 4F illustrates a thermal target 450 comprising a non-contiguous metal shape. In the embodiment illustrated in FIG. 4F, the shapes are dots. However, any type of metal shape can be used (e.g. squares, lines, cones, squiggles). In addition, a variety of different metal shapes may be used in the same thermal target.

In some embodiments, non-contiguous metal shapes may be distributed in an increasing concentration in order to enhance the temperature gradient of the thermal target 450. FIG. 4G illustrates a thermal target 452 that has been patterned with a gradient of metal shapes. By increasing the density of distribution of the metal dots in the wider portion 452a of the thermal target 452 and decreasing the density of distribution of the metal dots in the narrower portion 452b of the thermal target 452, the temperature gradient of the thermal target 452 may be enhanced.

In some embodiments, the thickness of the metal deposited as a contiguous metal shape or a noncontiguous metal shape(s) in a thermal target may be varied in order to enhance the temperature gradient of the thermal target. For example, a thicker deposit of metal may be used to generate more heat in a larger (or wider) portion of the thermal target, thereby enhancing the temperature gradient. In some embodiments, the thickness of the deposited metal in a thermal target may be in the range of about 3 nm to about 50 nm, about 3 nm to about 30 nm, about 5 nm to about 50 nm, about 5 nm to about 30 nm, about 5 nm to about 25 nm, or any value therebetween.

Microstructures.

As described above, in some embodiments, the microfluidic circuit structure 108 or cover 110 of the enclosure 102 may have one or more microstructures introduced thereupon to create a surface topography that may promote bubble nucleation and/or formation from heat generated upon optical illumination, and function as a thermal target. The microstructure(s) may be a non-contiguous formation The microstructure(s) may be a negative feature (e.g., depressions or divots created upon the surface of the base or on the surface of a wall. As is known the art, microstructure(s) such as pillars, dots, cavities or divots may be patterned into the microfluidic circuit structure 108 or cover 110 in order to create suitable sites for bubble nucleation. FIG. 4H is a stylized illustration of a thermal target 454 comprising divots that may be used for bubble nucleation. In some embodiments, surface topographies may be combined in various ways with metal patterns to create an ideal surface for thermal absorption generating subsequent displacement forces. The microstructure(s) may have an area in the x-axial and y-axial direction as viewed from above in the range of about 50 square microns, 100 square microns; about 200 square microns, about 300 square microns, about 500 square microns, or any value therebetween. A microstructure may include only one unit or may be a plurality of microstructures which together have a total area as described. Negative microstructure(s) may be formed by focusing a light source (e.g., a laser or a non-coherent light) on patternable microfluidic circuit material that may be disposed on the base or may be part of the walls, where the focused light may pattern the patternable microfluidic circuit material and form the divots or depressions.

Alternatively, the microstructure(s) may be a positive feature, e.g., rising above the surface of the base or extending from a wall of the enclosure, flow region or sequestration pen (non-limiting examples including pillars or dots (not shown)). The microstructure(s) may have any conveniently fabricated height within the enclosure. It may have a height that still permits passage of a micro-object such as a biological cell over the microstructure. The height of the microstructure(s) may be about 5 microns, about 10 microns, about 15 microns, about 20 microns, about 25 microns, about 30 microns, about 35 microns, about 40 microns, or any value therebetween. Each of the plurality of microstructures does not have to have the same height but may have a different height from each other. The positive microstructure(s) may be formed from the same material used to form the microfluidic circuit structure, e.g., PDMS, or any photopatternable silicone, and may be formed during the same process used to fabricate the other elements of the microfluidic circuit, such as walls, sequestration pens or channels.

In some other embodiments, the positive microstructures may be formed from a hydrogel, such as a photo-initiated polymer. The photo-initiated polymer may be a synthetic polymer, a modified synthetic polymer, or a light activatable biological polymer. In some embodiments, the biological polymer may be modified to incorporate moieties providing the ability to be light activatable.

In some embodiments, the photo-initiated polymer may include at least one of a polyethylene glycol, modified polyethylene glycol, polylactic acid (PLA), modified polylactic acid, polyglycolic acid (PGA), modified polyglycolic acid, polyacrylamide (PAM), modified polyacrylamide, poly-N-isopropylacrylamide (PNIPAm), modified poly-N-isopropylacrylamide, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, laminin, modified laminin, polysaccharide, modified polysaccharide, or a co-polymer in any combination. In other embodiments, the polymer may include at least one of a polyethylene glycol, modified polyethylene glycol, polylactic acid (PLA), modified polylactic acid, polyglycolic acid (PGA), modified polyglycolic acid, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, laminin, modified laminin, polysaccharide, modified polysaccharide, or a co-polymer in any combination. In yet other embodiments, the polymer may include at least one of a polyethylene glycol, modified polyethylene glycol, polylactic acid (PLA), modified polylactic acid, polyglycolic acid (PGA), modified polyglycolic acid, polyvinyl alcohol (PVA), modified polyvinyl alcohol, polyacrylic acid (PAA), modified polyacrylic acid, fibronectin, modified fibronectin, collagen, modified collagen, laminin, modified laminin, or a co-polymer in any combination. In some embodiments, the photo-initiated polymer does not include a silicone polymer. In some embodiments, the photo-initiated polymer may not include a polylactic acid (PLA) or a modified polylactic acid polymer. In other embodiments, the photo-initiated polymer may not include a polyglycolic acid (PGA) or a modified polyglycolic polymer. In some embodiments, the photo-initiated polymer may not include a polyacrylamide or a modified polyacrylamide polymer. In yet other embodiments, the photo-initiated polymer may not include a polyvinyl alcohol (PVA) or a modified polyvinyl alcohol polymer. In some embodiments, the photo-initiated polymer may not include a polyacrylic (PAA) or modified PAA polymer. In some other embodiments, the photo-initiated polymer may not include a polycaprolactone (PCL) or a modified polycaprolactone polymer. In other embodiments, the photo-initiated polymer may not be formed from a fibronectin or a modified fibronectin polymer. In some other embodiments, the photo-initiated polymer may not be formed from a collagen or a modified collagen polymer. In some other embodiments, the photo-initiated polymer may not be formed from a laminin or a modified laminin polymer.

Physical and chemical characteristics determining suitability of a polymer for use in the solidified polymer network may include molecular weight, hydrophobicity, solubility, rate of diffusion, viscosity (e.g., of the medium), excitation and/or emission range (e.g., of fluorescent reagents immobilized therein), known background fluorescence, characteristics influencing polymerization, and pore size of a solidified polymer network. The photo-initiated polymer may be formed upon polymerization of a flowable polymer (e.g., a pre-polymer solution). Briefly, a flowable polymer solution may be flowed into the microfluidic device and solidified in-situ, prior to use in the methods described herein. Methods of installing microstructures derived from a photo-initiated polymer are more fully described in U.S. application Ser. No. 15/372,094 filed on Dec. 7, 2016.

One type of polymer, amongst the many polymers that may be used, is polyethylene glycol diacrylate (PEGDA). Light initiated polymerization may be initiated in the presence of a free radical initiator, such as Igracure® 2959 (BASF), a highly efficient, non-yellowing radical, alpha hydroxy ketone photoinitiator, is typically used for initiation at wavelengths in the UV region (e.g., 365 nm), but other initiators may be used. An example of another useful photoinitiator class for polymerization reactions is the group of lithium acyl phosphinate salts, of which lithium phenyl 2, 4, 6,-trimethylbenzolylphosphinate has particular utility due to its more efficient absorption at longer wavelengths (e.g., 405 nm) than that of the alpha hydroxy ketone class.

Other types of PEG that may be photopolymerized include PEG dimethylacrylate, and/or multiarm PEG (n-PEG) acrylate (n-PEG-Acr). Other polymer classes that may be used include poly vinyl alcohol (PVA), polylactic acid (PLA) polyacrylic acid (PAA), polyacrylamide (PAM), polyglycolic acid (PGA) or polycaprolactone (PCL).

The molecular weight range of the polymer may be varied as required for the performance of the microstructure(s). A wide range of molecular weights of the flowable polymer may be suitable, depending upon the structure of the polymer. A useful star type polymer may have Mw (weight average molecular weight) in a range from about 500 Da to about 20 kDa (e.g., four arm polymer), or up to about 5 kDa for each arm or for a linear polymer, or any value therebetween. In some embodiments, a polymer having a higher molecular weight range, may be used at lower concentrations in the flowable polymer, and still provide microstructure(s) that may be used in the methods described herein.

Various co-polymer classes may be used, including but not limited to: any of the above listed polymer, or biological polymers such as fibronectin, collagen or laminin. Polysaccharides such as dextran or modified collagens may be used.

In some embodiments, the microstructure(s) may be or form part of a sacrificial feature as used in the methods described herein, and may be deformed or deteriorated as a result of absorbing optical illumination and generating thermal effects, which can be used to move micro-objects.

Alternatively, a thermal target may be created in situ by projecting structured light on the microfluidic circuit structure 108 or cover 110 to create patterns of light that have the same geometries as the thermal target 450. This approach does not require any special metal deposition or microfluidic circuit material patterning. FIG. 4I provides a stylized illustration of a thermal target 456 created by projecting a circular pattern of light on the microfluidic circuit structure 108 or cover 110. Projecting patterns of light having particular geometries may also be used in conjunction with thermal targets comprising various geometries, surface topographies, metal patterns and combinations thereof.

In yet other embodiments, optical illumination is focused on portions of microfluidic circuit material of sequestration pen walls, inner surface of the base which faces the enclosure of the microfluidic device, or selected point on a microfluidic channel wall, and do not contain any of the above described special features of a thermal target. However, these discrete selected regions of the microfluidic circuit material of sequestration pens or walls, or the inner surface of the base may also be utilized as thermal targets and may function as a sacrificial feature.

Size.

A thermal target may have a first dimension (e.g., width or x-axial dimension of the microfluidic enclosure) of about 1 mm, 0.9 mm, 0.7 mm, 0.5 mm, 0.3 mm, 100 microns, 80 microns, 60 microns, 40 microns, 20 microns, about 10 microns, about 5 microns or any value therebetween. The step of illuminating a selected discrete region may further include illuminating a region having a second dimension (e.g., a y-axial dimension within the microfluidic enclosure) of about 1 mm, 0.9 mm, 0.7 mm, 0.5 mm, 0.3 mm, 100 microns, 80 microns, 60 microns, 40 microns, 20 microns, about 10 microns, about 5 microns or any value therebetween. The x-axial and y-axial dimensions may be any combination of the dimensions as above. In some embodiments, a thermal target may have an x-axial dimension of about 100 microns and a y-axial dimension of about 100 microns. In other non-limiting embodiments, the thermal target may have an x-axial dimension of about 5 microns and a y-axial dimension of about 5 microns.

Some embodiments of sequestration pens and cyclic culturing pens for optically driven convection and displacement. As described above, a sequestration pen useful for optically driven convection and/or displacement of micro-objects may have a displacement force generation region, which is fluidically connected to the isolation region of the sequestration pen, where micro-objects may be disposed and, optionally, maintained. The displacement force generation region may be connected to a distal portion of the isolation region, opposite to the opening of the isolation region to the connection region. Alternatively, the displacement force generation region may be connected to the isolation region at or adjacent to the opening of the isolation region to the connection region. In some embodiments, the displacement force generation region may have more than one fluidic connection to the isolation region. (See FIGS. 7A-7F). In some embodiments, the sequestration pen may include a cyclic flow path. The cyclic flow path may include the isolation region and the displacement force generation region. (See FIGS. 6A-6C). In some embodiments, the cyclic flow path may include a constricted portion. (See FIG. 6A).

In some other embodiments, the displacement force generation region may include one or more fluidic connections to the isolation region which interrupt the opening of the isolation region to the connection region. In some embodiments, at least one fluidic connection between the isolation region and the displacement force generation region may include a cross sectional dimension configured to prevent passage of a micro-object from the isolation region to the displacement force generation region. Preventing micro-objects from possible entry into the displacement force generation region may decrease damage from heat or impact and may further assist in maintaining the micro-objects within the isolation region of the sequestration pen. In some embodiments, the at least one fluidic connection between the isolation region and the displacement force generation region includes one or more barrier modules (see FIGS. 7A-7F, 726, 726a, 726b, 726c, 726d, or 726e), wherein the one or more barrier modules are configured to prevent passage of a micro-object from the isolation region to the displacement force generation region. The barrier module(s) may be of any size or shape, and the gap (See FIG. 7A-7F, 728, 728a, 728b, 728c, 728d, 728e) between a barrier module and its neighbor, or the gap between a barrier module and a wall of the sequestration pen may have a dimension such that a micro-object such as a biological cell may not pass from the isolation region to the displacement force generation region. In some embodiments, a micro-object such as a micro-bead may pass from the isolation region into the displacement force generation region but a micro-object such as a biological cell or an embryo may not pass by the barrier module(s) into the displacement force generation region. A barrier module may have a dimension across a sequestration pen that is about 10%, 20%, 30%, 40%, 50% 60% 70%, about 80%, or any value therebetween, of the width of the sequestration pen. The gap between the barrier module and its neighbor or the gap between a barrier module and a wall may be about 5 microns, 7 microns, 9 microns, 11 microns, 13 microns, 15 microns, 17 microns, 20 microns, 25 microns, or about 40 microns, depending on the size of the micro-object disposed within the isolation region.

In various embodiments, the at least one fluidic connection between the isolation region and the displacement force generation region may have a cross sectional dimension configured to prevent fluidic flow from the displacement force generation region in the absence of a force generated therein, except by diffusion. (See FIGS. 9A-9C.) The dimensions of the displacement force generation region may match that of the isolation region. The displacement force generation region may be a separate compartment of a sequestration pen. In various embodiments, the displacement force generation region may be configured to minimize secondary flows.

In some embodiments, the sequestration pen may include a second thermal target configured to produce a second cyclic flow of the fluidic medium upon optical illumination. The second thermal target may be disposed within the displacement force generation region. The first thermal target and the second thermal target may be oriented to provide a first cyclic flow and a second cyclic flow of the fluidic medium in opposite directions.

In various embodiments, the displacement force generation region may include a single opening, where the single opening may be the fluidic connection of the displacement force generation region to the isolation region. In some embodiments, the fluidic connection of the displacement force generation region may include a fluidic connector. (See FIG. 5A, fluidic connector 514.) In some embodiments the fluidic connector of the displacement force generation region may include at least one curved portion. (See FIG. 5A, fluidic connector 514.) In some embodiments, the at least one curved portion of the fluidic connector may include a turn of about 60 degrees to about 180 degrees; about 60 degrees to about 120 degrees, about 60 degrees to about 90 degrees; about 40 degrees to about 180 degrees, about 40 degrees to about 120 degrees, about 40 degrees to about 90 degrees, or any value therebetween. In other embodiments, the fluidic connector of the displacement force generation region may include at least two curved portions. In some embodiments, each of the at least two curved portions of the fluidic connector may include a turn of about 60 degrees to about 180 degrees; about 60 degrees to about 120 degrees, about 60 degrees to about 90 degrees; about 40 degrees to about 180 degrees, about 40 degrees to about 120 degrees, about 40 degrees to about 90 degrees, or any value therebetween. When turns are included in the fluidic connecter between the displacement force generation region and the isolation region, the sequestration pen as a whole may have a shape resembling a "U"-like shape, an "N"-like or reverse "N"-like shape.

In various embodiments, a width of the fluidic connector may be the same as a width of the isolation region and/or the displacement force generating region. In some embodiments, the fluidic connector may include a cross sectional dimension, in the x-axial and y-axial dimension, configured to prevent passage of a micro-object from the isolation region to the displacement force generation region. In various embodiments, the height of the fluidic connector, in the z-axial direction, may also vary, such that a micro-object cannot pass. From the isolation region to the displacement force generation region.

In various embodiments, the thermal target or the displacement force generation region within a sequestration pen may be configured to constrain expansion of a gaseous bubble formed thereupon in one predominate direction. For example, the displacement force region may be elongate, and may have the thermal target located at the distal portion of the displacement region such that cavitation force/bubble growth/shear flow/convective flow is forced in the direction towards the fluidic connection with the isolation region. This is not a limiting description of the configurations of thermal targets or displacement force generation regions that can constrain expansion of a gaseous bubble, and other configurations are possible.

In various embodiments, the thermal target may be positioned in a portion of the displacement force generation region distal to the least one fluidic connection to the isolation region. In some embodiments, the displacement force generation region may have a width of approximately 20-100 microns in an x-axial or y-axial dimension, depending on the orientation of the displacement force generation region within the microfluidic device. In some embodiments, the displacement force generation region may be configured to minimize secondary flows of fluidic media, which maximizes the force directed at the cell(s) in the isolation region.

A cyclic culturing pen may have a connection region and a displacement force generation region having any combination of features or dimension described above for a sequestration pen. A cyclic culturing pen may include a culturing region which may have any dimensions or features described for an isolation region of a sequestration pen, but differs in the respect that a cyclic culturing pen is configured to cycle flow through the main channel and into the culturing region when actively cycling. In various embodiments, the displacement force generation region of a cyclic culturing pen may further include an opening to the flow region. One embodiment of a cyclic culturing pen is described more fully below for FIG. 6A.

The configurations of the microfluidic devices of the disclosure and their uses may be more fully understood by turning to FIGS. 5A-8D.

Figure 5A:
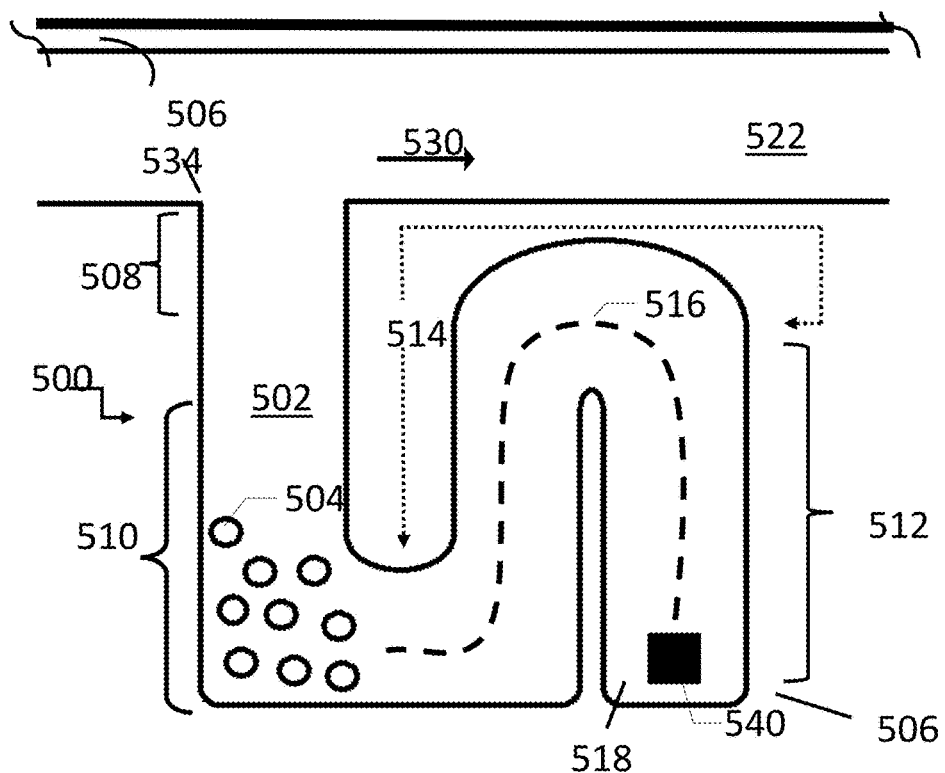
FIGS. 5A-5E are graphical representations of sequestration pens according to some embodiments of the disclosure.

FIG. 5A illustrates an example of a sequestration pen 502 opening off of channel 522, which is configured to contain a fluidic medium flow 530 in microfluidic device 500. Sequestration pen 502 includes a thermal target 540 configured to generate bubbles (not shown) used to export micro-objects 504 from the sequestration pen 502 according to some embodiments of the present disclosure. The sequestration pen 502 includes an isolation region 510 for storing and/or culturing micro-objects 504 such as cells. The isolation region 510 and the thermal target 540 are physically separated by a displacement force generation region 512 which also includes a fluidic connector 514 which permits sufficient space for a bubble to be nucleated and increased in volume (referred to herein as "expanding the bubble") by focusing light (not shown) on the thermal target 540. As the bubble grows by increasing in volume, the expanding bubble generates a force on the fluid in the displacement force generation region (512 plus 514), thus creating a shear flow (not shown) of fluid along a path 516. In many embodiments, the thermal target 540 may be positioned at the distal end of the displacement force generation region 512 (plus 514) to ensure that the bubble exerts force in a predominate direction as it expands. In some embodiments, either the thermal target or the displacement force generation region is configured to constrain expansion of the bubble such that it may expand only in one predominate direction as thermal energy is continued to be supplied by continued illumination. The fluidic connector 514 between the isolation region and the displacement force generation region (512 plus 514) may have a cross sectional dimension configured to prevent fluidic flow from the displacement force generation region (512 plus 514) in the absence of a force generated therein, except by diffusion.

In instances where the micro-objects are biological micro-objects (e.g. biological cells), the displacement force generation region (512 plus 514) also serves to physically separate the biological micro-objects from the heat generated by the thermal target 450 upon optical illumination. In some instances, the expanding bubble also serves to provide a physical barrier between the micro-objects 504 and the thermal target 540. As discussed below, the geometry of the sequestration pen 502 may be optimized to maximize the force (and consequent shear flow) from nucleating and expanding a bubble.

The sequestration pen 502 illustrated in FIG. 5A has a shape which resembles the letter "N" in reverse (i.e., a reverse "N"-like shape), however, other embodiments may use different shapes beneficial in generating a shear flow sufficient to displace micro-objects 504 from the sequestration pen 502.

In addition, for simplicity, the sequestration pen 502 has been illustrated without any other features that may be used in practice to provide other desirable functionalities, such as features used to hold cells in place by force of gravity or traps positioned across from the sequestration pen 502 to collect micro-objects 504 and position micro-objects 504 in sequestration pens 502. However, in practice, these features or any other features described herein for a sequestration pen may be used in conjunction with the sequestration pens 502. Similarly, the sequestration pen 502 illustrated in FIG. 5A is illustrated with a square thermal target 540 used to generate a uniform bubble. In other embodiments, other shapes or materials of symmetrical thermal targets may be used. In yet other embodiments, thermal target 540 is not present and optical illumination is directed at microfluidic circuit material 506 in the vicinity of thermal target 540 to nucleate a bubble which may be unstable or stable, which may result in cavitation force, shear flow fluidic force, or bubble contact force to dislodge micro-objects 504.

Figure 5B:
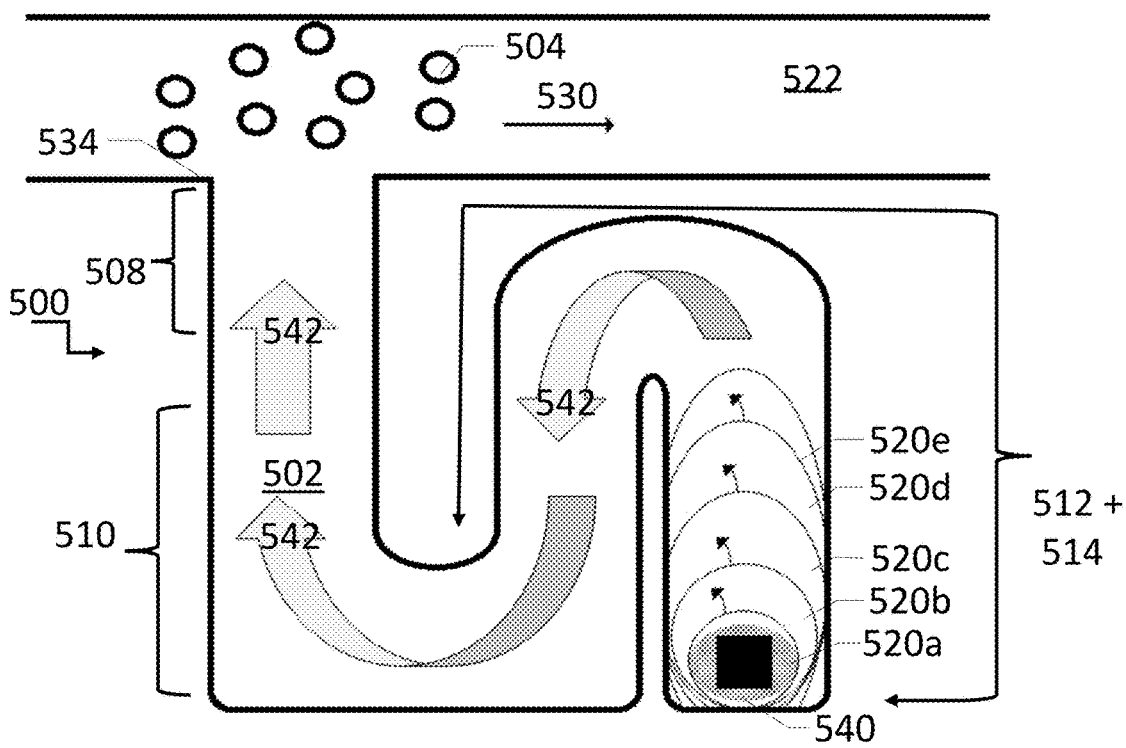

FIG. 5B illustrates the formation of a bubble 520 and use of a shear flow 542 generated by the growing bubble 520 to displace micro-objects 504 from the sequestration pen 502 of FIG. 5A. A light source (not shown) is focused on the thermal target 540 to excite (i.e. heat) the thermal target 540, thereby nucleating a bubble 520a. By continuing to focus the light source on the thermal target 540, the bubble 520a can expand in volume to produce a successively larger bubble 520b, 520c, 520d, 520e. The increasing size of the bubble 520 creates a force on fluidic media (not shown) in the sequestration pen 502, which in turn, creates a shear flow 542 that displaces micro-objects 504 from the isolation region 510 into the channel 522. Once the micro-objects 504 are displaced into the channel 522, they can be manipulated or moved by controlling the flow 530 in the channel 522 or may be moved using DEP.

The displacement force generation region 512, which includes its fluidic connector 514, may be optimized to enhance the shear flow 542 by adjusting the geometry and length of the displacement force generation region. For example, the length and width of the displacement force generation region between the thermal target 540 and the isolation region 510 may be optimized to generate shear flow 542. The thermal target 540 may be positioned at the distal portion of the sequestration pen 502 to ensure that the bubble 520 expands in a single direction. Similarly, the distal portion of the displacement force generation region 512+514 that includes the thermal target 540 may be narrowed in width to ensure that the nucleated bubble 520 expands predominately in one direction. Suitable widths for the distal portion of the displacement force generation region 512+514 can range from approximately 20 to 100 microns. In some embodiments, the fluidic connector region 514 of the displacement force generation region may have the same width as the distal portion of the displacement force generation region 512.

In some embodiments, the displacement force generation region 512+514 may optimized to minimize secondary flows that may interfere with the shear flow 542. As discussed below, the displacement force generation region 512+514 may include a constriction wherein the width of the displacement force generation region 512+514 is significantly reduced. Depending on the embodiment, the width of the constriction may be one-half to one-twentieth the width of the displacement force generation region 512+514. For example, the constriction may have a width ranging from approximately 5-50 microns and the displacement force generation region 512+514 may have a width ranging from approximately 20-100 microns. In some embodiments, the displacement force generation region 512+514 contains one or more (2, 3, 4 or 5) turns in the fluidic connector region 514 of the displacement force generation region.

In the instance illustrated in FIG. 5B, the bubble 520 does not come into contact with the micro-objects 504; the micro objects 650 are only subject to the shear flow 542 generated by growing the bubble. However, in other embodiments of the use of the sequestration pen 502, it may be desirable or even advantageous to bring the meniscus of the bubble 520 into contact with the micro-objects 504 providing a contacting force to displace the micro-objects 504 from the isolation region 510 and, optionally, export the micro-objects 504 from the sequestration pen 502. The export may be an active export driven by the flow of bubbles or may simply dislodge the cells such that another force such as DEP may then export the cells 504 from the sequestration pen 502. In some embodiments, a length of the displacement force generation region 512+514 may be shortened in order to bring the meniscus of the bubble 520 into contact with micro-objects 504 within the isolation region 510. Depending on the embodiment, the displacement force generation region 512+514 may partially overlap with the isolation region 510, and further may not have a fluidic connector 514 that includes any turns.

In other instances, it may be advantageous to nucleate a bubble 520 that moves through the sequestration pen 502 to enter the channel 522. In some instances, the bubble 520 may be used to export micro-objects into the channel 522. In other instances, the bubble 520 may be used to block the channel 522 (e.g. to prevent micro-objects from moving through the channel 522) and/or redirect a flow 530 of fluidic medium (not shown) in the channel 522. For example, in microfluidic circuits including multiple channels 122 (such as the microfluidic circuit 280 illustrated in FIG. 2F), a bubble 520 may be induced and used as a blocking mechanism to redirect a flow path 106 from a first channel 122 to one of the other channels 122.

Any of the modes of dislodging the micro-objects 504, by bubble flow, shear flow, contact with the meniscus of a bubble, or a cavitating force may be alternatively be practiced using this configuration.

Other methods and techniques may be used in conjunction with optically-driven displacement and export of micro-objects from a sequestration pen into a channel or other circuit element. For example, the tilting apparatus 190 may be used to tilt (i.e. rotate the microfluidic circuit on a horizontal axis) or invert the microfluidic circuit, thereby subjecting the micro-objects to gravitational force, which may be used contemporaneously or as a preliminary step to use of the optically-driven methods. Similarly, in some instances, magnetic beads may be used to disrupt or dislodge micro-objects. In these instances, magnetic beads may be disposed in a sequestration pen and removed using magnetic force. The motion of the magnetic beads as they are removed from the sequestration pen may assist to displace and/or dislodge micro-objects that have become affixed to the sequestration pen.

Figure 5C:
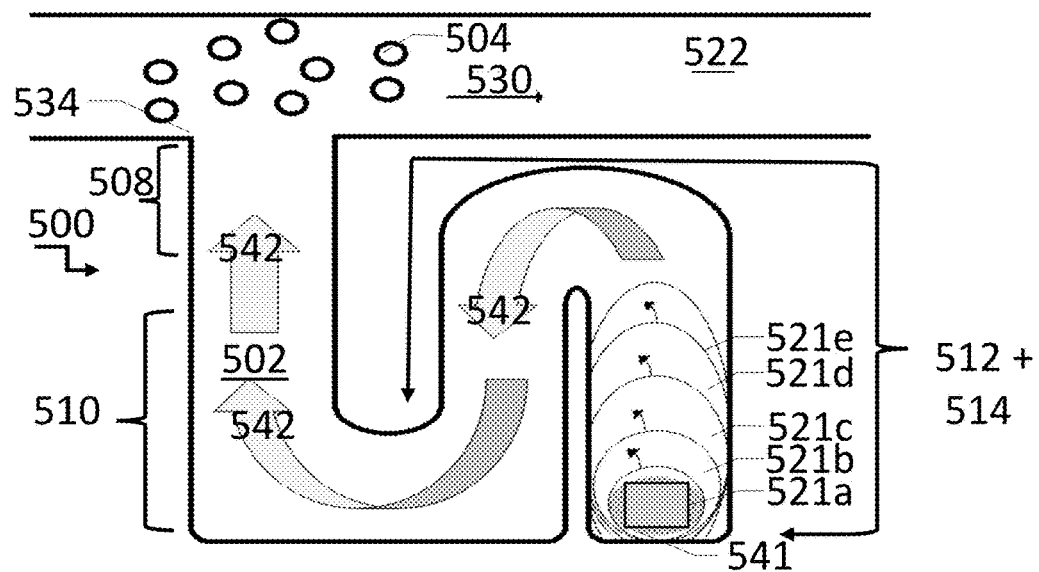

FIG. 5C illustrates the use of optical illumination directed at a thermal target 541, which is simply a selected discrete region of the inner surface of the displacement force generation region, that can be used to generate a bubble 521 in sequestration pen 502 of microfluidic device 500. The selected discrete region forming the thermal target 541 does not require any metal deposition nor any special patterning of the microfluidic circuit material or inner surface of the base. In the embodiment illustrated in FIG. 5C, the light source may be focused on an area of the sequestration pen 502 in a square pattern of light (not shown). This square pattern of light can heat the microfluidic circuit structure 108, the inner surface 109, and/or the cover 110 and thereby creating a thermal target 541 at any selected position, that can be used to nucleate and grow a bubble 521 that generates a shear force 542 sufficient to export micro-objects 504 from the sequestration pen 502. Any of the modes of dislodging the micro-objects 504, by bubble flow, shear flow, contact with the meniscus of a bubble, or a cavitating force may be alternatively be practiced using this configuration.

Figure 5D:
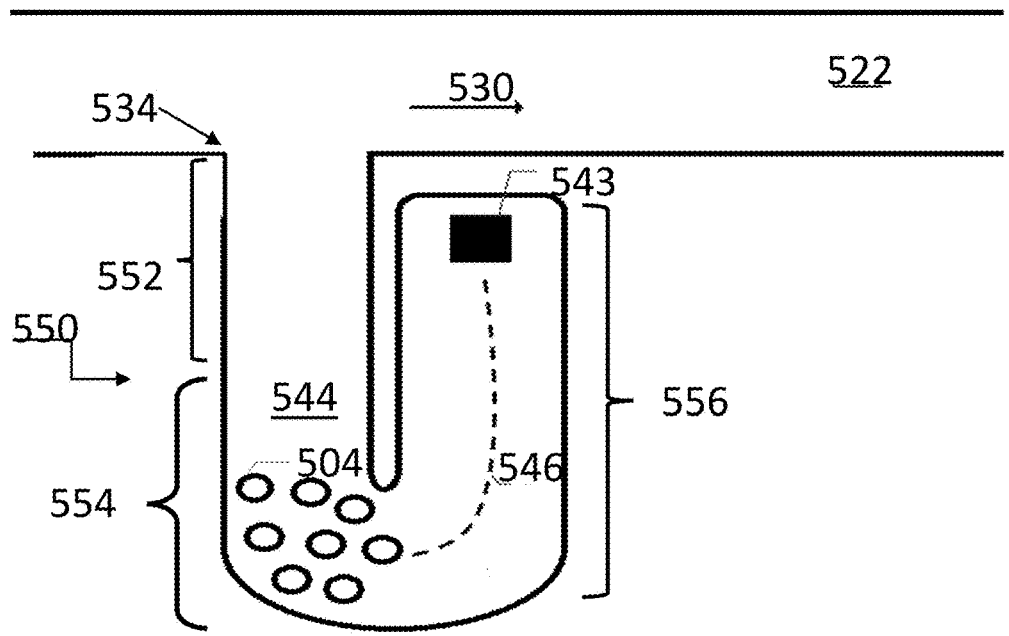

FIG. 5D illustrates a sequestration pen 544 of microfluidic device 550, where repeated number elements are defined as above. The sequestration pen 544 is configured for optically-driven displacement force generation and used to export micro-objects 504 according to some embodiments of the present disclosure. The sequestration pen 544 illustrated in FIG. 5D is characterized by a shape which resembles the letter "U" (i.e., a "U"-like shape), where the isolation region 554 is directly below the proximal opening 534 and the connection region 552. A thermal target 543 is situated at the distal end of the sequestration pen 544, within the displacement force generation region 556. As in FIG. 5A, the displacement force generation region 556 provides sufficient distance between the isolation region 554 and the thermal target 543 to allow for the nucleation of a bubble (not shown) and its use to create a cavitating force, a shear force, a bubble that can contact the micro-objects 504, or a stream of bubbles that can dislodge micro-objects 504 within the isolation region 554, and optionally, displace the micro-objects 504 into the channel 522. The path of the bubbles, shear flow or cavitating forces is illustrated by path 546.

Figure 5E:
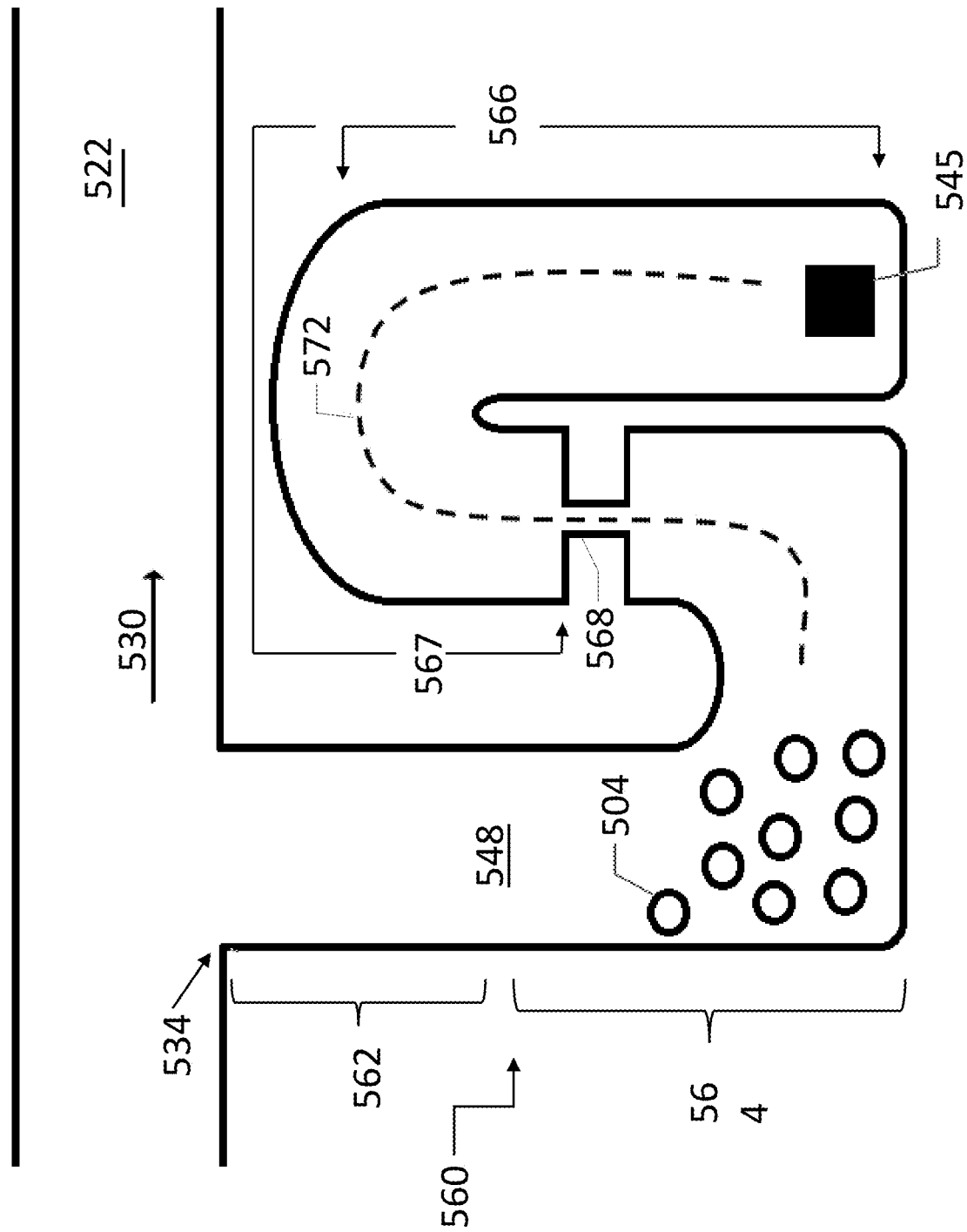

FIG. 5E illustrates a sequestration pen 548 of microfluidic device 560, where repeated numbered elements are defined as above. The sequestration pen 548 is configured for optically-driven displacement force generation and used to export micro-objects 504 according to some embodiments of the present disclosure. The sequestration pen 548 illustrated in FIG. 5E also has a reversed "N" shape similar to the sequestration pen 502 illustrated in FIGS. 5A and 5B. However, the displacement force generation region in this embodiment includes three sub-regions 566, 567, and 568 separating the thermal target 545 and the isolation region 564, which is further connected to connection region 562. The displacement force generation includes a distal portion 566 which also includes the thermal target 545; a first fluidic connector 567 which has the same dimensions as the distal portion 566 of the displacement force generating region/. The displacement force generation region further includes a second constricted fluidic connector 568, which connects to the isolation region 564, wherein the width (dimension in the x-axial plane as viewing the figure) of the fluidic connector 568 is narrowed relative to the first fluidic connector 567 and/or the isolation region 564. The constricted width of the second fluidic connector 567 serves to prevent bubbles generated at the thermal target 545 from coming into contact with micro-objects 504 in the isolation region 564. In addition, the constricted width of the second fluidic connector 567 prevents undesirable secondary flows that can disrupt or create aberrant currents that interfere with a shear flow or a cavitation force used to displace the micro-objects 504. Further, the constricted width of the second fluidic connector 567 prevents passage of micro-objects 504 from the isolation region to the displacement force generation region (566, 567 and 568).

Figure 6A:
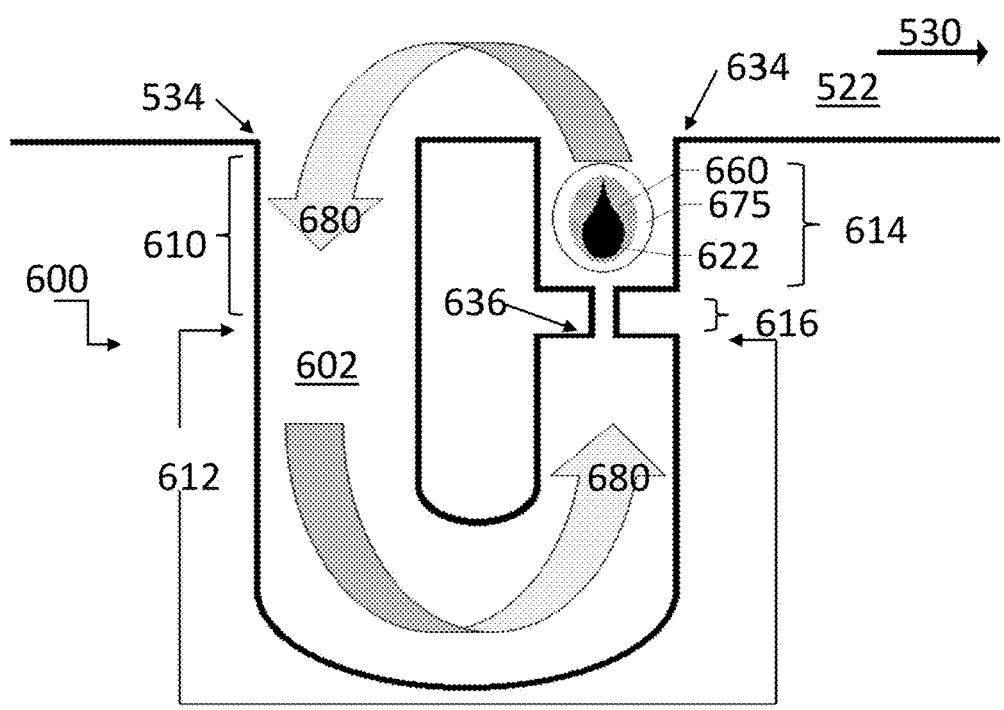
FIGS. 6A-6D are graphical representations of sequestration pens according to some embodiments of the disclosure.

FIG. 6A illustrates a cyclic culturing pen 602 and thermal target 622 of microfluidic device 600 used to create a Marangoni-effect flow 680 according to one embodiment of the disclosure. The thermal target 622 has an asymmetrical teardrop-like shape which when heated using a light source 660, creates a bubble 675 with a temperature gradient that results in a cyclic Marangoni-effect flow 680. As discussed above with respect to FIGS. 4C, 4D, 4E, and 4G, a variety of different asymmetric thermal targets may be used to generate a Marangoni-effect flow 680.

In the embodiment illustrated in FIG. 6A, the portion of the thermal target 622 that contains a larger surface area is positioned below the portion of the thermal target 622 that contains a smaller surface area. Therefore, the resultant Marangoni-effect flow 680 that can be generated by temperature gradient on the bubble moves from the bottom portion of the bubble 675 to the top portion of the bubble 675 (directed towards the proximal opening 634 of the displacement force generation region 614, and away from the fluidic connector 616 of the displacement force generation region 614 plus 616), generating a cyclic, in this instance counter-clockwise, Marangoni-effect flow 680.

In the embodiment illustrated in FIG. 6A, the cyclic culturing pen 602 of microfluidic device 600 has a connection region 610, and culturing region 612 and a displacement force generation region 614 which includes a fluidic connector 616. The cyclic culturing pen 602 may be similar to a sequestration pen, but is configured to cycle flow through the main channel when actively cycling. The displacement force generation region 614 has a proximal opening 634 to the microfluidic channel 522, and a distal opening 636 from its fluidic connector 616 to the culturing region 612. Repeated numbered elements are as defined above. When the thermal target 622 is illuminated with light 660, a bubble 675 is nucleated, developing a cyclic flow 680 (Marangoni-effect flow) cycling through both the cyclic culturing pen 602 and the channel 522. The cyclic flow 680 can be used to mix fluid and/or displace micro-objects (e.g. cells) anywhere in the cyclic culturing pen 602 and adjacent channel 522. The velocity of the flow, and therefore its displacement force, may be moderated by moderating the power of illumination, which may require as little as 1 milliwatt to initiate. In some instances, the cyclic flow 680 may have at least a portion of a vector of flow in the same direction as the flow of medium 530 controlled by the media module 160 and the media source 178. The cyclic flow 680 may be used to flush media in the channel 522 into the culturing region 612. Similarly, the cyclic flow 680 may also be used to displace and export micro-objects in the cyclic culturing pen 602.

In some other embodiments, a sequestration pen may include other geometries which may include a circuit for generating a cyclic (Marangoni-effect) flow 680. While the cyclic culturing pen 602 illustrated in FIG. 6A includes a circuit that incorporates the main channel 522 (referred to herein as an "open-loop" cyclic culturing pen 602), other pen geometries may include a circular portion of microfluidic circuit structure within a sequestration pen to create a "closed-loop" sequestration pen (i.e. a circuit that does not include any portion of the main channel 522).

Depending on the embodiment and the force of the Marangoni-effect flow generated by the bubble, open-loop cyclic culturing pens and closed loop sequestration pens can have different sizes and shapes. For examples, the circuit contained within open-loop and closed-loop sequestration pens may accommodate different volumes of fluid. Similarly, the length of the circuit may vary according to the force of the Marangoni-effect flow 680 and the type of thermal target 622 used. As discussed below with respect to FIG. 8C and FIG. 8D, a circuit may comprise an entire channel.

Figure 6B:
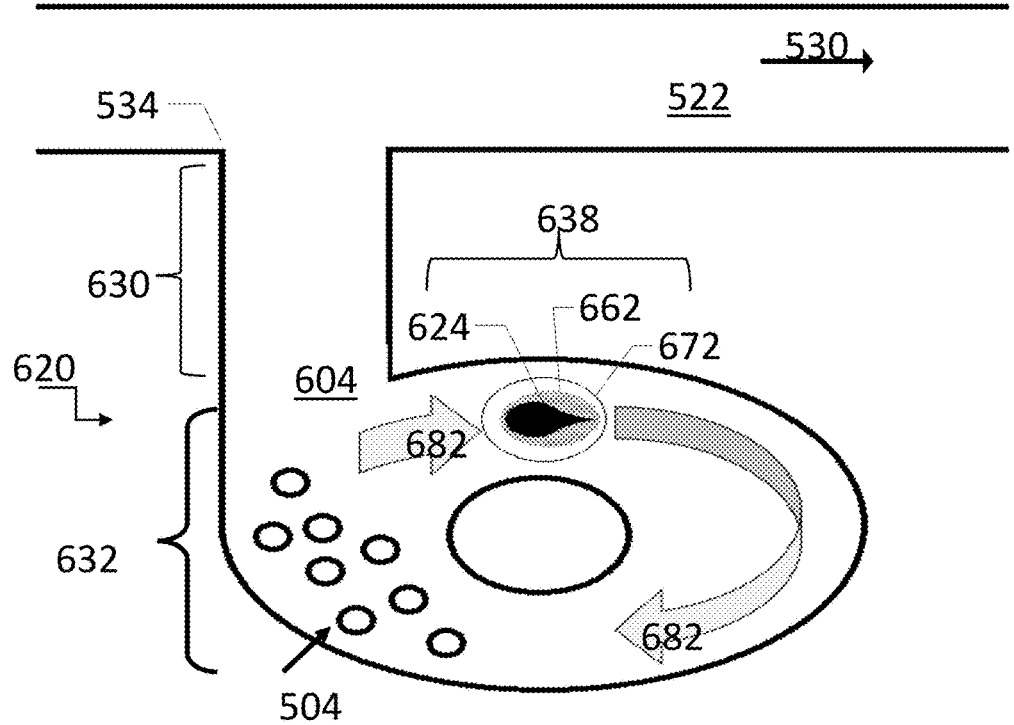

FIG. 6B illustrates a "closed-loop" sequestration pen 604, of microfluidic device 620, configured to generate a cyclic Marangoni-effect flow 682. The sequestration pen 604 has a shape that resembles a lowercase "b" (i.e. a "b"-like shape). In the sequestration pen illustrated in FIG. 6B, the isolation region 632 is positioned directly below connection region 630, which has a proximal opening 534 to the microfluidic channel 522. The closed-loop sequestration pen 604 has a circular channel, however any type of circuit (e.g. a square or a polygonal channel) can be used. The sequestration pen 604 further contains an asymmetrical thermal target 624, which is located within a displacement force generation region 638 having two fluidic connections to the isolation region 632, e.g., the two arms of the circular channel leading from and to the isolation region 630. The thermal target 624 may be heated using a light source 662 to generate a bubble 672 having a temperature gradient, which, in turn, can create a Marangoni-effect flow 682 in the closed-loop circular channel. As the circular channel does not open to the main channel 522, the Marangoni-effect flow 682 may be used to mix objects or fluidic medium independently from the fluidic medium in the main channel 522.

Figure 6C:
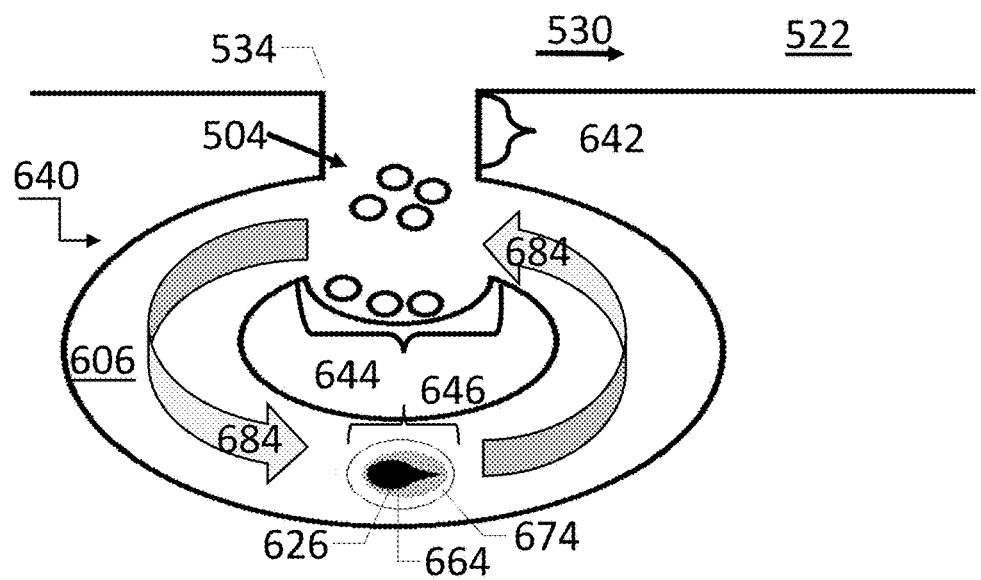

FIG. 6C illustrates a sequestration pen 606 of microfluidic device 640 configured to generate a Marangoni-effect flow 684. The sequestration pen 606 includes an isolation region 664 located directly below a connection region 642, which has a proximal opening 534 to the channel 530. The sequestration pen 606 also surrounds a portion of microfluidic circuit material providing a closed-loop circular channel having two fluidic connections to the isolation region 644 from the displacement force generation region 646. The asymmetrical thermal target 626, within the displacement force generation region 646, can be heating using a light source 664 to generate a bubble 674 with a temperature gradient that generates a Marangoni-effect flow 684.

Figure 6D:
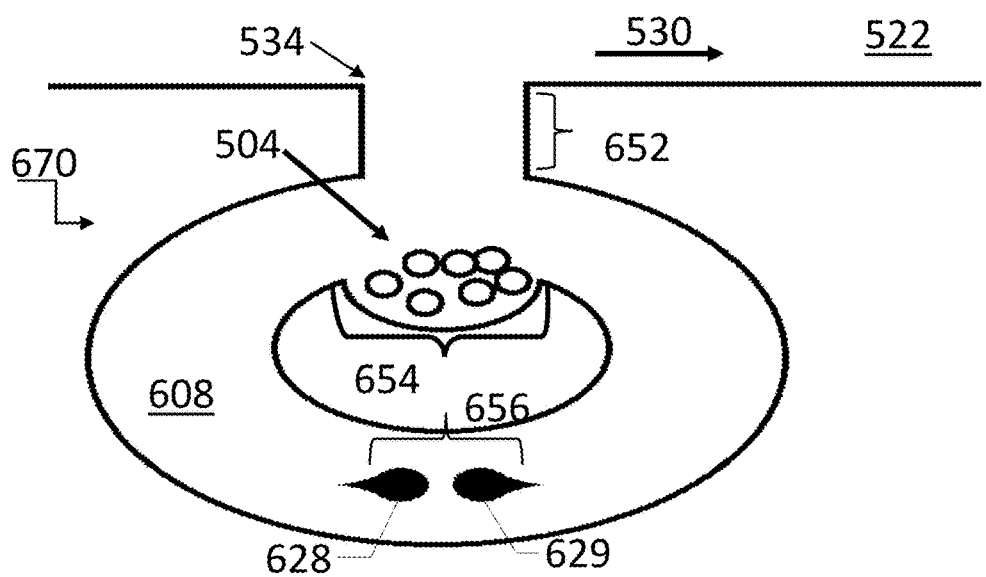

FIG. 6D illustrates a sequestration pen 608 of microfluidic device 670, which is configured to generate Marangoni-effect flows in alternate directions. As for sequestration pen 606 of microfluidic device 640, sequestration pen 608 has an isolation region 654, a displacement force generation region 656 which is connected to the isolation region via two fluidic connections (arms of the cyclic channel), and a connection region 652 having a proximal opening 534 to the channel 522. The sequestration pen 608 has two thermal targets 628, 629 configured to generate Marangoni-effect flows (not shown) in alternate directions. Alternating the direction of Marangoni-effect flow can be used to create an agitating motion on micro-objects or fluidic media in the sequestration pen 608, which may serve to provide an enhanced effect in mixing and dislodging micro-objects and media.

FIGS. 7A-7F illustrate other embodiments of sequestration pens useful for optically-driven convective flow and micro-object displacement. In each of the embodiments shown in FIGS. 7A to 7F, a barrier creates a physical separation of the displacement force generation region from the isolation region of the sequestration pen. The gap between a barrier, which may be a single barrier module or may be a plurality of barrier modules, and a wall of the sequestration pen provides a fluidic connection between the two regions but is configured to prevent passage of a micro-object from the isolation region to the displacement force generation region. Similarly, the gap between a barrier module and an adjacent barrier module provides a fluidic connection between the two regions but is configured to prevent passage of a micro-object from the isolation region to the displacement force generation region. In each case, the barrier module(s) also may be configured to prevent damage to the micro-objects from direct impact of forces generated by the optically-driven convective and displacement forces, and may also assist in channeling shear flow, cavitation force, or bubble force to more effectively dislodge micro-objects within the isolation region. Numbered elements having the same numbers are equivalent.

In FIG. 7A, a sequestration pen 704 of microfluidic device 700, opens off of microfluidic channel 722, which is configured to contain a flow of fluidic medium 706. The microfluidic channel 706 and the walls of the sequestration pen are fabricated from microfluidic circuit material 716. The sequestration pen 704 has a connection region 714 which has a proximal opening 710 to the microfluidic channel 722. The connection region is fluidically connected to an isolation region 712 where micro-objects 702 may be disposed and/or maintained. The isolation region 712 is further connected to displacement force generation region 718, which includes a thermal target 724, which may be any thermal target as described herein. Sequestration pen 704 also includes a single barrier module 726 which forms a boundary between the isolation region 714 and the displacement force generation region 718. There are two fluidic connections between the isolation region 714 and the displacement force generation region 718, which are the gaps 728, between the barrier 728 and the wall of the sequestration pen 704. The sequestration pen 704 may be used in the methods of optically-driven convective flow and micro-object displacement. In some embodiments, the thermal target may be illuminated by a light source, which may be a coherent or a noncoherent light source, and may be structured or unstructured. In some embodiments, the thermal target is an additional feature within the sequestration pen 704 and may be fabricated from metal, patternable microfluidic circuit material, or photoinitiated hydrogel polymer, which may be deposited on the cover above the sequestration pen 704 or may be deposited on the surface of the base 708. In some embodiments, the thermal target fabricated for this purpose is a sacrificial feature. In other embodiments, the discrete selected region that is illuminated is a selected location on the upper surface 708 or the microfluidic circuit material 726 of the walls of the displacement force generation region. Typically, when the upper surface 708 or microfluidic circuit material 716 is illuminated, it behaves as a sacrificial feature, generating heat but also being destroyed by the process. The duration of illumination may determine what kinds of displacement force are being generated. A short pulse as described herein, in one non-limiting example of a range of about 10 microsec to about 200 microsec, may create a cavitation force for displacement. A longer duration of illumination, in one non-limiting example of about 1000 millisec to about 2000 millisec, may provide one of a bubble contact force, a bubble flow force, bubble meniscus force, or a shear flow force which can dislodge one or more micro-objects within the isolation region. 712. The force dislodging the one or more micro-objects may be sufficient to displace the cells entirely from the isolation region into the microfluidic channel 722 or may be sufficient to dislodge the micro-objects from the surface of the isolation region 712, but not enough to export the cells from the sequestration pen 704.

FIG. 7B shows another arrangement where sequestration pen 730 of microfluidic device 720 has a plurality of barrier modules 726a separating the displacement force generation region 718 from the isolation region 712. The displacement force generation region 718 is fluidically connected to the isolation region 712 via a plurality of fluidic connections, gaps 728a.

FIG. 7C represents another variation of a sequestration pen 732 of microfluidic device 740, where a plurality of elongate barrier modules 726b separate the displacement force generation region 718 from the isolation region 712. The displacement force generation region 718 is fluidically connected to the isolation region 712 via a plurality of fluidic connections, gaps 728b.

FIG. 7D is yet another variation, having a sequestration pen 734 of microfluidic device 750. A single barrier module 726c, has an arc in its configuration which may protect the micro-objects from direct impact. The displacement force generation region 718 is fluidically connected to the isolation region 712 via two fluidic connections, gaps 728c.

FIG. 7E is a further variation, having a sequestration pen 736 of microfluidic device 760. A single barrier module 726d, has a narrowing protrusion in its configuration which may help direct the displacing forces more effectively to displace the micro-objects. The displacement force generation region 718 is fluidically connected to the isolation region 712 via two fluidic connections, gaps 728d.

FIG. 7F represents another variation of a sequestration pen 738 of microfluidic device 780, where a plurality of barrier modules 726e define the displacement force generation region 718 as a circular region surrounding the thermal target 724 and separate the region 718 from the isolation region 712. The displacement force generation region 718 is fluidically connected to the isolation region 712 via a plurality of fluidic connections, gaps 728e.

Sequestration pens 730, 732, 734, 736 and/or 738 may be fabricated in any similar manner to the fabrication of sequestration pen 704, and may be employed in any method of optically-driven convective flow and/or micro-object displacement as the methods described for sequestration pen 704.

Figure 8A:
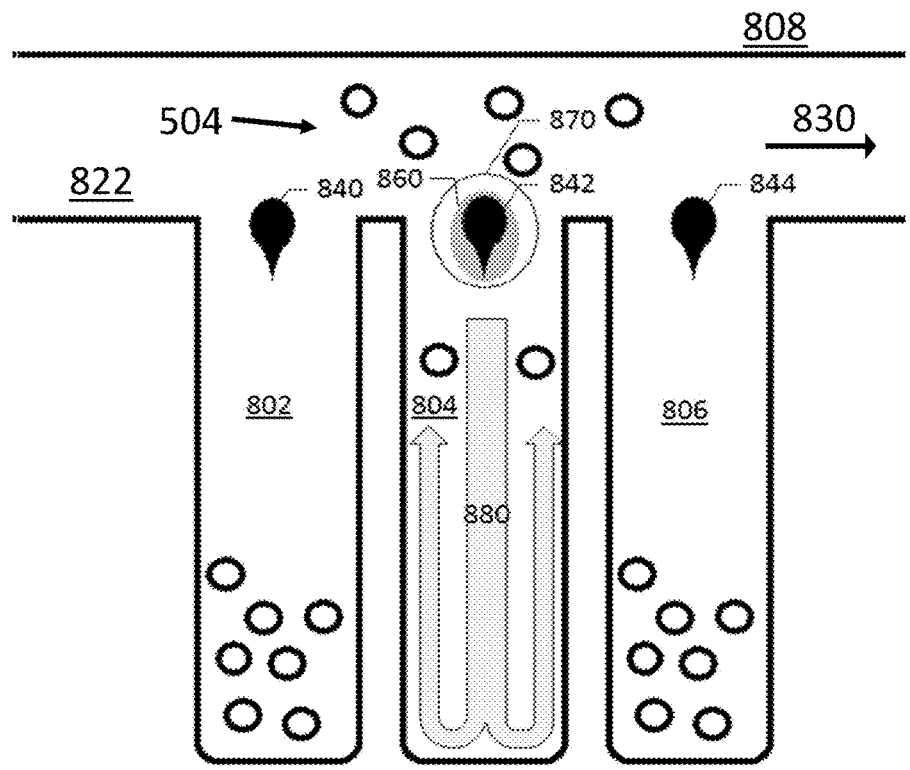
FIGS. 8A-8D illustrate microfluidic devices according to some embodiments of the disclosure.

FIG. 8A illustrates a microfluidic device comprising a series of sequestration pens 802, 804, 806 with asymmetrical thermal targets 840, 842, 844 situated within the channel and extending into the sequestration pens 802, 804, 806. A thermal target 842 may be heated using a light source 860 to nucleate a bubble 870 with a temperature gradient which, in turn, creates a Marangoni-effect flow 880 which can be used to disrupt or displace micro-objects 504 in the sequestration pen 804 into the channel 822, creating a cyclized flow within the sequestration pen 804. The Marangoni-effect flow 880 can also be used to introduce fluidic media from the channel 822 into the sequestration pen 804. Although the thermal targets 840, 842, 844 illustrated in FIG. 8A are positioned above the sequestration pens 802, 804, 806 and can be used to introduce fluidic media into unswept portions of the sequestration pens 802, 804, 806, thermal targets configured to produce a Marangoni-effect flow 880 may be positioned anywhere in the microfluidic circuit where it is beneficial to introduce fluid from a swept region to an unswept region. The velocity, and resultant force of the cyclized flow may be modulated by increasing or decreasing the power of the illumination, thereby speeding or slowing the velocity of the cyclized flow.

Figure 8B:
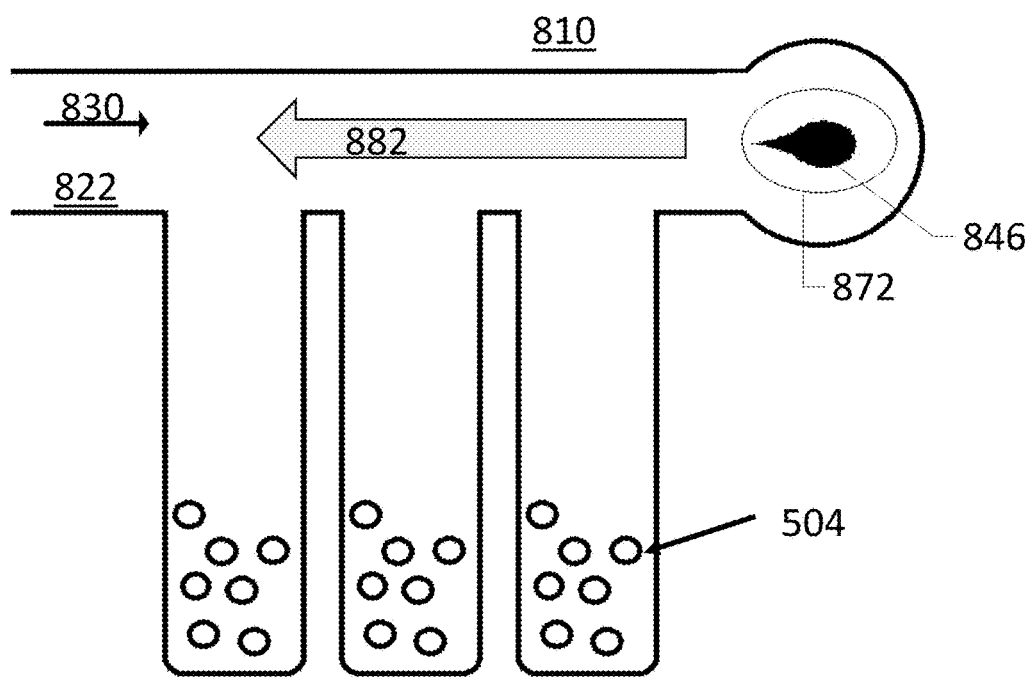

FIG. 8B illustrates a microfluidic device 810 having an asymmetrical thermal target 846 placed at the terminus of a channel 822. When the thermal target 846 is used to generate a bubble 872 with a temperature gradient, the resultant Marangoni-effect flow 882 can be used in place of, or in combination with, the flow path 830 in the channel to move objects within the channel 822.

Figure 8C:
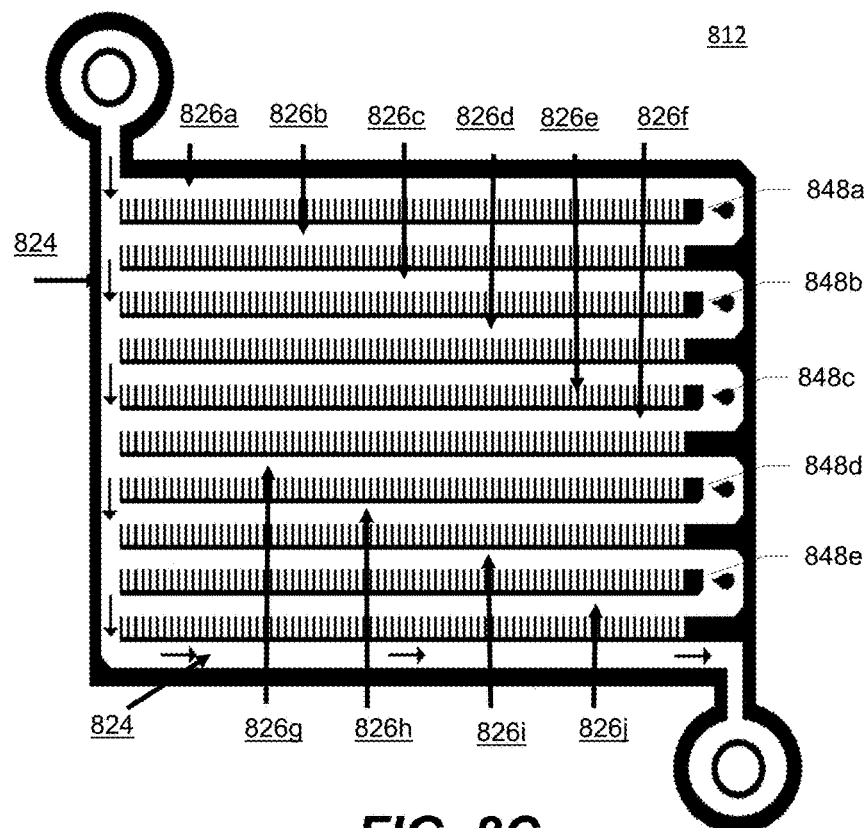

FIG. 8C illustrates another microfluidic device 812 which includes a main channel 824 and ten side channels 826a-j extending perpendicularly from the main channel 824. Each of the ten side channels connects to another side channel to form a microfluidic circuit with the main channel 824. Specifically, 826*a* connects with 826*b*, 826*c* connects with 826*d*, 826*e* connects with 826*f*, 826*g* connects with 826*h*, and 826*i* connects with 826*j* to form circuits. Each of the five microfluidic circuits so formed includes an asymmetrical thermal target 848*a-e* configured to generate a bubble that causes a Marangoni effect flow. In the embodiment illustrated in FIG. 8C, there is a much lower fluidic resistance in the main channel 824 than the side channels 826*a-e*. Due to the difference in fluidic resistance between the main channel 824 and the side channels 826*a-e*, a flow of fluidic media introduced into the main channel 824 will not enter the side channels 826*a-e*. In other words, the side channels 826*a-e* are unswept regions of the microfluidic device 812, in the absence of the cyclized flow induced by optical illumination.

Depending on the embodiment, the ratio of fluidic resistance between the main channel 824 and the side channels can vary. In most embodiments, the fluidic resistance in the main channel 824 at the point at which it branches into the side channel 826 will be 10 to 100 times lower than the fluidic resistance of the side channel 826. Since fluidic resistance is proportional to the length of the channel and inversely proportional to the width of a channel, the side channels will typically be longer and narrower than the main channel to achieve the optimal ratio of fluidic resistance between the main channel and the side channels. In some embodiments, the main channel can be 1.5 to 3 times wider than the side channels. For example, the main channel can have a width ranging from 100 microns to 1000 microns and the side channel can have a width ranging from 20 microns to 300 microns.

Figure 8D:
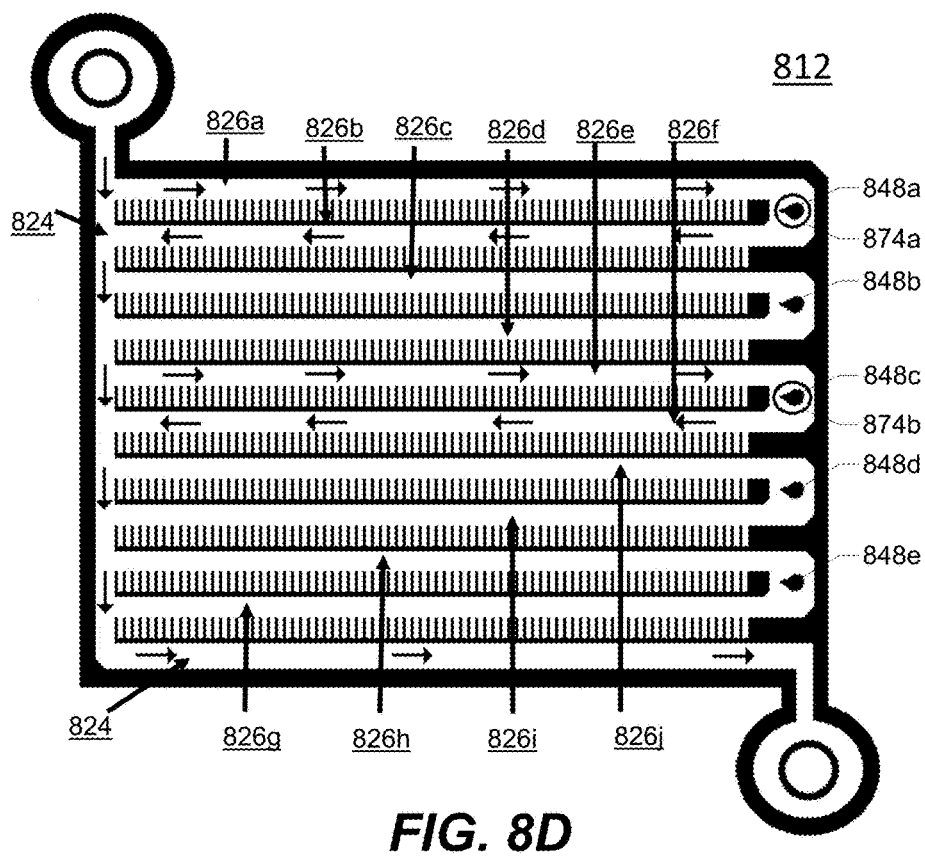

However, as illustrated in FIG. 8D, when bubbles 874*a* and 874*b* are generated using asymmetrical thermal targets 848*a* and 848*c*, the resultant Marangoni-effect flows generated by the bubbles 874*a* and 874*b* may be used in conjunction with the flow in the main channel 824 to selectively introduce fluidic media from the main channel 824 to the side channels 826*a*, 826*b*, 826*e*, 826*f*. In this way, the Marangoni-effect flows may be used to selectively introduce media containing analytes, reagents and or micro-objects (e.g. beads) into channels of interest to perform assays or culture micro-objects.

Kits.

Kits are provided for optically driven devices and methods of convective flow and/or micro-object displacement, which includes any microfluidic device as described herein, where the microfluidic device may include any features described herein in any combination, and reagents for providing a coated surface. The microfluidic device may be selected from any of microfluidic devices 100, 200, 230, 250, 280, 290, 500, 550, 560, 600, 620, 640, 670, 700, 720, 720, 750, 760, 780, 808, 810, 812, 900, 1000, 1100, 1200, 1300, 1400, 1500. The reagents for a coated surface may be any reagent as described herein for that purpose. The reagent for providing a coated surface may include a reagent that provides a covalently linked surface.

In some embodiments of the kit, one or more fluidic media may be provided. In other embodiments, the kit may include a photoactivatable hydrogel, which may be already formulated as a flowable polymer or may be a dry powder or lyophilized product. In some embodiments, the kit may further include a photoinitiator. The components of the kit may be provided in one or more containers.

Method of Fabricating Sequestration Pens Having Thermal Targets.

Thermal targets may be fabricated during the routine manufacture of the microfluidic devices. Metal targets may be deposited on the cover of the microfluidic devices during the same operation that adds metallic contacts for electrical connections and the like. Thermal targets fabricated from microfluidic circuit material may be included in the mask during soft lithography. Thermal targets installed in this fashion may include sacrificial targets. Surface topographies for bubble generation may be patterned into the microfluidic circuit structure 108 or cover 110 during fabrication or may be patterned in situ using a light source (not shown). In embodiments where a patternable material is used, a structured light source may be used. Hydrogel thermal targets may be installed after the microfluidic device has been fabricated but before use in the methods of the disclosure.

Methods of Dislodging One or More Micro-Objects and/or Mixing Fluidic Medium.

Accordingly a method is provided for dislodging one or more micro-objects (e.g., a biological micro-object such as a cell) from a surface within a microfluidic device, illuminating a selected discrete region containing or adjacent to one or more micro-objects disposed within a fluidic medium in an enclosure of the microfluidic device, wherein the enclosure comprises a microfluidic circuit including a flow region and a substrate; maintaining the illumination of the selected discrete region of a first period of time sufficient to generate a dislodging force, dislodging the one or more micro-objects from the surface.

The method may include a step of maintaining the one or more micro-objects within the fluidic medium in the enclosure for a second period of time before performing the step of illuminating the selected discrete region. During maintenance of the cells within the fluidic medium within the enclosure, some types of cells may become attached to one or more internal surfaces of the enclosure of the microfluidic device. The attachment may be non-specific or a specific interaction between the cells and the one or more surfaces. A specific interaction may include a covalent or non-covalent attachment of a surface moiety such as a carboxylic acid of a cell with an oxide moiety of the surface, which may form hydrogen bonds or ester bonds upon association. The attachment of the one or more cells may be direct or non-direct to the one or more surfaces. A non-limiting example of a direct attachment would be an interaction of a portion of the one or more cells with an oxide moiety of a surface having oxide moieties upon the surface. A non-limiting example of an indirect attachment of the one or more cells with a surface may include an interaction between a portion (including but not limited to a moiety on the surface of a cell) of the cell with an intervening substance or material that has itself become associated with the surface, such as, but not limited to, surface fouling proteins produced by other cells present within the enclosure. These are non-limiting examples of the types of attachment possible between cells and the surfaces upon which the cells are maintained. Attachment of any kind may decrease the portability of one or more cells.

In various embodiments, the enclosure of the microfluidic device may further include at least one sequestration pen. In some embodiments, the microfluidic device may include a plurality of sequestration pens. Each of the plurality of sequestration pens may have a proximal opening to the flow region. In some embodiments, the flow region may include a microfluidic channel.

In some embodiments, the surface upon which the one or more micro-objects are maintained may be a surface of the substrate. The surface of the substrate upon which the one or more micro-objects are maintained may be a surface of the substrate within the at least one sequestration pen.

In various embodiments, the step of illuminating a selected discrete region may include illuminating a region having a first dimension (e.g., width or x-axial dimension of the microfluidic enclosure) of about 1 mm, 0.9 mm, 0.7 mm, 0.5 mm, 0.3 mm, 100 microns, 80 microns, 60 microns, 40 microns, 20 microns, about 10 microns, about 5 microns or any value therebetween. The step of illuminating a selected discrete region may further include illuminating a region having a second dimension (e.g., a height or y-axial dimension within the microfluidic enclosure) of about 1 mm, 0.9 mm, 0.7 mm, 0.5 mm, 0.3 mm, 100 microns, 80 microns, 60 microns, 40 microns, 20 microns, about 10 microns, about 5 microns or any value therebetween. The x-axial and y-axial dimensions may be any combination of the dimensions as above. The selected discrete region of illumination may have an area of about 200 square microns, about 150 square microns, about 100 square microns, about 80 square microns, about 70 square microns, about 50 square microns, about 25 square microns, about 10 square microns, or any value therebetween.

Period of Illumination.

The step of illumination may be performed using any light source as described herein, and may be a coherent or a non-coherent light. The light may be structured or unstructured light. For simplicity, the following description refers to laser illumination, but the invention is not so limited.

In various embodiments, the step of illuminating the selected discrete region may include illuminating the selected discrete region with a laser. The laser may irradiate with light having a wavelength in the region of about 450 nm to about 800 nm. The laser may have a current of about 0.5 amps, 0.7 amps, 0.9 amps, 1.1 amps, 1.4 amps, 1.6 amps, 1.6 amps, 2.0 amps, 2.2 amps, 2.5 amps, 2.7 amps, 3.0 amps, or any value therebetween.

The laser illumination may have incident power in the range of about 1 mW to about 1000 mW, about 100 mW to about 1000 mW, about 100 mW to about 800 mW, about 100 mW to about 600 mW, about 100 mW to about 500 mW, or any range or individual value therebetween.

In various embodiments, the step of illuminating the selected discrete region with laser illumination may be performed for a period of time in a range of about 10 microsec to about 8000 millisec, and may be any value therebetween. In some other embodiments, the step of illuminating the selected discrete region may be performed for a period of time in the range of about 100 millisec to about 3 minutes.

In various embodiments, the laser illumination may be directed to the selected discrete region for about 50 millisec, 75 millisec, 100 millisec, 150 millisec, 250 millisec, 500 millisec, 750 millisec, or about 1000 millisec. In various embodiments, the laser illumination may be directed to the selected discrete region for a period of time in a range of about 50 millisec to about 2000 millisec; about 50 millisec to about 1000 millisec; about 50 millisec to about 500 millisec; about 50 millisec to about 300 millisec; 100 millisec to about 1000 millisec; about 200 millisec to about 1000 millisec; about 200 millisec to about 700 millisec; about 300 millisec to about 600 millisec; or any value therebetween of any of the ranges. In other embodiments, the laser illumination may be directed to the selected discrete region for a period of time in a range of about 1 millisec to about 200 millisec; about 1 millisec to about 150 millisec; about 1 millisec to about 100 millisec; about 1 millisec to about 50 millisec; about 1 millisec to about 30 millisec; about 25 millisec to about 200 millisec; about 25 millisec to about 100 millisec; about 25 millisec to about 75 millisec; about 50 millisec to about 200 millisec; about 50 millisec to about 125 millisec; about 50 millisec to about 90 millisec; or may be any value therebetween of any of the ranges. A period of illumination selected in one of these ranges may be sufficient to optically drive generation of a bubble which can contact a micro-object and thereby dislodge it.

In various other embodiments, the laser illumination may be directed to the selected discrete region for a period of time in a range of about 500 millisec to about 3000 millisec; about 1000 millisec to about 2700 millisec; about 1000 millisec to about 2500 millisec; about 1000 millisec to about 2000 millisec; about 1000 millisec to about 1500 millisec; about 1300 millisec to about 3000 millisec; about 1300 millisec to about 2700 millisec; about 1300 millisec to about 2300 millisec; about 1300 millisec to about 2000 millisec; about 1300 millisec to about 1700 millisec; about 1500 millisec to about 3000 millisec; about 1500 millisec to about 2600 millisec; about 1500 millisec to about 2300 millisec; about 1500 millisec to about 2000 millisec; about 1700 millisec to about 3000 millisec; about 1700 millisec to about 2600 millisec; about 1700 millisec to about 2000 millisec; or any value therebetween. A period of illumination chosen in one of these ranges may be suitable for generating optically-driven shear flow or bubble flow contact force.

In yet other embodiments, the step of illuminating the selected discrete region may be performed for about 10 microsec to about 200 millisec; about 10 microsec to about 100 millisec; about 10 microsec to about 1 millisec; about 10 microsec to about 1 millisec; about 10 microsec to about 500 microsec; about 50 microsec to about 1 millisec; about 50 microsec to about 500 microsec; about 50 microsec to about 300 microsec; about 1 millisec to about 200 millisec; about 1 millisec to about 150 millisec; about 1 millisec to about 100 millisec; about 1 millisec to about 50 millisec; about 1 millisec to about 30 millisec; about 25 millisec to about 200 millisec; about 25 millisec to about 100 millisec; about 25 millisec to about 75 millisec; about 50 millisec to about 200 millisec; about 50 millisec to about 125 millisec; about 50 millisec to about 90 millisec; or may be any value therebetween of any of the ranges. A period of illumination in one such range of illumination may be sufficient to create a cavitating force within a discrete select region containing or adjacent to micro-objects, thereby dislodging one or more of the micro-objects. In some embodiments, the period of time of illumination may be in a range from about 10 microsec to about 500 microsec or from about 10 microsec to about 100 millisec.

In some other embodiments, the step of illuminating the selected discrete region may be performed for about 100 millisec to about 3 minutes; about 100 millisec to about 2 minutes; about 100 millisec to about 1 minute; about 100 millisec to about 10,000 millisec; about 100 millisec to about 5,000 millisec; about 100 millisec to about 1000 millisec; about 500 millisec to about 3 minutes; about 500 millisec to about 1 minute; about 500 millisec to about 10,000 millisec; about 500 millisec to about 3,000 millisec; or any value therebetween. A period of illumination in a range selected from one of these ranges may be sufficient to create a cyclized flow (Marangoni effect) for mixing fluidic media and/or micro-objects. The period of illumination for cyclized flow may be lengthened or shortened, depending on the power used to illuminate the discrete selected region.

These ranges are exemplary only and are not intended to limit the disclosure. Periods of illumination outside of the ranges described for each type of convective flow or displacement force may be identified and used while still remaining within the scope of the disclosure.

In some embodiments, the step of illuminating a discrete region includes directing laser illumination at a selected discrete region containing at least one of the one or more micro-objects. This may be performed anywhere within the enclosure of the microfluidic device. In some embodiments, the discrete region that is illuminated may be within a sequestration pen, and may further be a surface of the substrate within the sequestration pen. When illuminating at least one micro-object of the one or more micro-objects within a sequestration pen, the selected discrete region may be selected to be at a location distal to a proximal opening of the sequestration pen (e.g., at the bottom or base of the sequestration pen) to the flow region or at a central location within the at least one sequestration pen).

The laser illumination may directly cause a dislodging force upon at least one of the one or more micro-objects. Without being bound by theory, the illumination may also or alternatively, heat a portion of the fluidic medium around the one or more micro-objects and create a cavitating dislodging force which can dislodge at least some of the one or more micro-objects.

In other embodiments of the method, the selected discrete region to be illuminated may be adjacent to the one or more micro-objects. The selected discrete region may be located about 1 mm, 0.9 mm, 0.7 mm, 0.5 mm, 0.3 mm, 100 microns, 80 microns, 60 microns, 40 microns, 20 microns, about 10 microns, about 5 microns or any value therebetween, away from the one or more micro-objects to be dislodged. The laser illumination adjacent to the one or more micro-objects may be performed anywhere within the enclosure of the microfluidic device. In some embodiments, the step of illuminating the selected discrete region adjacent to the one or more micro-objects may be performed on the substrate; on microfluidic circuit material of a wall; or a thermal target, which may be any thermal target described herein which may further be a sacrificial feature. In some embodiments, when the one or more micro-objects are maintained within a sequestration pen, the step of illuminating the substrate may be performed on a selected discrete region on the substrate near a proximal opening of the at least one sequestration pen to the flow region. In other embodiments, when the one or more micro-objects are maintained within the at least one sequestration pen, the step of illuminating the selected discrete region may include illuminating a selected discrete region of microfluidic circuit material of the at least one sequestration pen. In yet other embodiments, when the one or more micro-objects are maintained within the at least one sequestration pen, the step of illuminating the selected discrete region may include illuminating a sacrificial feature disposed within the at least one sequestration pen.

A sacrificial feature may be made of any suitable material that may absorb energy from the laser illumination, which can include a metal pad or microfluidic circuit material (e.g., the same or similar material as that of the sequestration pen walls and the walls of the flow region (e.g., microfluidic channel). In some embodiments, the sacrificial feature may include the upper surface of the substrate (which may or may not include additional coatings or covalently modified surface layers) or any other material that may be included within the microfluidic device.

The illumination (e.g., including but not limited to laser illumination) may directly cause a dislodging force upon at least one of the one or more micro-objects. Without being bound by theory, the illumination may also or alternatively, heat a portion of the fluidic medium around the one or more micro-objects and create a cavitating dislodging force which can dislodge the one or more micro-objects.

The laser illumination may directly cause a dislodging force upon at least one of the one or more micro-objects. Without being bound by theory, the step of illuminating the selected region adjacent to the one or more micro-objects may also or alternatively, heat a first portion of the fluidic medium; and, create a persistent bubble displacing a second portion of the fluidic medium surrounding the one or more micro-objects, thereby dislodging the one or more micro-objects. The step of displacing a second portion of the fluidic medium may further include creating a cyclic fluidic flow of the fluidic medium during the first period of illumination. In other embodiments, the method may further include heating a first portion of the fluidic medium; and creating one or more gaseous bubbles, thereby creating a shear flow of the fluidic medium towards the one or more micro-objects. In yet other embodiments, the method may further include heating a first portion of the fluidic medium; creating a plurality of gaseous bubbles configured to stream towards the one or more micro-objects; and contacting the one or more micro-objects with a meniscus of at least one gaseous bubble of the plurality of gaseous bubbles.

The laser illumination may be directed anywhere as described above. Alternatively, when the one or more micro-objects are maintained within a sequestration pen within the enclosure, the selected discrete may include at least a part of a wall forming a distal end of the sequestration pen, wherein the wall is positioned opposite to a proximal opening to the flow region. Illumination at the base of the sequestration pen may prevent damage to the one or more micro-objects.

Alternatively, when the one or more micro-objects are disposed within a sequestration pen within the enclosure, the selected discrete region may be located in a displacement force generation region of the sequestration pen. In some embodiments, the one or more micro-objects may be disposed within an isolation region of the sequestration pen and the displacement force generation region is fluidically connected to the isolation region.

In various embodiments of the method for dislodging one or more micro-objects within a microfluidic device, the method may further include a step of exporting the one or more micro-objects from the at least one sequestration pen. The step of exporting the one or more micro-objects from the at least one sequestration pen may include moving the one or more micro-objects with dielectrophoresis force.

In various embodiments of the method for dislodging one or more micro-objects within a microfluidic device, the method may further include a step of exporting the one or more micro-objects from the flow region of the enclosure of the microfluidic device. The step of exporting the one or more micro-objects from the flow region may include using gravity, fluidic flow, dielectrophoresis forces, or any combination thereof.

In certain embodiments, the disclosure further provides machine-readable storage devices for storing non-transitory machine readable instructions for carrying out the foregoing methods. The machine-readable instructions can further control the imaging device used to obtain the images.

In another aspect, a method is provided for mixing fluidic media, and/or micro-objects contained therein, within an enclosure of a microfluidic device, the method including the steps of: focusing a light source on a thermal target disposed on a surface of the enclosure within a microfluidic circuit including at least one fluidic medium and/or micro-objects, thereby heating a first portion of the at least one fluidic medium; and inducing a cyclic flow of the at least one fluidic medium within the microfluidic circuit thereby mixing the fluidic media and/or micro-objects disposed therein. In some embodiments of the method, wherein the thermal target is disposed within a first microfluidic channel, which is configured to branch off of a second fluidic channel at a first location and is also configured to rejoin the second fluidic channel at a second location, wherein the thermal target is disposed on the surface therebetween.

Experimental

System and Microfluidic Device:

Manufactured by Berkeley Lights, Inc. The system included at least a flow controller, temperature controller, fluidic medium conditioning and pump component, light source for light activated DEP configurations, laser, mounting stage for a Berkeley Lights, Inc. OptoFluidic™ microfluidic device, and a camera. The Berkeley Lights, Inc. Optofluidic™ microfluidic device included NanoPen™ chambers having a volume of about $7 \times 10^5$ cubic microns.

Materials:

Cells, unless otherwise noted, were OKT3 cells, a murine myeloma hybridoma cell line, which were obtained from the ATCC (ATCC® Cat. # CRL-8001™). The cells were provided as a suspension cell line. Cultures were maintained by seeding about $1 \times 10^5$ to about $2 \times 10^5$ viable cells/mL and incubating at 37° C., using 5% carbon dioxide in air as the gaseous environment. Cells were split every 2-3 days. OKT3 cell number and viability were counted and cell density was adjusted to $5 \times 10^5$/ml for loading to the microfluidic device.

Culture Medium:

500 ml Iscove's Modified Dulbecco's Medium (ATCC® Catalog No. 30-2005), 200 ml Fetal Bovine Serum (ATCC® Cat. #30-2020) and 1 ml penicillin-streptomycin (Life Technologies® Cat. #15140-122) were combined to make the culture medium. The complete medium was filtered through a 0.22 micron filter and stored away from light at 4° C. until use.

Priming Procedure:

250 microliters of 100% carbon dioxide was flowed in at a rate of 12 microliters/sec. This was followed by 250 microliters of PBS containing 0.1% Pluronic® F27 (Life Technologies® Cat# P6866), flowed in at 12 microliters/sec. The final step of priming included 250 microliters of PBS, flowed in at 12 microliters/sec. Introduction of the culture medium follows.

Perfusion Regime (During Cell Culturing on Chip:

The perfusion method was either of the following two methods:

1. Perfuse at 0.01 microliters/sec for 2 h; perfuse at 2 microliters/sec for 64 sec; and repeat.
2. Perfuse at 0.02 microliters/sec for 100 sec; stop flow 500 sec; perfuse at 2 microliters/sec for 64 sec; and repeat.

Optical System.

For Examples 1 and 2, the optical system included a 785 nm laser, Olympus microscope Prosilica camera and an epifluorescence light train with specialized collimation optics for the laser.

Example 1. Optical Illumination of a Metal Thermal Target

Figure 9D:
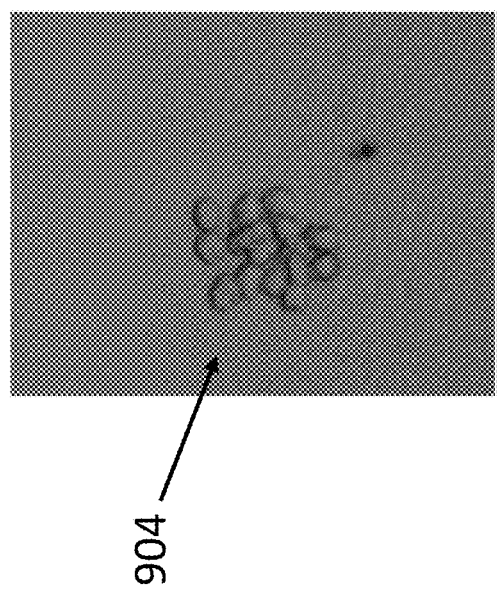

FIGS. 9A-D depict the use of a thermal target to generate bubbles used to export cells from a sequestration pen. The sequestration pen 902 of microfluidic device 900 shown in FIGS. 9A-9C had a reverse "N"-like geometry similar to the sequestration pen illustrated in FIG. 5A, and includes a connection region 906, isolation region 908 where human hybridoma cells 904 were cultured; and a displacement force generation region 910 (labeled in FIG. 9C) including a tripartite fluidic connector 909 having a proximal narrowed segment 912, connecting to the isolation region, and a distal narrowed segment 914 connecting to the reservoir region 913 of the displacement force generation region 910. The proximal narrowed segment 912 of the displacement force generation region 910 has a width that is smaller than a diameter of the cell, and prevents any cells from migrating from the isolation region 908 to the displacement force generation region 910, in particular segregating the cells from the reservoir region 913, where the optical illumination is focused and heating is most intense. The displacement force generation region further includes a thermal target 916 in the reservoir region 913, a contiguous metal shape formed from gold (Au) that had been deposited onto the inner surface of the cover of the microfluidic device. FIG. 9A showed the sequestration pen with a plurality of cells after culturing in the isolation region for three days prior to optical illumination.

Figure 9C:
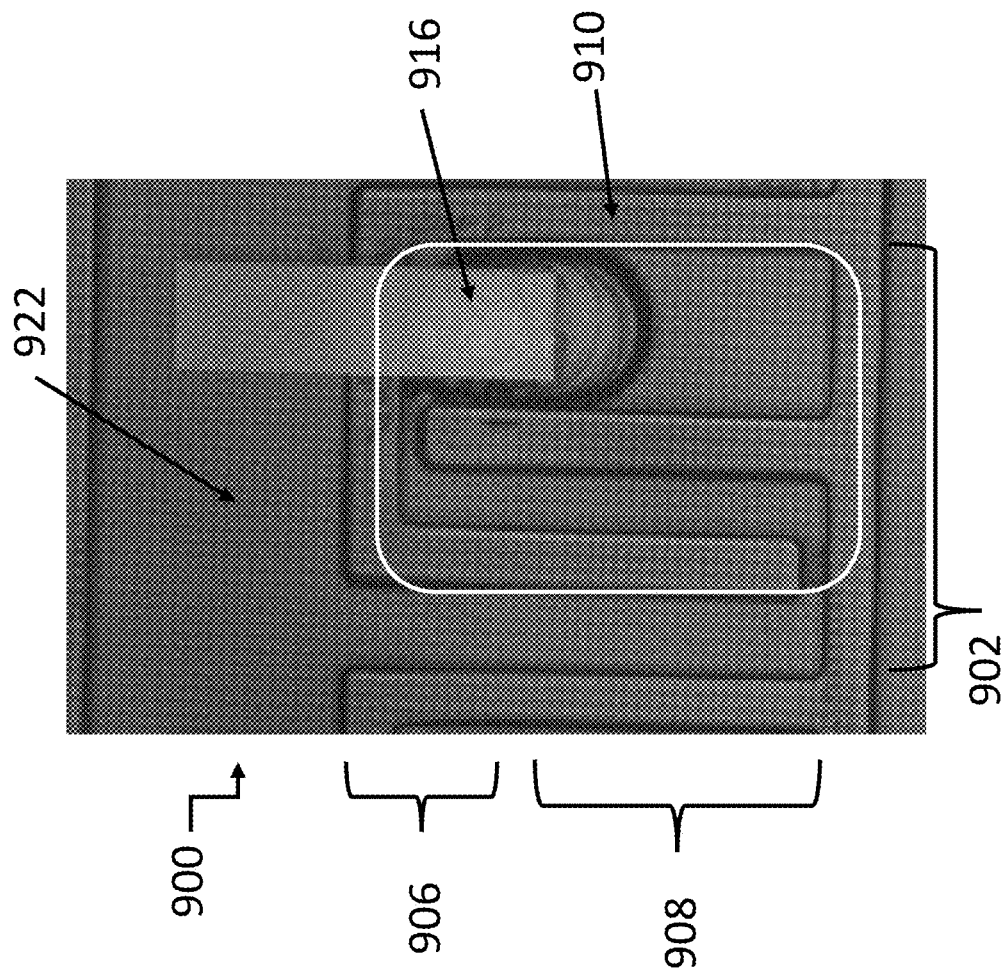

The thermal target was heated for 5-10 seconds using a 785 nm laser with a current ranging from 0.8-1.0 Amperes. FIG. 9B is a photograph taken at a timepoint within the illumination period, where a bubble (not shown) had formed at the thermal target 916 which displaced the cells from the isolation region 908 and exported the cells 904 into the connection region 906 as well as the microfluidic channel 922 proximate to the sequestration pen 902. FIG. 9C depicts the sequestration pen at a time point after the cells have been exported. Exported cells 904 were transferred to a standard wellplate, and plated individually. After three days of culturing within the wellplate, the cells 904 demonstrated viability by expanding into a larger cell population (FIG. 9D.)

Example 2. Optical Illumination of a Sacrificial Feature to Generate Bubble Flow Forces FIGS. 10A and 10B demonstrated the export of human hybridoma cells from a sequestration pen 1002, having a connection region 1006 and an isolation region 1008. In this example, the sequestration pen did not have a distinct or separate displacement force generation region.

The cells were cultured within sequestration pen 1002 of microfluidic device 1000 for three days (not shown). The export was performed by focusing the laser (power was 90 milliwatt) with a 1.4 Ampere current on the inner surface (thermal target) of the microfluidic circuit, which was a dielectrophoresis substrate and the cover comprising indium tin oxide ("ITO") for 5-10 seconds. The specific location illuminated was a discrete selected point 1020 of the inner surface at the base of the sequestration pen 1002, opposite the opening of the sequestration pen to the microfluidic channel 1022. The thermal target was the substrate which absorbed the optical illumination, converted the illumination to thermal energy, and thereby heated the surrounding fluidic medium. In this process, a portion of the substrate was destroyed, acting as a sacrificial feature. The fluidic medium was heated sufficiently to nucleate a stream of gaseous bubbles. FIG. 10A showed a time point during the period of illumination as a bubble 1024 was formed at the bottom of the sequestration pen 1002 by focusing light on the substrate. The cells 1004 have been moved from the isolation region 1008 into the connection region 1006 the sequestration pen. FIG. 10B showed the sequestration pen 1002 at a later time point, where a stream of bubbles 1024 has grown in volume and the majority of cells 1004 have been exported from the pen 1002 into the microfluidic channel 1022. The exported cells 1004 were transferred to a wellplate, and singly seeded for further culturing. FIG. 10C shows one well of the wellplate after 3 days, showing that the singly seeded cell was viable and had expanded.

Optical System for Examples 3 and 4.

The optical train was modified to incorporate a 785 nm laser, Chroma ZT745spxrxt-UF1 dichroic filter (Chroma, Below Falls, Vt.), a ZET785nf (Chroma) emission filter, and a 4× Nikon objective.

Protocol for Examples 3 and 4. A 785 nm laser was focused on the inner surface (dielectrophoresis substrate) of a sequestration pen and cover above the pen to produce 90 milliwatts (mW) of power for approximately one second, heating the fluidic medium and generating one or more bubbles. Cells were dislodged from respective isolation regions by bubble contact force and/or shear flow generated by the bubbles. After dislodgement, OET force was used to deliver and position individual dislodged cells into adjacent pens. The newly repositioned cells were observed after 24 hours in culture to determine effect on cell viability and proliferation.

Example 3. Optically Driven Displacement of OKT3 Cells and Viability

Figure 11A:
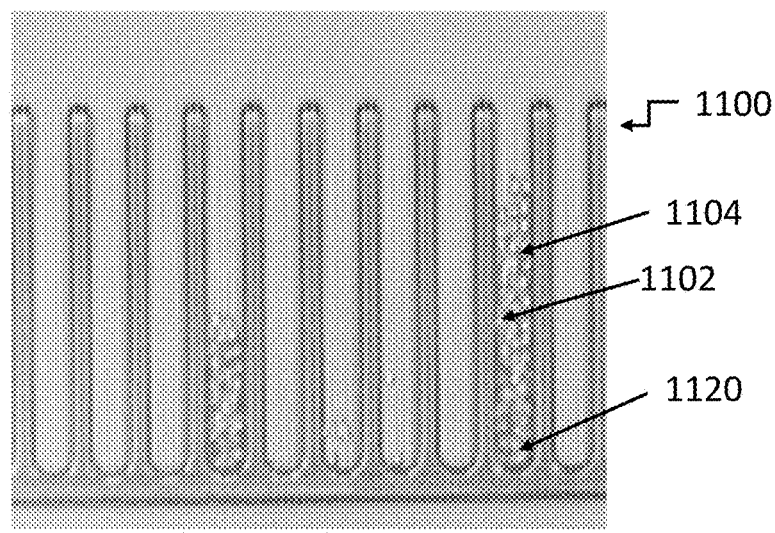
FIGS. 11A-11C are photographic representations of cells maintained in a microfluidic device before and after optically driven displacement according to the disclosure.
Figure 11B:
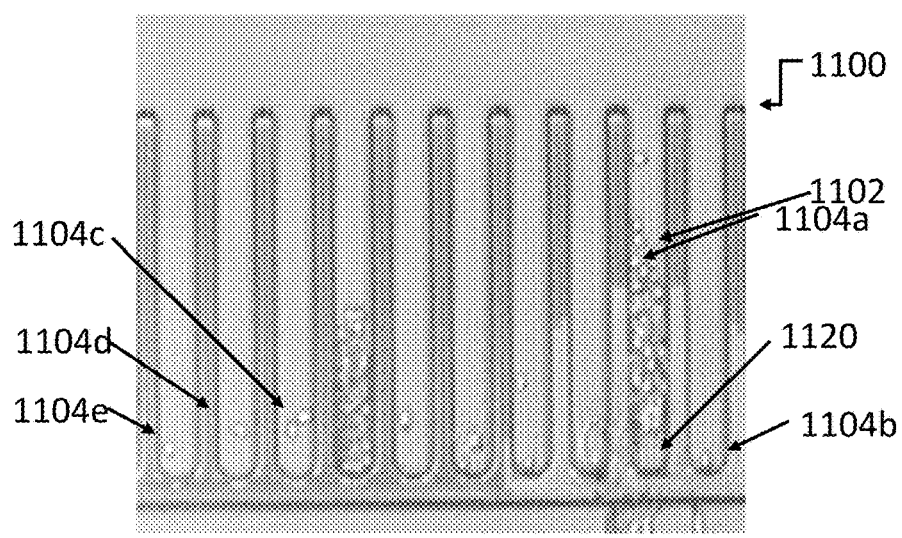
Figure 11C:
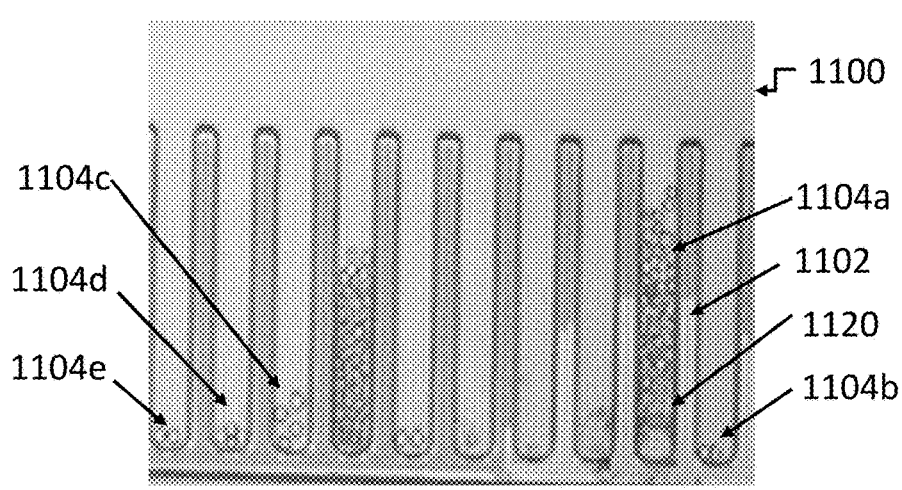

FIG. 11A-11C depict experimental results from before and after optically driven displacement and repositioning of OKT3 cells. FIG. 11A shows a series of sequestration pens of microfluidic device 1100 prior to the export of the cells 1104 from sequestration pen 1102. Optical illumination was directed towards sacrificial feature 1120, a surface of the sequestration pen 1102, which acts as a thermal target. Resultingly, cells 1104 were dislodged. Single cells were positioned in adjacent sequestration pens. FIG. 11B showed the individual dislodged and repositioned single cells 1104b, 1104c, 1104d, and 1104e in newly occupied pens after displacement and repositioning with OET. Originally occupied sequestration pen 1102 had a reduced number of cells 1104a, which may have been dislodged but remained within sequestration pen 1103. FIG. 11C showed the same sequestration pens 20 hours later. As shown in FIG. 12C, cells 1104b, 1104c, 1104d, and 1104e continued to divide and proliferate after dislodging, export, and repositioning. Additionally, the remaining cells in originally occupied sequestration pen 1102 also proliferated. These results indicated that the process of optical illumination, heating, dislodging and repositioning had no detectable effect on cell viability in this experiment. As shown in FIG. 12C the number of cells 1104c having increased from two to four; the number of cells 1104d increased from one to four, and cells 1104e increased from one to two.

Example 4. Optically Driven Displacement and Resultant Viability of JIMT-1 Cells Medium:
Serum free medium (ThermoFisher Scientific, Cat. No. 12045-096), with a conditioning culture medium additive, B-27® Supplement (2% v/v).

Figure 12A:
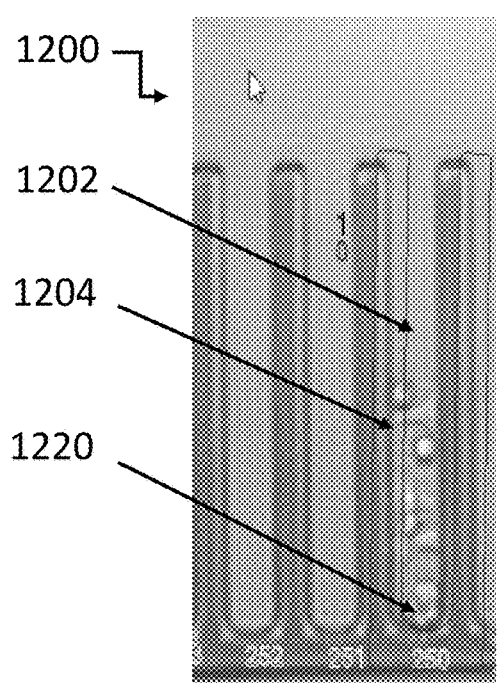
FIG. 12A-12C are photographic representations of cells maintained in a microfluidic device before and after optically driven displacement according to the disclosure.
Figure 12B:
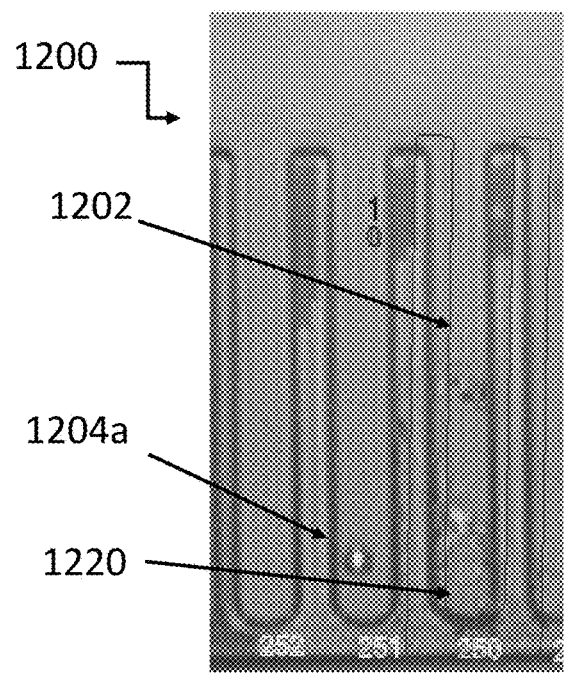
Figure 12C:
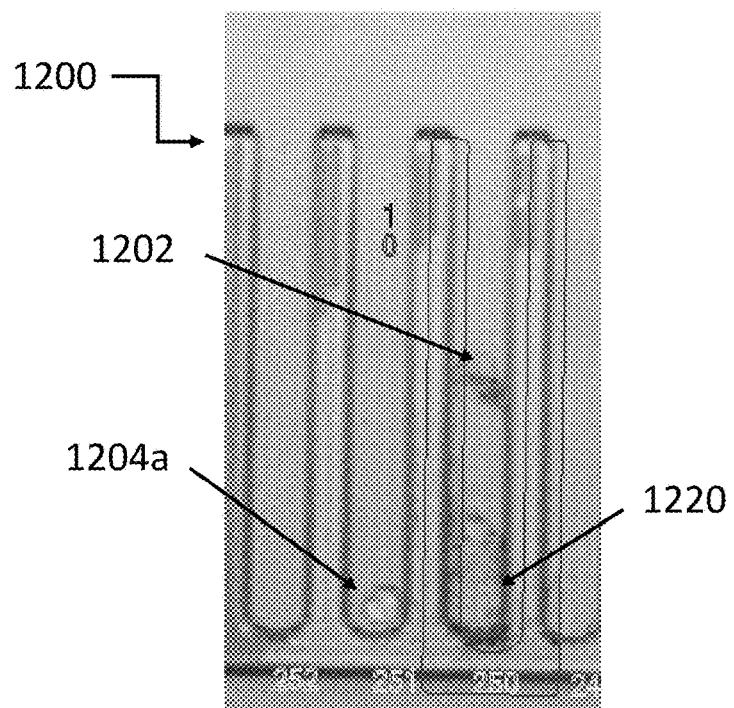

FIGS. 12A-C depict experimental results from before and after optically driven displacement and repositioning of JIMT-1 cells (commercially available from AddexBio Cat. # C0006055), an adherent human breast carcinoma cell line. FIG. 12A showed a series of sequestration pens of microfluidic device 1200 prior to the displacement of cells 1204 from sequestration pen 1202. Optical illumination was directed towards sacrificial feature 1220 (thermal target), a surface of the sequestration pen 1202, and cells 1204 were dislodged. FIG. 14B showed an individual cell 1204a, dislodged and newly repositioned in an empty sequestration pen adjacent to originally occupied sequestration pen 1202. FIG. 14C shows a timepoint 20 h after displacement and repositioning showing that cells 1204a were viable and have doubled from one cell to two, within the 20 h culture period.

Example 5. Induction of a Cyclic (Marangoni Effect) Flow

Figure 13A:
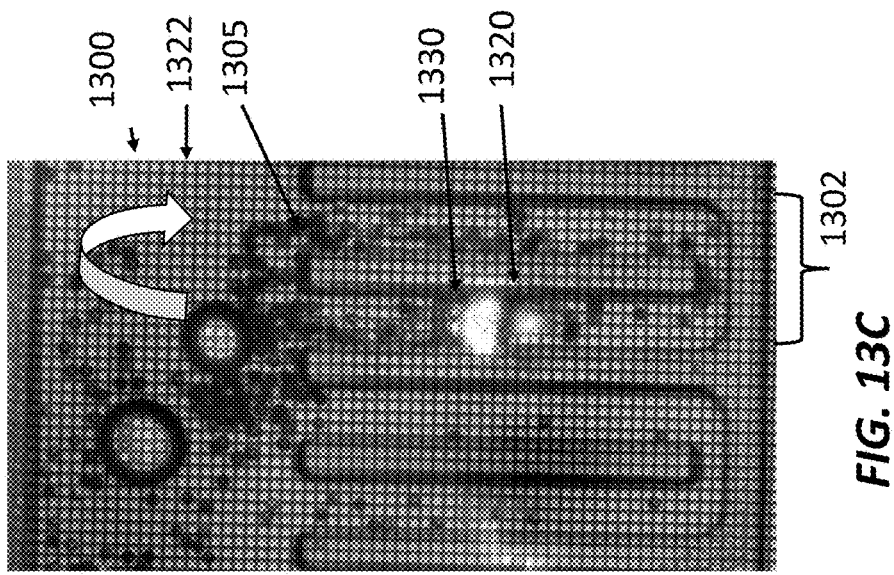
FIGS. 13A-13C are photographic representations of a method using illumination to create a cyclized flow capable of moving micro-objects.
Figure 13B:
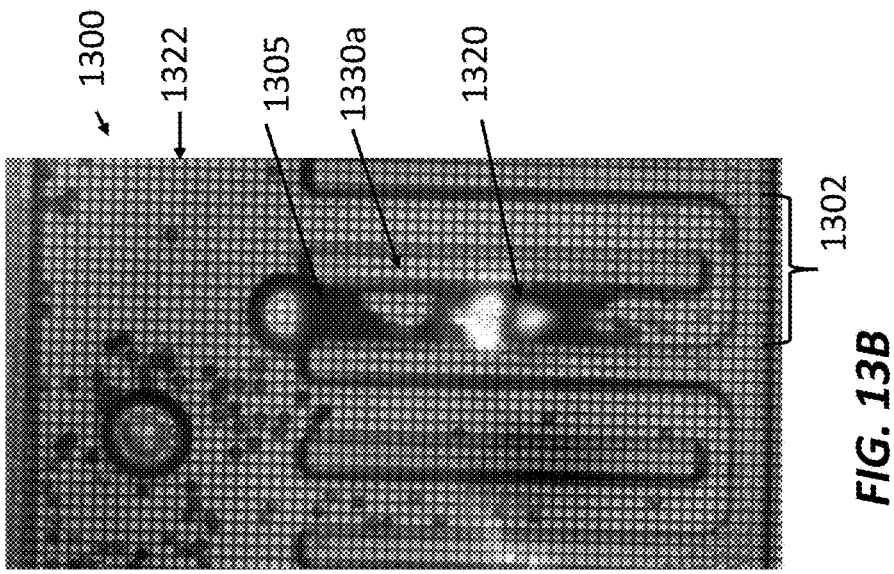
Figure 13C:
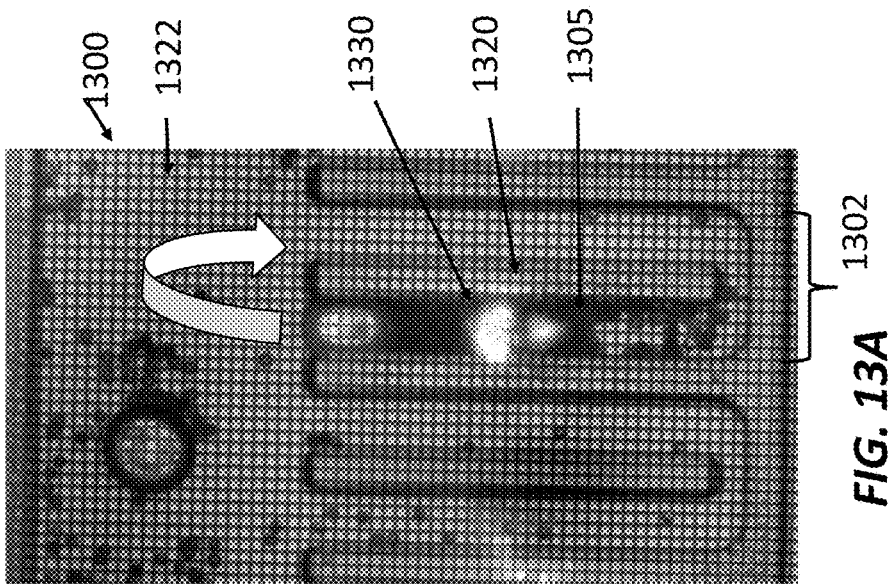

FIGS. 13A to 13C depict experimental results demonstrating a cyclic Marangoni-effect flow using a cyclic culturing pen geometry. FIG. 13A shows a number of micro-objects 1305 (6 micron diameter polystyrene beads) at a first time point during which a laser was directed at thermal target 1320 to create a bubble 1330 which causes a Marangoni effect flow within the cyclic culturing pen 1302 and adjacent channel 1322 of microfluidic device 1300. FIG. 13B shows the same cyclic culturing pen 1302 with micro-objects 1305 at a second time point (after a bubble 1330a broke away from the site of nucleation) during which the micro-objects 1305 were cycled around counterclockwise (white arrow indicates flow direction) through the culturing pen 1302 by the Marangoni-effect flow. FIG. 13C shows a third timepoint, during which laser illumination was still present. The micro-objects 1305 have pushed past the thermal target 1320, out into the channel 1322, and cycled back in to the second side of the cyclic culturing pen 1302. In the experiment illustrated in FIGS. 13A to 13C, the bubble was nucleated by focusing a 785 laser on gold thermal targets deposited on the inner surface of the cover of the microfluidic device. Specifically, the laser was used to generate a spot of light 40 microns in diameter and had 90 mW corresponding to: 1.4 kW/cm^2.

Example 6. Optically Driven Displacement of OKT3 Cells, Shorter Period of Illumination OKT3 murine hybridoma cells were cultured in fluidic medium within sequestration pens of microfluidic device 1400 as shown. FIG. 14A shows a colony of cells 1440 maintained within the central sequestration pen 1402. The group of cells are highlighted within the white oval, and no laser illumination has yet been introduced. FIG. 14B shows the same group of cells 1440 (within the white oval) in the central sequestration pen 1402 of the figure, while the laser was directed at a discrete selected point 1420 (thermal target which is a sacrificial feature) of the surface of the sequestration pen 1302 where some of the cells were contained, for a duration of time in a range of about 50 millisec to about 1000 millisec, using 1.4 amps. FIG. 14C showed that the resultant cavitation and collapse of a bubble nucleated from the heat introduced by the laser illumination dislodged and displaced a group of cells 1404b completely out of the sequestration pen 1402, and into the microfluidic channel 1422. The remainder of the cells 1404a, were somewhat displaced but were not been exported from the sequestration pen 1402.

Example 7. Optically Driven Displacement of OKT3 Cells, Longer Period of Illumination OKT3 murine hybridoma cells 1504 were maintained within a fluidic medium within sequestration pens in microfluidic device 1500 and are shown, prior to any laser illumination in FIG. 15A, where the white oval points out the colony of cells to be dislodged. Laser illumination is shown in FIG. 15B. The laser power was 1.4 amps, and the duration of the laser pulse was about 2000 millisec. The white oval surrounds the cells 1504 to be dislodged, and the discrete region of illumination 1520 is at the bottom of the sequestration pen 1502, and particularly was directed at the microfluidic circuit material forming the sequestration pen wall. The area targeted acted as a sacrificial feature (e.g., thermal target). FIG. 15C illustrates the timepoint near the end of the 2000 millisec laser illumination where the cells 1504 (within the white oval) were dislodged and were displaced towards the proximal opening of the sequestration pen to the flow region (e.g., microfluidic channel), pushed by a bubble under the group of cells 1504 (not visible). Blackening seen at the base of the sequestration pen shows destruction of the substrate material and some of the sequestration pen wall material within the sequestration pen 1502 (See also post-illumination sacrificial feature 1524, in FIG. 15D). FIG. 15D shows a time point after conclusion of optical illumination, where optically actuated dielectrophoretic forces were applied to continue moving the now dislodged cells 1504 further out of the sequestration pen 1504. In FIG. 15D, white bars 1530 1532, 1534, 1536 were the light (OET) patterns displayed upon the substrate surface, where the substrate included a dielectrophoretic configuration. As the light pattern bars 1530 1532, 1534, 1536 moved in the direction towards the opening of the sequestration pen to the microfluidic channel 1522, cells captured and repelled by the dielectrophoretic force generated by each light bar pattern, were moved toward the opening of the sequestration pen (see the cells 1504*b* and 1504*c* within the white ovals). Cells 1504*c*, being repelled by light pattern bar 1530, were fully exported from the sequestration pen, and were re-located into the flow region (e.g., a microfluidic channel 1522). FIG. 15E shows a later timepoint, when the optically actuated dielectrophoretic light patterns 1530 1532, 1534, 1536 completed a sequence of capturing, repelling and moving the cells out of the sequestration pen, and fluidic flow was restored to the flow region. Cells that had been dislodged by the laser pulse method and further moved out of the sequestration pen into the flow region were exported out of the microfluidic device. Cells 1504*d* (within white oval for emphasis) still remained in the sequestration pen but were clearly dislodged from their original position within the sequestration pen 1502, prior to laser illumination (compare with FIG. 15A). Additional sequences of optically actuated dielectrophoretic selecting and moving may permit the remaining cells to be exported out of the sequestration pen.

Recitation of Embodiments

1. A microfluidic device including an enclosure further including a flow region and a sequestration pen, wherein the sequestration pen includes: a connection region, an isolation region and a displacement force generation region, wherein: the connection region includes a proximal opening to the flow region and a distal opening to the isolation region, and the isolation region includes at least one fluidic connection to the displacement force generation region; and the displacement force generation region further includes a thermal target.

2. The microfluidic device of claim 1, wherein the at least one fluidic connection between the isolation region and the displacement force generation region includes a cross sectional dimension configured to prevent passage of a micro-object from the isolation region to the displacement force generation region.

3. The microfluidic device of embodiment 1 or 2, wherein the at least one fluidic connection between the isolation region and the displacement force generation region includes a cross sectional dimension configured to prevent fluidic flow from the displacement force generation region in the absence of a force generated therein, except by diffusion.

4. The microfluidic device of any one of embodiments 1 to 3, wherein the at least one fluidic connection between the isolation region and the displacement force generation region includes one or more barrier modules, wherein the one or more barrier modules are configured to prevent passage of a micro-object from the isolation region to the displacement force generation region.

5. The microfluidic device of any one of embodiments 1 to 5, wherein the displacement force generation region further includes an opening to the flow region.

6. The microfluidic device of any one of embodiments 1-to 5, wherein the displacement force generation region has more than one fluidic connection to the isolation region.

7. The microfluidic device of embodiment 6, wherein the sequestration pen includes a cyclic flow path.

8. The microfluidic device of embodiment 7, wherein the cyclic flow path includes a constricted portion.

9. The microfluidic device of any one of embodiments 6 to 8, further including a second thermal target configured to produce a second cyclic flow of the fluidic medium upon optical illumination.

10. The microfluidic device of embodiment 9, wherein the first thermal target and the second thermal target are oriented to provide the first cyclic flow and the second cyclic flow of the fluidic medium in opposite directions.

11. The microfluidic device of any one of embodiments 1-5, wherein the displacement force generation region includes a single opening, wherein the single opening is the fluidic connection to the isolation region.

12. The microfluidic device of any one of embodiments 1 to 11, wherein the fluidic connection of the displacement force generation region includes a fluidic connector including at least one curved portion.

13. The microfluidic device of embodiment 12, wherein the at least one curved portion of the fluidic connector includes a turn of about 60 degrees to about 180 degrees.

14. The microfluidic device of embodiment 12 or 13, wherein the fluidic connector of the displacement force generation region includes at least two curved portions.

15. The microfluidic device of embodiment 14, wherein each of the at least two curved portions of the fluidic connector includes a turn of about 60 degrees to about 180 degrees.

16. The microfluidic device of any one of embodiments 12 to 15, wherein a width of the fluidic connector is the same as a width of the isolation region and/or the displacement force generating region.

17. The microfluidic device of any one of embodiments 12- to 15, wherein the fluidic connector includes a cross sectional dimension configured to prevent passage of a micro-object from the isolation region to the displacement force generation region.

18. The microfluidic device of any one of embodiments 1 to 17, wherein the enclosure of the microfluidic device further includes a cover that defines, in part, the sequestration pen, wherein the thermal target is disposed on the cover.

19. The microfluidic device of embodiment 18, wherein the thermal target is disposed on an inner surface of the cover facing the enclosure.

20. The microfluidic device of any one of embodiments 1 to 17, wherein the enclosure of the microfluidic device further includes a microfluidic circuit structure that defines, in part, the sequestration pen, and wherein the thermal target is disposed on the microfluidic circuit structure.

21. The microfluidic device of any one of embodiments 1 to 17, wherein the enclosure of the microfluidic device further includes a base that defines, in part, the sequestration pen, and wherein the thermal target is disposed on an inner surface of the base.

22. The microfluidic device of any one of embodiments 1 to 21, wherein the thermal target includes a metal.

23. The microfluidic device of any one of embodiments 1 to 22, wherein the thermal target has a contiguous shape.

24. The microfluidic device of any one of embodiments 1 to 22, wherein the thermal target has a non-contiguous shape.

25. The microfluidic device of any one of embodiments 1 to 22 or 24, wherein the thermal target includes a plurality of microstructures.

26. The microfluidic device of any one of embodiments 1 to 21 or 23 to 25, wherein the thermal target is a sacrificial feature.

27. The microfluidic device of any one of embodiments 1 to 26, wherein the thermal target or the displacement force generation region is configured to constrain expansion of a gaseous bubble formed thereupon in one predominate direction.

28. The microfluidic device of any one of embodiments 1 to 27, wherein the thermal target is positioned in a portion of the displacement force generation region distal to the least one fluidic connection to the isolation region.

29. The microfluidic device of embodiment 28, wherein the displacement force generation region has a width of approximately 20-100 microns.

30. The microfluidic device of any one of embodiments 1 to 29, wherein the enclosure further includes a dielectrophoresis configuration.

31. The microfluidic device of embodiment 30, wherein the dielectrophoresis configuration is optically actuated.

32. The microfluidic device of any one of embodiments 1 to 31, wherein the sequestration pen includes at least one surface that is a coated surface.

33. The microfluidic device of embodiment 32, wherein the coated surface is a covalently linked surface.

34. A microfluidic device including an enclosure including a microfluidic circuit configured to contain a fluidic medium, wherein the microfluidic circuit is configured to accommodate at least one cyclic flow of the fluidic medium; and a first thermal target disposed on a surface of the enclosure within the microfluidic circuit, wherein the first thermal target is configured to produce a first cyclic flow of the fluidic medium upon optical illumination.

35. The microfluidic device of embodiment 34, wherein the thermal target has a contiguous shape.

36. The microfluidic device of embodiment 34, wherein the thermal target has a pattern of shapes.

37. The microfluidic device of any one of embodiments 34 to 36, wherein the thermal target includes a non-uniform thickness on the surface of the enclosure, wherein the non-uniform thickness is configured to provide differential heating of the fluidic medium by the thermal target upon optical illumination.

38. The microfluidic device of embodiment 36 or 37, wherein the pattern of shapes is configured to provide differential heating of the fluidic medium by the thermal target upon optical illumination.

39. The microfluidic device of any one of embodiments 34 to 38, wherein the thermal target includes a metal.

40. The microfluidic device of any one of embodiments 34 to 39, wherein the thermal target includes a plurality of microstructures.

41. The microfluidic device of embodiment 40, wherein the plurality of microstructures includes a pattern of increasing density of microstructures configured to provide differential heating of the fluidic medium by the thermal target upon optical illumination.

42. The microfluidic device of any one of embodiments 34 to 41, wherein the enclosure of the microfluidic device further includes a microfluidic channel and a sequestration pen, and further wherein the sequestration pen is adjacent to and opens off of the microfluidic channel.

43. The microfluidic device of embodiment 42, wherein the cyclic flow path includes a portion of the channel and at least a portion of the sequestration pen.

44. The microfluidic device of embodiment 42, wherein the sequestration pen includes the cyclic flow path.

45. The microfluidic device of any one of embodiments 34 to 44, wherein the cyclic flow path includes a constricted portion.

46. The microfluidic device of any one of embodiments 34 to 45, further including a second thermal target configured to produce a second cyclic flow of the fluidic medium upon optical illumination.

47. The microfluidic device of embodiment 46, wherein the first thermal target and the second thermal target are oriented to provide the first cyclic flow and the second cyclic flow of the fluidic medium in opposite directions.

48. The microfluidic device of embodiment 42, wherein the thermal target is disposed on a surface within the microfluidic channel.

49. The microfluidic device of any one of embodiments 34 to 41, wherein the enclosure of the microfluidic device further includes more than one microfluidic channel, wherein a first microfluidic channel is configured to open from a second microfluidic channel at a first location along the second microfluidic channel and is further configured to reconnect to the second microfluidic channel at a second location thereby forming the microfluidic circuit; and the thermal target is disposed on a surface within the first microfluidic channel.

50. The microfluidic device of embodiment 49, wherein at least one sequestration pen opens off of the first microfluidic channel.

51. The microfluidic device of embodiment 49 or 50, wherein a fluidic resistance of the first channel is approximately 10 to 100 times higher than a fluidic resistance of the second channel.

52. The microfluidic device of any one of embodiments 49 to 51, wherein the second microfluidic channel includes a width that is approximately 1.5 to 3 times larger than a width of the first microfluidic channel.

53. The microfluidic device of embodiment 52, wherein the width of the second microfluidic channel is about 100 to 1000 microns.

54. The microfluidic device of any one of embodiments 49 to 53, wherein the width of the first microfluidic channel is about 20 to 300 microns.

55. A microfluidic device including an enclosure including: a microfluidic channel and a sequestration pen, and further wherein the sequestration pen is adjacent to and opens off of the microfluidic channel and a thermal target is disposed in the channel adjacent to an opening to a sequestration pen, and wherein the thermal target is further configured to direct a flow of the fluidic medium into the sequestration pen upon optical illumination.

56. The microfluidic device of embodiment 55, wherein the thermal target is disposed on a surface within the microfluidic channel.

57. The microfluidic device of embodiment 55 or 56, wherein the thermal target has a contiguous shape.

58. The microfluidic device of embodiment 55 or 56, wherein the thermal target has a pattern of shapes.

59. The microfluidic device of any one of embodiments 55 to 58, wherein the thermal target includes a non-uniform thickness on the surface of the enclosure, wherein the non-uniform thickness is configured to provide differential heating of the fluidic medium by the thermal target upon optical illumination.

60. The microfluidic device of embodiment 58 or 59, wherein the pattern of shapes is configured to provide differential heating of the fluidic medium by the thermal target upon optical illumination.

61. The microfluidic device of any one of embodiments 55 to 60, wherein the thermal target includes a metal.

62. The microfluidic device of any one of embodiments 55 to 60, wherein the thermal target includes a plurality of microstructures.

63. The microfluidic device of embodiment 62, wherein the plurality of microstructures includes a pattern of increasing density of microstructures configured to provide differential heating of the fluidic medium by the thermal target upon optical illumination.

64. A kit for culturing micro-objects including: a microfluidic device of any one of embodiments 1-63; and, one or more reagents configured to provide at least one coated surface within an enclosure of the microfluidic device.

65. The kit of embodiment 64, further including at least one fluidic medium.

66. A method of dislodging one or more micro-objects within a microfluidic device, the method including the steps of: illuminating a selected discrete region containing or adjacent to one or more micro-objects disposed within a fluidic medium in an enclosure of the microfluidic device, wherein the enclosure includes a microfluidic circuit including a flow region and a substrate; maintaining the illumination of the selected discrete region of a first period of time sufficient to generate a dislodging force, dislodging the one or more micro-objects from the surface.

67. The method of embodiment 66, wherein the selected discrete region has an area of about 100 square microns.

68. The method of embodiment 66, wherein the selected discrete region has an area of about 25 square microns.

69. The method of embodiment 66, wherein the step of illuminating includes illuminating the selected discrete region with a laser.

70. The method of any one of embodiments 66 to 69, wherein the one or more micro-objects are disposed upon a surface of the substrate.

71. The method of any one of embodiments 66 to 70, further including a step of maintaining the one or more micro-objects within the fluidic medium in the enclosure for a second period of time before performing the step of illuminating the selected discrete region.

72. The method of any one of embodiments 66 to 71, wherein the enclosure of the microfluidic device includes at least one sequestration pen.

73. The method of embodiment 72, wherein the one or more micro-objects are disposed and/or maintained on a surface of the substrate within the at least one sequestration pen.

74. The method of any one of embodiments 66 to 73, wherein the step of illuminating the selected discrete region includes illuminating with illumination having incident power in the range of about 1 mW to about 1000 mW.

75. The method of embodiment 74, wherein the first period of time is in the range from 10 microsec to 3000 millisec or 100 millisec to 3 minutes.

76. The method of any one of embodiments 66 to 75, wherein the step of illuminating includes illuminating at least one of the one or more micro-objects.

77. The method of embodiment 76, wherein the first period of time is in the range of 10 microsec to 200 millisec, thereby creating a cavitating force dislodging the one or more micro-objects.

78. The method of embodiment 76 or 77, wherein, when the one or more micro-objects are disposed and/or maintained within the at least one sequestration pen, the selected discrete region is a location distal to a proximal opening of the sequestration pen to the flow region or at a central location of the at least one sequestration pen.

79. The method of any one of embodiments 66 to 78, wherein the selected discrete region is a selected point adjacent to the one or more micro-objects.

80. The method of embodiment 79, wherein the step of illuminating the selected discrete region includes directing illumination towards the substrate; microfluidic circuit material of a wall; or a thermal target.

81. The method of embodiment 80, wherein the thermal target includes a metal deposit, a pattern of metal deposits, or microstructures patterned on a surface.

82. The method of embodiment 80 or 81, wherein the thermal target includes a sacrificial feature.

83. The method of any one of embodiments 79 to 82, wherein when the one or more micro-objects are disposed within at least one sequestration pen within the enclosure, the s selected discrete region is located near a proximal opening of the at least one sequestration pen to the flow region.

84. The method of any one of embodiments 79 to 82, wherein when the one or more micro-objects are disposed within at least one sequestration pen within the enclosure, the selected discrete region includes a selected point of microfluidic circuit material that helps to define the at least one sequestration pen.

85. The method of any one of embodiments 79 to 82, wherein when the one or more micro-objects are maintained within at least one sequestration pen within the enclosure, the selected discrete region includes a sacrificial feature disposed within the at least one sequestration pen.

86. The method of embodiment 85, wherein the sacrificial feature includes microfluidic circuit material.

87. The method of any one of embodiments 79 to 86, wherein the first period of time is in the range of about 10 microsec to 200 millisec.

88. The method of any one of embodiments 79 to 87, wherein the step of illuminating the selected discrete region further includes heating a first portion of the fluidic medium located within or adjacent to the selected discrete region, thereby creating a cavitating force.

89. The method of any one of embodiments 79 to 87, wherein the method further includes: heating a first portion of the fluidic medium; and creating a persistent gaseous bubble displacing a second portion of the fluidic medium surrounding the one or more micro-object.

90. The method of embodiment 89, wherein the step of displacing a second portion of the fluidic medium further includes creating a cyclic fluidic flow of the fluidic medium during the first period of illumination.

91. The method of any one of embodiments 79 to 87, wherein the method further includes: heating a first portion of the fluidic medium; and creating one or more gaseous bubbles, thereby creating a shear flow of the fluidic medium towards the one or more micro-objects.

92. The method of any one of embodiments 79 to 87, wherein the method further includes: heating a first portion of the fluidic medium; creating a plurality of gaseous bubbles configured to stream towards the one or more micro-objects; and contacting the one or more micro-objects with a meniscus of at least one gaseous bubble of the plurality of gaseous bubble.

93. The method of any one of embodiments 89 to 92, wherein the first period of time is in the range of about 100 millisec to about 3000 minutes.

94. The method of embodiment 91 or 92, wherein the first period is in the range of about 1000 millisec to about 2000 millisec.

95. The method of any one of embodiments 79 to 94, wherein when the one or more micro-objects are maintained within a sequestration pen within the enclosure, the selected discrete region includes at least a part of a wall forming a distal end of the sequestration pen, wherein the wall is positioned opposite to a proximal opening to the flow region.

96. The method of any one of embodiments 79 to 94, wherein when the one or more micro-objects are disposed within a sequestration pen within the enclosure, the selected discrete region is located in a displacement force generation region of the sequestration pen.

97. The method of embodiment 96, wherein the one or more micro-objects are disposed within an isolation region of the sequestration pen and the displacement force generation region is fluidically connected to the isolation region.

98. The method of any one of embodiments 66 to 93, further including a step of exporting the one or more micro-objects from at least one sequestration pen disposed within the enclosure.

99. The method of embodiment 98, wherein the step of exporting the one or more micro-objects from the at least one sequestration pen includes moving the one or more micro-objects with dielectrophoresis force.

100. The method of any one of embodiments 66 to 99, further including a step of exporting the one or more micro-objects from the flow region of the enclosure of the microfluidic device.

101. The method of embodiment 100, wherein the step of exporting the one or more micro-objects from the flow region includes using fluidic flow or dielectrophoresis forces.

102. A method of mixing fluidic media, and/or micro-objects contained therein, within an enclosure of a microfluidic device, the method including: focusing a light source on a thermal target disposed on a surface of the enclosure within a microfluidic circuit including at least one fluidic medium and/or micro-objects, thereby heating a first portion of the at least one fluidic medium; and inducing a cyclic flow of the at least one fluidic medium within the microfluidic circuit thereby mixing the fluidic media and/or micro-objects disposed therein.

103. The method of embodiment 102, wherein the thermal target is disposed within a first microfluidic channel which is configured to branch off of a second fluidic channel at a first location and is also configured to rejoin the second fluidic channel at a second location, wherein the thermal target is disposed on the surface therebetween.

Although specific embodiments and applications of the disclosure have been described in this specification, these embodiments and applications are exemplary only, and many variations are possible.

The invention claimed is:

1. A microfluidic device comprising an enclosure further comprising a flow region and a sequestration pen, wherein the sequestration pen comprises:
   a connection region, an isolation region and a displacement force generation region, wherein:
   the connection region comprises a proximal opening to the flow region and a distal opening to the isolation region;
   the isolation region comprises at least one fluidic connection to the displacement force generation region, wherein the at least one fluidic connection between the isolation region and the displacement force generation region is configured to prevent passage of a micro-object from the isolation region to the displacement force generation region; and
   the displacement force generation region further comprises a thermal target.

2. The microfluidic device of claim 1, wherein the at least one fluidic connection between the isolation region and the displacement force generation region comprises a cross sectional dimension configured to prevent passage of a micro-object from the isolation region to the displacement force generation region.

3. The microfluidic device of claim 1, wherein one or more barrier modules in the displacement force generation region form a gap between the one or more barrier modules and a wall of the sequestration pen, providing the at least one fluidic connection between the isolation region and the displacement force generation region wherein the gap is configured to prevent passage of a micro-object from the isolation region to the displacement force generation region.

4. The microfluidic device of claim 1, wherein the enclosure of the microfluidic device further comprises a microfluidic circuit structure that defines, in part, the sequestration pen, and wherein the thermal target is disposed on the microfluidic circuit structure.

5. The microfluidic device of a claim 1, wherein the enclosure of the microfluidic device further comprises a base that defines, in part, the sequestration pen, and wherein the thermal target is disposed on an inner surface of the base.

6. The microfluidic device of claim 1, wherein the thermal target is positioned in a portion of the displacement force generation region distal to the least one fluidic connection to the isolation region.

7. The microfluidic device of claim 1, wherein the fluidic connection comprises a constricted fluidic connector that connects the isolation region to the displacement force generation region, wherein the dimension of the constricted fluidic connector is narrowed relative to the isolation region, thereby preventing passage of the micro-object.

8. The microfluidic device of claim 1, wherein the displacement force generation region has more than one fluidic connection to the isolation region.

9. The microfluidic device of claim 1, wherein the displacement force generation region comprises a single opening, wherein the single opening is the fluidic connection to the isolation region.

10. The microfluidic device of claim 1, wherein each of the one or more barrier modules in the displacement force generation region comprises a gap between each of the one or more barrier modules and its neighbor, wherein the gap is configured to prevent passage of a micro-object from the isolation region to the displacement force generation region.

11. The microfluidic device of claim 1, wherein the displacement force generation region comprises a fluidic connector comprising at least one curved portion.

12. The microfluidic device of claim 11, wherein the at least one curved portion of the fluidic connector comprises a turn of about 60 degrees to about 180 degrees.

13. The microfluidic device of claim 11, wherein the fluidic connector of the displacement force generation region comprises at least two curved portions.

14. The microfluidic device of claim 13, wherein each of the at least two curved portions of the fluidic connector comprises a turn of about 60 degrees to about 180 degrees.

15. The microfluidic device of claim 1, wherein the thermal target is a sacrificial feature.

16. The microfluidic device of claim 1, wherein the enclosure of the microfluidic device further comprises a base that defines, in part, the sequestration pen, wherein the thermal target is disposed on an inner surface of the base.

17. The microfluidic device of claim 1, wherein the displacement force generation region is configured to constrain expansion of a gaseous bubble formed thereupon in one predominate direction.

18. A microfluidic device comprising an enclosure further comprising a flow region and a sequestration pen, wherein the sequestration pen comprises:
   a connection region, an isolation region and a displacement force generation region, wherein:
   the connection region comprises a proximal opening to the flow region and a distal opening to the isolation region;
   the isolation region comprises at least one fluidic connection to the displacement force generation region, wherein the at least one fluidic connection comprises a cross sectional dimension less than about 11 microns; and
   the displacement force generation region further comprises a thermal target.

19. The microfluidic device of claim 18, wherein the thermal target is a sacrificial feature.

20. A microfluidic device comprising an enclosure further comprising a flow region and a sequestration pen, wherein the sequestration pen comprises:
   a connection region, an isolation region and a displacement force generation region, wherein:
   the connection region comprises a proximal opening to the flow region and a distal opening to the isolation region;
   the isolation region comprises at least one fluidic connection to the displacement force generation region, wherein the at least one fluidic connection comprises a cross sectional dimension configured to prevent fluidic flow from the displacement force generation region in the absence of a force generated therein; and
   the displacement force generation region further comprises a thermal target, and is configured to minimize secondary flows of fluidic media to maximize the force generated therein towards the isolation region.

21. The microfluidic device of claim 20, wherein the displacement force region comprises elongate dimensions, and the thermal target is disposed at the distal portion of the displacement region and is configured to direct the force generated therein in the direction towards the fluidic connection with the isolation region.

* * * * *